US009321999B2

(12) United States Patent
Kahre et al.

(10) Patent No.: US 9,321,999 B2
(45) Date of Patent: Apr. 26, 2016

(54) COMPOSITIONS FOR INCREASING POLYPEPTIDE STABILITY AND ACTIVITY, AND RELATED METHODS

(75) Inventors: Olev Kahre, Tartu (EP); Kadri Artma, Tartumaa (EP); Tiina Kahre, Tartu (EP)

(73) Assignee: SOLIS BIODYNE OÜ, Tartu (EE)

( * ) Notice: Subject to any disclaimer, the term of this patent is extended or adjusted under 35 U.S.C. 154(b) by 399 days.

(21) Appl. No.: 12/950,349

(22) Filed: Nov. 19, 2010

(65) Prior Publication Data
US 2011/0142792 A1  Jun. 16, 2011

Related U.S. Application Data

(60) Provisional application No. 61/390,857, filed on Oct. 7, 2010, provisional application No. 61/356,541, filed on Jun. 18, 2010, provisional application No. 61/350,457, filed on Jun. 1, 2010, provisional application No. 61/262,919, filed on Nov. 19, 2009.

(51) Int. Cl.
*C12P 21/04* (2006.01)
*C12N 9/12* (2006.01)
*C07K 14/435* (2006.01)
*C12N 9/00* (2006.01)
*C07K 14/00* (2006.01)
*C12N 9/14* (2006.01)
*C12N 9/22* (2006.01)
*C12N 9/50* (2006.01)
*C12N 9/78* (2006.01)
*C12N 9/96* (2006.01)

(52) U.S. Cl.
CPC . *C12N 9/00* (2013.01); *C07K 14/00* (2013.01); *C12N 9/1252* (2013.01); *C12N 9/1276* (2013.01); *C12N 9/14* (2013.01); *C12N 9/22* (2013.01); *C12N 9/50* (2013.01); *C12N 9/78* (2013.01); *C12N 9/96* (2013.01); *C07K 2319/21* (2013.01); *C07K 2319/35* (2013.01); *C07K 2319/50* (2013.01)

(58) Field of Classification Search
None
See application file for complete search history.

(56) References Cited

U.S. PATENT DOCUMENTS 6,627,424 B1 * 9/2003 Wang ............................ 435/194
2005/0037412 A1 2/2005 Meier et al.

OTHER PUBLICATIONS

Fagain. Understanding and increasing protein stability. Biochim Biophys Acta. Sep. 27, 1995;1252(1):1-14.
FIREPol 5x Master Mix Ready to Load. Technical characteristics Information. 2007.
FIREPol DNA Polymerase I (for PCR) Solis BioDyne datasheet. 2008.
FIREPol DNA Polymerase I (for PCR) Technical characteristics Information. 2000-2002.
FIREPol DNA Polymerase I (for PCR) Technical characteristics Information. 2003-2004.
FIREPol DNA Polymerase I (for PCR) Technical characteristics Information. 2007.
Hot FIREPol DNA Polymerase I (for HOT Sart PCR) (HOT Start DNA Polymerase) Technical characteristics Information. 2003.
Hot FIREPol DNA Polymerase I (for HOT Sart PCR) (HOT Start DNA Polymerase) Technical characteristics Information. 2004.
Hot FIREPol DNA Polymerase I (HOT Start DNA Polymerase) Solis BioDyne datasheet. 2008.
International search report dated May 20, 2011 for PCT/IB2010/003127.
Kim, et al. Expression of human interferon alpha-1 with enhanced stability via the tagging system of a stabilizing peptide. Protein Expr Purif. Feb. 2009;63(2):140-6.
Lee, et al. Stabilizing peptide fusion for solving the stability and solubility problems of therapeutic proteins. Pharm Res. Oct. 2005;22(10):1735-46.
Solis Biodyne: "FIREPol DNA Polymerase". Internet citation. Accessed Jun. 3, 2011. www.sbd.ee/index.php?lan=EN&sid=70 &tid=33&active=62&activel=99.
FIREPol 5x Master Mix Ready to Load. Technical characteristics Information. 2007. FIREPol DNA Polymerase containing a polypeptide of SEQ ID No. 2 was sold in the United States.
FIREPol DNA Polymerase I (for PCR) Solis BioDyne datasheet. 2008. FIREPol DNA Polymerase I containing a polypeptide of SEQ ID No. 2 was sold in the United States.
FIREPol DNA Polymerase I (for PCR) Technical characteristics Information. 2000-2002. FIREPol DNA Polymerase I containing a polypeptide of SEQ ID No. 2 was sold in the United States.
FIREPol DNA Polymerase I (for PCR) Technical characteristics Information. 2003-2004. FIREPol DNA Polymerase I containing a polypeptide of SEQ ID No. 2 was sold in the United States.
FIREPol DNA Polymerase I (for PCR) Technical characteristics Information. 2007. FIREPol DNA Polymerase I containing a polypeptide of SEQ ID No. 2 was sold in the United States.
Hot FIREPol DNA Polymerase I (for HOT Sart PCR) (HOT Start DNA Polymerase) Technical characteristics Information. 2003. Hot FIREPol DNA Polymerase I containing a polypeptide of SEQ ID No. 2 was sold in the United States.

(Continued)

*Primary Examiner* — Marianne P Allen
(74) *Attorney, Agent, or Firm* — Wilson Sonsini Goodrich & Rosati

(57) ABSTRACT

This disclosure provides peptides, polypeptides, fusion polypeptides, compositions, and methods for enhancing or increasing the stability of a polypeptide (e.g., Taq polymerase). Such peptides, polypeptides, fusion polypeptides, or compositions include polypeptides linked to a peptide tag that enhances the stability of the polypeptide. The peptides, polypeptides, fusion polypeptides, compositions may also enhance the activity, specificity, and/or fidelity of other polypeptides in a reaction mixture. The disclosure also provides methods of using such peptides, polypeptides, fusion polypeptides, compositions.

18 Claims, 26 Drawing Sheets

(56) References Cited

OTHER PUBLICATIONS

Hot FIREPol DNA Polymerase I (for HOT Sart PCR) (HOT Start DNA Polymerase) Technical characteristics Information. 2004. Hot FIREPol DNA Polymerase I containing a polypeptide of SEQ ID No. 2 was sold in the United States.

Hot FIREPol DNA Polymerase I (HOT Start DNA Polymerase) Solis BioDyne datasheet. 2008. Hot FIREPol DNA Polymerase I containing a polypeptide of SEQ ID No. 2 was sold in the United States.

Terpe. Overview of tag protein fusions: from molecular and biochemical fundamentals to commercial systems. Applied Microbiology and Biotechnology. 2003; 60(5):523-533.

* cited by examiner

Amino Acid Sequence of Peptide
(SEQ ID NO: 1)

MIDLQRPSAA TMVDDLQRPH HHHHHPWDYK DDDDKPRWNS GW

FIGURE 3

Amino Acid Sequence of Peptide-Taq Fusion Protein
(SEQ ID NO: 2)

```
  1 MIDLQRPSAA TMVDDLQRPH HHHHHPWDYK DDDDKPRWNS GWLPLFEPKG RVLLVDGHHL
 61 AYRTFHALKG LTTSRGEPVQ AVYGFAKSLL KALKEDGDAV IVVFDAKAPS FRHEAYGGYK
121 AGRAPTPEDF PRQLALIKEL VDLLGLARLE VPGYEADDVL ASLAKKAEKE GYEVRILTAD
181 KDLYQLLSDR IHVLHPEGYL ITPAWLWEKY GLRPDQWADY RALTGDESDN LPGVKGIGEK
241 TARKLLEEWG SLEALLKNLD RLKPAIREKI LAHMDDLKLS WDLAKVRTDL PLEVDFAKRR
301 EPDRERLRAF LERLEFGSLL HEFGLLESPK ALEEAPWPPP EGAFVGFVLS RKEPMWADLL
361 ALAAARGGRV HRAPEPYKAL RDLKEARGLL AKDLSVLALR EGLGLPPGDD PMLLAYLLDP
421 SNTTPEGVAR RYGGEWTEEA GERAALSERL FANLWGRLEG EERLLWLYRE VERPLSAVLA
481 HMEATGVRLD VAYLRALSLE VAEEIARLEA EVFRLAGHPF NLNSRDQLER VLFDELGLPA
541 IGKTEKTGKR STSAAVLEAL REAHPIVEKI LQYRELTKLK STYIDPLPDL IHPRTGRLHT
601 RFNQTATATG RLSSSDPNLQ NIPVRTPLGQ RIRRAFIAEE GWLLVALDYS QIELRVLAHL
661 SGDENLIRVF QEGRDIHTET ASWMFGVPRE AVDPLMRRAA KTINFGVLYG MSAHRLSQEL
721 AIPYEEAQAF IERYFQSFPK VRAWIEKTLE EGRRRGYVET LFGRRRYVPD LEARVKSVRE
781 AAERMAFNMP VQGTAADLMK LAMVKLFPRL EEMGARMLLQ VHDELVLEAP KERAEAVARL
841 AKEVMEGVYP LAVPLEVEVG IGEDWLSAKE
```

FIGURE 4

Nucleotide Sequence of Peptide
(SEQ ID NO: 3)

```
  1 acacaggaaa cagcgatgat cgacctgcag cggccatccg ccgccaccat ggtcgacgac
 61 ctgcagcggc cgcaccatca ccatcaccat ccatgggatt acaaggacga cgatgacaag
121 ccgcggtgga attcggggtg g
```

FIGURE 5

Nucleotide Sequence of Peptide-Taq Fusion Protein
(SEQ ID NO: 4)

```
   1 acacaggaaa cagcgatgat cgacctgcag cggccatccg ccgccaccat ggtcgacgac
  61 ctgcagcggc cgcaccatca ccatcaccat ccatgggatt acaaggacga cgatgacaag
 121 ccgcggtgga attcggggtg gctgcccctc tttgagccca agggccgggt cctcctggtg
 181 gacggccacc acctggccta ccgcaccttc cacgccctga agggcctcac caccagccgg
 241 ggggagccgg tgcaggcggt ctacggcttc gccaagagcc tcctcaaggc cctcaaggag
 301 gacggggacg cggtgatcgt ggtctttgac gccaaggccc cctccttccg ccacgaggcc
 361 tacgggggt acaaggcggg ccggccccc acgccggagg actttccccg gcaactcgcc
 421 ctcatcaagg agctggtgga cctcctgggg ctggcgcgcc tcgaggtccc gggctacgag
 481 gcggacgacg tcctggccag cctggccaag aaggcggaaa aggagggcta cgaggtccgc
 541 atcctcaccg ccgacaaaga cctttaccag ctcctttccg accgcatcca cgtcctccac
 601 cccgaggggt acctcatcac cccggcctgg ctttgggaaa agtacggcct gaggcccgac
 661 cagtgggccg actaccgggc cctgaccggg gacgagtccg caaccttcc cggggtcaag
 721 ggcatcgggg agaagacggc gaggaagctt ctggaggagt gggggagcct ggaagccctc
 781 ctcaagaacc tggaccggct gaagcccgcc atccgggaga gatcctggc ccacatggac
 841 gatctgaagc tctcctggga cctggccaag gtgcgcaccg acctgcccct ggaggtggac
 901 ttcgccaaaa ggcgggagcc cgaccgggag aggcttaggg cctttctgga gaggcttgag
 961 tttggcagcc tcctccacga gttcggcctt ctggaaagcc caaggccct ggaggaggcc
1021 ccctggcccc cgccggaagg ggccttcgtg ggctttgtgc tttcccgcaa ggagcccatg
1081 tgggccgatc ttctggccct ggccgccgcc aggggggcc gggtccaccg ggcccccgag
1141 ccttataaag ccctcaggga cctgaaggag gcgcggggc ttctcgccaa agacctgagc
1201 gttctggccc tgagggaagg ccttggcctc ccgccggcg acgacccat gctcctcgcc
1261 tacctcctgg acccttccaa caccaccccc gaggggtgg cccggcgcta cggcggggag
1321 tggacggagg aggcggggga gcggccgcc ctttccgaga ggctcttcgc caacctgtgg
1381 gggaggcttg aggggagga gaggctcctt tggctttacc gggaggtgga gaggcccctt
1441 tccgctgtcc tgcccacat ggaggccacg ggggtgcgcc tggacgtggc ctatctcagg
1501 gccttgtccc tggaggtggc cgaggagatc gcccgcctcg aggccgaggt cttccgcctg
1561 gccggccacc ccttcaacct caactcccgg gaccagctgg aaagggtcct ctttgacgag
1621 ctagggcttc ccgccatcgg caagacggag aagaccggca gcgctccac cagcgccgcc
1681 gtcctggagg ccctccgcga ggcccacccc atcgtggaga gatcctgca gtaccgggag
1741 ctcaccaagc tgaagagcac ctacattgac cccttgccgg acctcatcca ccccaggacg
1801 ggccgcctcc acacccgctt caaccagacg gccacggca cgggcaggct aagtagctcc
1861 gatcccaacc tccagaacat ccccgtccgc acccgcttg ggcagaggat ccgccgggcc
1921 ttcatcgccg aggaggggtg gctattggtg gccctggact atagccagat agagctcagg
1981 gtgctggccc acctctccgg cgacgagaac ctgatccggg tcttccagga ggggcgggac
2041 atccacacgg agaccgccag ctggatgttc ggcgtccccc gggaggccgt ggacccctg
2101 atgcgccggg cggccaagac catcaacttc ggggtcctct acggcatgtc ggcccaccgc
2161 ctctcccagg agctagccat cccttacgag gaggcccagg ccttcattga gcgctacttt
2221 cagagcttcc caaggtgcg ggcctggatt gagaagaccc tggaggaggg caggaggcgg
2281 gggtacgtgg agaccctctt cggccgccgc cgctacgtgc agacctaga ggcccgggtg
2341 aagagcgtgc gggaggcggc cgagcgcatg gccttcaaca tgcccgtcca gggcaccgcc
2401 gccgacctca tgaagctggc tatggtgaag ctcttcccca ggctggagga atgggggcc
2461 aggatgctcc ttcaggtcca cgacgagctg gtcctcgagg ccccaaaaga gagggcggag
2521 gccgtggccc ggctggccaa ggaggtcatg gagggggtgt atcccctggc cgtgcccctg
2581 gaggtggagg tgggggatagg ggaggactgg ctctccgcca aggagtgata gatctga
```

FIGURE 6

Nucleotide Sequence of Peptide-DSP-Taq Fusion Protein
(SEQ ID NO: 5)

```
   1 ACACAGGAAA CAGCGATGAT CGACCTGCAG CGGCCGCAGG CCGCCACCAT GGACTCTAGA
  61 CACCATCACC ATCACCACCC ATGGGATTAC AAGGACGACG ATGACAAGCC GCGGTGGAAT
 121 TCGAGCGCAA CCGTAAAGTT CAAGTACAAA GGCGAAGAAA AAGAGGTAGA CATCTCCAAG
 181 ATCAAGAAAG TATGGCGTGT GGGCAAGATG ATCTCCTTCA CCTACGACGA GGGCGGTGGC
 241 AAGACCGGCC GCGGTGCGGT AAGCGAAAAG GACGCGCCGA AGGAGCTGCT GCAGATGCTG
 301 GAGAAGCAGA AAAGATTAA GAATTCGGGT AACCTGCCCC TCTTTGAGCC CAAGGGCCGG
 361 GTCCTCCTGG TGGACGGCCA CCACCTGGCC TACCGCACCT TCCACGCCCT GAAGGGCCTC
 421 ACCACCAGCC GGGGGGAGCC GGTGCAGGCG GTCTACGGCT CGCCAAGAG CCTCCTCAAG
 481 GCCCTCAAGG AGGACGGGGA CGCGGTGATC GTGGTCTTTG ACGCCAAGGC CCCCTCCTTC
 541 CGCCACGAGG CCTACGGGGG GTACAAGGCG GGCCGGGCCC CCACACCGGA GGACTTTCCC
 601 CGGCAACTCG CCCTCATCAA GGAGCTGGTG GACCTCCTGG GGCTGGCGCG CCTCGAGGTC
 661 CCGGGCTACG AGGCGGACGA CGTCCTGGCC AGCCTGGCCA AGAAGGCGGA AAAGGAGGGC
 721 TACGAGGTCC GCATCCTCAC CGCCGACAAA GACCTTTACC AGCTCCTTTC CGACCGCATC
 781 CACGTCCTCC ACCCCGAGGG GTACCTCATC ACCCCGGCCT GGCTTTGGGA AAAGTACGGC
 841 CTGAGGCCCG ACCAGTGGGC CGACTACCGG GCCCTGACCG GGGACGAGTC CGACAACCTT
 901 CCCGGGGTCA AGGGCATCGG GGAGAAGACG GCGAGGAAGC TTCTGGAGGA GTGGGGGAGC
 961 CTGGAAGCCC TCCTCAAGAA CCTGGACCGG CTGAAGCCCG CCATCCGGGA GAAGATCCTG
1021 GCCCACATGG ACGATCTGAA GCTCTCCTGG GACCTGGCCA AGGTGCGCAC CGACCTGCCC
1081 CTGGAGGTGG ACTTCGCCAA AAGGCGGGAG CCCGACCGGG AGAGGCTTAG GGCCTTTCTG
1141 GAGAGGCTTG AGTTTGGCAG CCTCCTCCAC GAGTTCGGCC TTCTGGAAAG CCCCAAGGCC
1201 CTGGAGGAGG CCCCCTGGCC CCCGCCGGAA GGGGCCTTCG TGGGCTTTGT GCTTTCCCGC
1261 AAGGAGCCCA TGTGGGCCGA TCTTCTGGCC CTGGCCGCCG CCAGGGGGG CCGGGTCCAC
1321 CGGGCCCCCG AGCCTTATAA AGCCCTCAGG GACCTGAAGG AGGCGCGGGG GCTTCTCGCC
1381 AAAGACCTGA GCGTTCTGGC CCTGAGGGAA GGCCTTGGCC TCCCGCCCGG CGACGACCCC
1441 ATGCTCCTCG CCTACCTCCT GGACCCTTCC AACACCACCC CGAGGGGGT GGCCCGGCGC
1501 TACGGCGGGG AGTGGACGGA GGAGGCGGGG GAGCGGGCCG CCCTTTCCGA GAGGCTCTTC
1561 GCCAACCTGT GGGGGAGGCT TGAGGGGGAG GAGAGGCTCC TTTGGCTTTA CCGGGAGGTG
1621 GAGAGGCCCC TTTCCGCTGT CCTGGCCCAC ATGGAGGCCA CGGGGGTGCG CCTGGACGTG
1681 GCCTATCTCA GGGCCTTGTC CCTGGAGGTG GCCGAGGAGA TCGCCCGCCT CGAGGCCGAG
1741 GTCTTCCGCC TGGCCGGCCA CCCCTTCAAC CTCAACTCCC GGGACCAGCT GGAAAGGGTC
1801 CTCTTTGACG AGCTAGGGCT TCCCGCCATC GGCAAGACGG AGAAGACCGG CAAGCGCTCC
1861 ACCAGCGCCG CCGTCCTGGA GGCCCTCCGC GAGGCCCACC CCATCGTGGA AAGATCCTG
1921 CAGTACCGGG AGCTCACCAA GCTGAAGAGC ACCTACATTG ACCCCTTGCC GGACCTCATC
1981 CACCCCAGGA CGGGCCGCCT CCACACCCGC TTCAACCAGA CGGCCACGGC CACGGGCAGG
2041 CTAAGTAGCT CCGATCCCAA CCTCCAGAAC ATCCCCGTCC GCACCCCGCT GGGCAGAGG
2101 ATCCGCCGGG CCTTCATCGC CGAGGAGGGG TGGCTATTGG TGGCCCTGGA CTATAGCCAG
2161 ATAGAGCTCA GGGTGCTGGC CCACCTCTCC GGCGACGAGA ACCTGATCCG GGTCTTCCAG
2221 GAGGGGCGGG ACATCCACAC GGAGACCGCC AGCTGGATGT CGGCGTCCC CGGGAGGCC
2281 GTGGACCCCC TGATGCGCCG GGCGGCCAAG ACCATCAACT TCGGGGTCCT CTACGGCATG
2341 TCGGCCCACC GCCTCTCCCA GGAGCTAGCC ATCCCTTACG AGGAGGCCCA GGCCTTCATT
2401 GAGCGCTACT TTCAGAGCTT CCCCAAGGTG CGGGCCTGGA TTGAGAAGAC CCTGGAGGAG
2461 GGCAGGAGGC GGGGGTACGT GGAGACCCTC TTCGGCCGCC GCCGCTACGT GCCAGACCTA
2521 GAGGCCCGGG TGAAGAGCGT GCGGGAGGCG GCCGAGCGCA TGGCCTTCAA CATGCCCGTC
2581 CAGGGCACCG CCGCCGACCT CATGAAGCTG GCTATGGTGA AGCTCTTCCC CAGGCTGGAG
2641 GAAATGGGGG CCAGGATGCT CCTTCAGGTC CACGACGAGC TGGTCCTCGA GGCCCCAAAA
2701 GAGAGGGCGG AGGCCGTGGC CCGGCTGGCC AAGGAGGTCA TGGAGGGGGT GTATCCCCTG
2761 GCCGTGCCCC TGGAGGTGGA GGTGGGGATA GGGGAGGACT GGCTCTCCGC CAAGGAGTGA
2821 TAGATCTGA
```

FIGURE 7

Amino Acid Sequence of Peptide-DSP-Taq Fusion Protein
(SEQ ID NO: 6)

```
  1 MIDLQRPQAA TMDSRHHHHH HPWDYKDDDD KPRWNSSATV KFKYKGEEKE VDISKIKKVW
 61 RVGKMISFTY DEGGGKTGRG AVSEKDAPKE LLQMLEKQKK IKNSGNLPLF EPKGRVLLVD
121 GHHLAYRTFH ALKGLTTSRG EPVQAVYGFA KSLLKALKED GDAVIVVFDA KAPSFRHEAY
181 GGYKAGRAPT PEDFPRQLAL IKELVDLLGL ARLEVPGYEA DDVLASLAKK AEKEGYEVRI
241 LTADKDLYQL LSDRIHVLHP EGYLITPAWL WEKYGLRPDQ WADYRALTGD ESDNLPGVKG
301 IGEKTARKLL EEWGSLEALL KNLDRLKPAI REKILAHMDD LKLSWDLAKV RTDLPLEVDF
361 AKRREPDRER LRAFLERLEF GSLLHEFGLL ESPKALEEAP WPPPEGAFVG FVLSRKEPMW
421 ADLLALAAAR GGRVHRAPEP YKALRDLKEA RGLLAKDLSV LALREGLGLP PGDDPMLLAY
481 LLDPSNTTPE GVARRYGGEW TEEAGERAAL SERLFANLWG RLEGEERLLW LYREVERPLS
541 AVLAHMEATG VRLDVAYLRA LSLEVAEEIA RLEAEVFRLA GHPFNLNSRD QLERVLFDEL
601 GLPAIGKTEK TGKRSTSAAV LEALREAHPI VEKILQYREL TKLKSTYIDP LPDLIHPRTG
661 RLHTRFNQTA TATGRLSSSD PNLQNIPVRT PLGQRIRRAF IAEEGWLLVA LDYSQIELRV
721 LAHLSGDENL IRVFQEGRDI HTETASWMFG VPREAVDPLM RRAAKTINFG VLYGMSAHRL
781 SQELAIPYEE AQAFIERYFQ SFPKVRAWIE KTLEEGRRRG YVETLFGRRR YVPDLEARVK
841 SVREAAERMA FNMPVQGTAA DLMKLAMVKL FPRLEEMGAR MLLQVHDELV LEAPKERAEA
901 VARLAKEVME GVYPLAVPLE VEVGIGEDWL SAKE**I*
```

FIGURE 8

Nucleotide Sequence of Peptide-DSP Tag
(SEQ ID NO: 7)

```
  1 ATGATCGACC TGCAGCGGCC GCAGGCCGCC ACCATGGACT CTAGACACCA TCACCATCAC
 61 CACCCATGGG ATTACAAGGA CGACGATGAC AAGCCGCGGT GGAATTCGAG CGCAACCGTA
121 AAGTTCAAGT ACAAAGGCGA AGAAAAAGAG GTAGACATCT CCAAGATCAA GAAAGTATGG
181 CGTGTGGGCA AGATGATCTC CTTCACCTAC GACGAGGGCG GTGGCAAGAC CGGCCGCGGT
241 GCGGTAAGCG AAAAGGACGC GCCGAAGGAG CTGCTGCAGA TGCTGGAGAA GCAGAAAAAG
301 ATTAAGAATT CGGGTAACCT GCCCC
```

FIGURE 9

Amino Acid Sequence of Peptide-DSP Tag
(SEQ ID NO: 8)

```
 1 MIDLQRPQAA TMDSRHHHHH HPWDYKDDDD KPRWNSSATV KFKYKGEEKE VDISKIKKVW
61 RVGKMISFTY DEGGGKTGRG AVSEKDAPKE LLQMLEKQKK IKNSGN
```

FIGURE 10

Nucleotide Sequence of DSP Tag
(SEQ ID NO: 9)

```
  1 AGCGCAACCG TAAAGTTCAA GTACAAAGGC GAAGAAAAAG AGGTAGACAT CTCCAAGATC
 61 AAGAAAGTAT GGCGTGTGGG CAAGATGATC TCCTTCACCT ACGACGAGGG CGGTGGCAAG
121 ACCGGCCGCG GTGCGGTAAG CGAAAAGGAC GCGCCGAAGG AGCTGCTGCA GATGCTGGAG
181 AAGCAGAAAA AGATTAAGAA TTCG
```

FIGURE 11

Amino Acid Sequence of DSP Tag
(SEQ ID NO: 10)

```
 1 SATVKFKYKG EEKEVDISKI KKVWRVGKMI SFTYDEGGGK TGRGAVSEKD APKELLQMLE
61 KQKKIKNS
```

FIGURE 12

Amino Acid Sequence of Peptide-TGO-DSP fusion protein
(SEQ ID NO: 11)

```
  1 MIDLQRPQAA TMDSRHHHHH HPWDYKDDDD KPRWNSILDT DYITEDGKPV IRIFKKENGE
 61 FKIDYDRNFE PYIYALLKDD SAIEDVKKIT AERHGTTVRV VRAEKVKKKF LGRPIEVWKL
121 YFTHPQDVPA IRDKIKEHPA VVDIYEYDIP FAKRYLIDKG LIPMEGDEEL KMLAFDIETL
181 YHEGEEFAEG PILMISYADE EGARVITWKN IDLPYVDVVS TEKEMIKRFL KVVKEKDPDV
241 LITYNGDNFD FAYLKKRSEK LGVKFILGRE GSEPKIQRMG DRFAVEVKGR IHFDLYPVIR
301 RTINLPTYTL EAVYEAIFGQ PKEKVYAEEI AQAWETGEGL ERVARYSMED AKVTYELGKE
361 FFPMEAQLSR LVGQSLWDVS RSSTGNLVEW FLLRKAYERN ELAPNKPDER ELARRRESYA
421 GGYVKEPERG LWENIVYLDF RSLYPSIIIT HNVSPDTLNR EGCEEYDVAP QVGHKFCKDF
481 PGFIPSLLGD LLEERQKVKK KMKATIDPIE KKLLDYRQRA IKILANSFYG YYGYAKARWY
541 CKECAESVTA WGRQYIETTI REIEEKFGFK VLYADTDGFF ATIPGADAET VKKKAKEFLD
601 YINAKLPGLL ELEYEGFYKR GFFVTKKKYA VIDEEDKITT RGLEIVRRDW SEIAKETQAR
661 VLEAILKHGD VEEAVRIVKE VTEKLSKYEV PPEKLVIYEQ ITRDLKDYKA TGPHVAVAKR
721 LAARGIKIRP GTVISYIVLK GSGRIGDRAI PFDEFDPAKH KYNAEYYIEN QVLPAVERIL
781 RAFGYRKEDL RYQKTRQVGL GAWLKPKTSW ICATVKFKYK GEEKEVDISK IKKVWRVGKM
841 ISFTYDEGGG KTGRGAVSEK DAPKELLQML EKQKKI
```

FIGURE 13

Nucleic Acid sequence encoding Peptide-TGO-DSP Fusion Protein
(SEQ ID NO: 12)

```
   1 ATGATCGACC TGCAGCGGCC GCAGGCCGCC ACCATGGACT CTAGACACCA TCACCATCAC
  61 CACCCATGGG ATTACAAGGA CGACGATGAC AAGCCGCGGT GGAATTCCAT CCTCGATACA
 121 GACTACATAA CTGAGGATGG AAAGCCCGTC ATCAGGATCT TCAAGAAGGA GAACGGCGAG
 181 TTCAAAATAG ACTACGACAG AAACTTTGAG CCATACATCT ACGCGCTCTT GAAGGACGAC
 241 TCTGCGATTG AGGACGTCAA GAAGATAACT GCCGAGAGGC ACGGCACTAC CGTTAGGGTT
 301 GTCAGGGCCG AGAAAGTGAA GAAGAAGTTC CTAGGCAGGC CGATAGAGGT CTGGAAGCTC
 361 TACTTCACTC ACCCCCAGGA CGTTCCCGCA ATCAGGGACA AGATAAAGGA GCATCCTGCC
 421 GTTGTGGACA TCTACGAGTA CGACATCCCC TTCGCGAAGC GCTACCTCAT AGACAAAGGC
 481 TTAATCCCGA TGGAGGGCGA CGAGGAACTT AAGATGCTCG CCTTCGACAT CGAGACGCTC
 541 TATCACGAGG GCGAGGAGTT CGCCGAAGGG CCTATCCTGA TGATAAGCTA CGCCGACGAG
 601 GAAGGGCGC GCGTTATTAC CTGGAAGAAT ATCGACCTTC CCTATGTCGA CGTCGTTTCC
 661 ACCGAGAAGG AGATGATAAA GCGCTTCCTC AAGGTCGTCA AGGAAAAGGA TCCCGACGTC
 721 CTCATAACCT ACAACGGCGA CAACTTCGAC TTCGCCTACC TCAAGAAGCG CTCCGAGAAG
 781 CTCGGAGTCA AGTTCATCCT CGGAAGGGAA GGGAGCGAGC CGAAAATCCA GCGCATGGGC
 841 GATCGCTTTG CGGTGGAGGT CAAGGGAAGG ATTCACTTCG ACCTCTACCC CGTCATTAGG
 901 AGAACGATTA ACCTCCCCAC TTACACCCTT GAGGCAGTAT ATGAAGCCAT CTTTGGACAG
 961 CCGAAGGAGA AGGTCTACGC TGAGGAGATA GCGCAGGCCT GGGAAACGGG CGAGGGATTA
1021 GAAAGGGTGG CCCGCTACTC GATGGAGGAC GCAAAGGTAA CCTATGAACT CGGAAAAGAG
1081 TTCTTCCCTA TGGAAGCCCA GCTCTCGCGC CTCGTAGGCC AGAGCCTCTG GGATGTATCT
1141 CGCTCGAGTA CCGGAAACCT CGTCGAGTGG TTTTTGCTGA GGAAGGCCTA CGAGAGGAAT
1201 GAACTTGCAC CAAACAAGCC GGACGAGAGG GAGCTGGCAA GAAGAAGGGA GAGCTACGCG
1261 GGTGGATACG TCAAGGAGCC CGAAAGGGGA CTGTGGGAGA ACATCGTGTA TCTGGACTTC
1321 CGCTCCCTGT ATCCTTCGAT AATAATCACC CATAACGTCT CCCCTGATAC ACTCAACAGG
1381 GAGGGTTGTG AGGAGTACGA CGTGGCTCCT CAGGTAGGCC ATAAGTTCTG CAAGGACTTC
1441 CCCGGCTTCA TCCCAAGCCT CCTCGGGGAC CTCTTGGAGG AGAGACAGAA GGTAAAGAAG
1501 AAGATGAAGG CCACTATAGA CCCAATCGAG AAGAAACTCC TCGATTACAG CAGCGAGCA
1561 ATCAAAATCC TTGCTAATAG CTTCTACGGT TACTACGGCT ATGCAAAGGC CCGCTGGTAC
1621 TGCAAGGAGT GCGCCGAGAG CGTTACCGCT TGGGGCAGGC AGTACATCGA GACCACGATA
1681 AGGGAAATAG AGGAGAAATT TGGCTTTAAA GTCCTCTACG CGGACACAGA TGGATTTTTC
1741 GCAACAATAC CTGGAGCGGA CGCCGAAACC GTCAAAAAGA AGGCAAAGGA GTTCCTGGAC
1801 TACATCAACG CCAAACTGCC CGGCCTGCTC GAACTCGAAT ACGAGGGCTT CTACAAGCGC
1861 GGCTTCTTCG TGACGAAGAA GAAGTACGCG GTTATAGACG AGGAGGACAA GATAACGACG
1921 CGCGGGCTTG AAATAGTTAG GCGTGACTGG AGCGAGATAG CGAAGGAGAC GCAGGCGAGG
1981 GTTCTTGAGG CGATACTAAA GCACGGTGAC GTTGAAGAAG CGGTAAGGAT TGTCAAAGAG
2041 GTTACGGAGA AGCTGAGCAA GTACGAGGTT CCACCGGAGA AGCTGGTCAT CTACGAGCAG
2101 ATAACCCGCG ACCTGAAGGA CTACAAGGCC ACCGGGCCGC ATGTGGCTGT TGCAAAACGC
2161 CTCGCCGCAA GGGGGATAAA AATCCGGCCC GGAACGGTCA TAAGCTACAT CGTGCTCAAA
2221 GGCTCGGGAA GGATTGGGGA CAGGGCTATA CCCTTTGACG AATTTGACCC GGCAAAGCAC
2281 AAGTACAATG CAGAATACTA CATCGAGAAC CAGGTTCTTC CAGCTGTGGA GAGGATTCTG
2341 AGGGCCTTTG GTTACCGTAA AGAAGATTTA AGGTATCAGA AACGCGGCA GGTTGGCTTG
2401 GGGGCGTGGC TAAAACCTAA GACAAGCTGG ATCTGCGCAA CCGTAAAGTT CAAGTACAAA
2461 GGCGAAGAAA AGAGGTAGA CATCTCCAAG ATCAAGAAAG TATGGCGTGT GGGCAAGATG
2521 ATCTCCTTCA CCTACGACGA GGGCGGTGGC AAGACCGGCC GCGGTGCGGT AAGCGAAAAG
2581 GACGCGCCGA AGGAGCTGCT GCAGATGCTG GAGAAGCAGA AAAAGATTTA GTGG
```

FIGURE 14

Amino Acid Sequence of Short Peptide
(SEQ ID NO: 13)

MVDDLQRPH HHHHHPWDYK DDDDKPRWNS GW

FIGURE 16

Amino Acid Sequence of Peptide Tag
(SEQ ID NO: 14)

1 MIDLQRPQAA TMDSRHHHHH HPWDYKDDDD KPRWNS

FIGURE 17

Nucleic Acid sequence encoding Peptide Tag
(SEQ ID NO: 15)

```
 1 ATGATCGACC TGCAGCGGCC GCAGGCCGCC ACCATGGACT CTAGACACCA TCACCATCAC
61 CACCCATGGG ATTACAAGGA CGACGATGAC AAGCCGCGGT GGAATTCC
```

FIGURE 18

Amino Acid Sequence of Peptide Tag
(SEQ ID NO: 16)

1 MIDLQRPSAA TMVDDLQRPH HHHHHPWDYK DDDDKPRWNS

FIGURE 19

Nucleic Acid sequence encoding Peptide Tag
(SEQ ID NO: 17)

```
 1 ATGATCGACC TGCAGCGGCC ATCCGCCGCC ACCATGGTCG ACGACCTGCA GCGGCCGCAC
61 CATCACCATC ACCATCCATG GGATTACAAG GACGACGATG ACAAGCCGCG GTGGAATTCG
```

FIGURE 20

Amino Acid Sequence of Peptide Tag
(SEQ ID NO: 18)

1 MVDDLQRPHH HHHHPWDYKD DDDKPRWNS

FIGURE 21

Nucleic Acid sequence encoding Peptide Tag
(SEQ ID NO: 19)

```
 1 ATGGTCGACG ACCTGCAGCG GCCGCACCAT CACCATCACC ATCCATGGGA TTACAAGGAC
61 GACGATGACA AGCCGCGGTG GAATTCG
```

FIGURE 22

Amino Acid Sequence of Peptide Tag-hEPO (human erythropoietin)
(SEQ ID NO: 20)

```
  1 MIDLQRPSAA TMVDDLQRPH HHHHHPWDYK DDDDKPRWNS GAPPRLICDS RVLERYLLEA
 61 KEAENITTGC AEHCSLNENI TVPDTKVNFY AWKRMEVGQQ AVEVWQGLAL LSEAVLRGQA
121 LLVNSSQPWE PLQLHVDKAV SGLRSLTTLL RALGAQKEAI SPPDAASAAP LRTITADTFR
181 KLFRVYSNFL RGKLKLYTGE ACRTGDR
```

FIGURE 23

Nucleic Acid sequence encoding Peptide Tag-hEPO
(SEQ ID NO: 21)

```
  1 ATGATCGACC TGCAGCGGCC ATCCGCCGCC ACCATGGTCG ACGACCTGCA GCGGCCGCAC
 61 CATCACCATC ACCATCCATG GGATTACAAG GACGACGATG ACAAGCCGCG GTGGAATTCG
121 GGGGCCCCAC CACGCCTCAT CTGTGACAGC CGAGTCCTGG AGAGGTACCT CTTGGAGGCC
181 AAGGAGGCCG AGAATATCAC GACGGGCTGT GCTGAACACT GCAGCTTGAA TGAGAATATC
241 ACTGTCCCAG ACACCAAAGT TAATTTCTAT GCCTGGAAGA GGATGGAGGT CGGGCAGCAG
301 GCCGTAGAAG TCTGGCAGGG CCTGGCCCTG CTGTCGGAAG CTGTCCTGCG GGGCCAGGCC
361 CTGTTGGTCA ACTCTTCCCA GCCGTGGGAG CCCCTGCAGC TGCATGTGGA TAAAGCCGTC
421 AGTGGCCTTC GCAGCCTCAC CACTCTGCTT CGGGCTCTGG GAGCCCAGAA GGAAGCCATC
481 TCCCCTCCAG ATGCGGCCTC AGCTGCTCCA CTCCGAACAA TCACTGCTGA CACTTTCCGC
541 AAACTCTTCC GAGTCTACTC CAATTTCCTC CGGGGAAAGC TGAAGCTGTA CACAGGGGAG
601 GCCTGCAGGA CAGGGACAG A
```

FIGURE 24

Amino Acid Sequence of Peptide Tag-hLIF (human leukemia inhibitory factor)
(SEQ ID NO: 22)

```
  1 MIDLQRPSAA TMVDDLQRPH HHHHHPWDYK DDDDKPRWNS KVLAAGVVPL LLVLHWKHGA
 61 GSPLPITPVN ATCAIRHPCH NNLMNQIRSQ LAQLNGSANA LFILYYTAQG EPFPNNLDKL
121 CGPNVTDFPP FHANGTEKAK LVELYRIVVY LGTSLGNITR DQKILNPSAL SLHSKLNATA
181 DILRGLLSNV LCRLCSKYHV GHVDVTYGPD TSGKDVFQKK KLGCQLLGKY KQIIAVLAQA
241 F
```

FIGURE 25

Nucleic Acid sequence encoding Peptide Tag-hLIF
(SEQ ID NO: 23)

```
  1 ATGATCGACC TGCAGCGGCC ATCCGCCGCC ACCATGGTCG ACGACCTGCA GCGGCCGCAC
 61 CATCACCATC ACCATCCATG GGATTACAAG GACGACGATG ACAAGCCGCG GTGGAATTCG
121 AAAGTGCTGG CGGCGGGCGT GGTGCCGCTG CTGCTGGTGC TGCATTGGAA ACATGGCGCG
181 GGCAGCCCGC TGCCGATTAC CCCGGTGAAC GCGACCTGCG CGATTCGCCA TCCGTGCCAT
241 AACAACCTGA TGAACCAGAT TCGCAGCCAG CTGGCGCAGC TGAACGGCAG CGCGAACGCG
301 CTGTTTATTC TGTATTATAC CGCGCAGGGC GAACCGTTTC GAACAACCT GGATAAACTG
361 TGCGGCCCGA ACGTGACCGA TTTTCCGCCG TTTCATGCGA ACGGCACCGA AAAAGCGAAA
421 CTGGTGGAAC TGTATCGCAT TGTGGTGTAT CTGGGCACCA GCCTGGGCAA CATTACCCGC
481 GATCAGAAAA TTCTGAACCC GAGCGCGCTG AGCCTGCATA GCAAACTGAA CGCGACCGCG
541 GATATTCTGC GCGGCCTGCT GAGCAACGTG CTGTGCCGCC TGTGCAGCAA ATATCATGTG
601 GGCCATGTGG ATGTGACCTA TGGCCCGGAT ACCAGCGGCA AGATGTGTT TCAGAAAAAA
661 AAACTGGGCT GCCAGCTGCT GGGCAAATAT AAACAGATTA TTGCGGTGCT GGCGCAGGCG
721 TTT
```

COMPOSITIONS FOR INCREASING POLYPEPTIDE STABILITY AND ACTIVITY, AND RELATED METHODS

CROSS-REFERENCE TO RELATED APPLICATIONS

This application claims the benefit under 35 U.S.C. §119 (e) of U.S. Provisional Application No. 61/262,919, filed Nov. 19, 2009; U.S. Provisional Application No. 61/350,457, filed Jun. 1, 2010; U.S. Provisional Application No. 61/356,541, filed Jun. 18, 2010; and U.S. Provisional Application No. 61/390,857, filed Oct. 7, 2010, all of which are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on Dec. 21, 2010, is named 39328701.txt and is 75,509 bytes in size.

BACKGROUND OF THE INVENTION

There is a need in the art for methods and compositions that enhance the stability of proteins. There is particularly a need for compositions that enhance the stability of polymerases such as Taq polymerases so that they can retain enzymatic activity after short-term or long-term exposure to temperatures above freezing. There is also a need in the art for compositions that enhance polymerase fidelity, sensitivity, and yield.

SUMMARY OF THE INVENTION

This disclosure provides peptides, polypeptides, fusion polypeptides, compositions, and methods for enabling the retention of activity of an enzyme (e.g., DNA polymerase, RNA polymerase, nuclease, reverse transcriptase, DNA deaminase, RNA deaminase, protease) or a protein (e.g., erythropoietin, human Leukemia Inhibitor Factor (hLIF), granulocyte macrophage colony-stimulating factor (GM-CSF), insulin, vascular endothelial growth factor (VEGF), leptin, bevacizumab) after short-term or long-term exposure to a temperature of from about −20° C. to about 35° C. In some embodiments, peptides, polypeptides, fusion polypeptides, or compositions provided herein enhance stability of an enzyme or protein at room temperature. In some embodiments, an enzyme or protein provided herein is any nucleic acid binding protein, e.g., a DNA binding protein, a RNA binding protein, a fragment thereof, or any combination thereof. In some embodiments, an enzyme or protein provided herein binds to other proteins, e.g., hormone receptors.

In some embodiments, polypeptides, fusion polypeptides, or compositions provided herein retain activity at a temperature between −20° C. and 50° C. In some embodiments, polypeptides, fusion polypeptides, or compositions retain enzymatic activity or hormone activity at a temperature between −20° C. and 50° C. In some embodiments, the enzymatic activity or hormone activity of the polypeptides, fusion polypeptides, or compositions after exposure to a temperature between −20° C. and 50° C. is at least 50% of the enzymatic activity of the polypeptide prior to exposure to said temperature.

In some embodiments, peptide tags provided herein increase stability of the polypeptides, fusion polypeptides, or compositions. In some embodiments, peptide tags stabilize the polypeptides, fusion polypeptides, or compositions. In some embodiments, peptide tags inhibit loss of enzymatic activity of the polypeptides, fusion polypeptides, or compositions. In some embodiments, peptide tags inhibit degradation of the polypeptides, fusion polypeptides, or compositions. In some embodiments, peptide tags increase stability or inhibit loss of enzymatic activity of the polypeptides, fusion polypeptides, or compositions for at least one day. In some embodiments, peptide tags increase stability or inhibit loss of enzymatic activity of the polypeptides, fusion polypeptides, or compositions for at least one week. In some embodiments, peptide tags increase stability or inhibit loss of enzymatic activity of the polypeptides, fusion polypeptides, or compositions for at least one month.

In some embodiments, polypeptides, fusion polypeptides, or compositions provided herein demonstrate enhanced stability, enzymatic activity, or hormone activity when compared to a similar polypeptide that does not comprise a peptide tag provided herein. In some embodiments, polypeptides, fusion polypeptides, or compositions have at least 50%, 60%, 70%, 80%, 90%, or 95% of the enzymatic activity or hormone activity of a similar polypeptide that does not comprise a peptide tag provided herein. In some embodiments, polypeptides, fusion polypeptides, or compositions have at least 50%, 60%, 70%, 80%, 90%, or 95% of the enzymatic activity or hormone activity of a similar polypeptide that does not comprise a peptide tag provided herein, after exposure to a temperature between −20° C. and 50° C. In some embodiments, polypeptides, fusion polypeptides, or compositions have at least 5%, 10%, 15%, 20%, 25%, 30%, 40%, 50%, 60%, 70%, 80%, 90%, 100%, or 200% greater enzymatic activity or hormone activity than the enzymatic activity or hormone activity of a similar polypeptide that does not comprise a peptide tag provided herein, after exposure to a temperature between −20° C. and 50° C.

In some embodiments, polypeptides, fusion polypeptides, or compositions provided herein comprise a peptide tag that has an amino acid sequence that is at least 70% identical to SEQ ID NO: 1. In some embodiments, polypeptides, fusion polypeptides, or compositions provided herein comprise a peptide tag that has an amino acid sequence that is 50% to 98% identical to SEQ ID NO: 1. In some embodiments, the peptide tag has an amino acid sequence as shown in SEQ ID NO: 1, SEQ ID NO: 13, or SEQ ID NO: 14. In some embodiments, the peptide tag has an amino acid sequence that is at least 70% identical to SEQ ID NO: 13 or SEQ ID NO: 14. In some embodiments, polypeptides, fusion polypeptides, or compositions provided herein comprise an amino acid sequence that is at least 70% identical to SEQ ID NO: 6, SEQ ID NO: 8, or SEQ ID NO: 11. In some embodiments, polypeptides, fusion polypeptides, or compositions provided herein comprise an amino acid sequence as shown in SEQ ID NO: 6, SEQ ID NO: 8, or SEQ ID NO: 11. In some embodiments, the fusion polypeptide comprises an amino acid sequence that is at least 70% identical to SEQ ID NO: 1, SEQ ID NO: 6, SEQ ID NO: 8, SEQ ID NO: 11, SEQ ID NO: 13, SEQ ID NO: 14, SEQ ID NO: 16, SEQ ID NO: 18, SEQ ID NO: 20, SEQ ID NO: 22. In some embodiments, polypeptides, fusion polypeptides, or compositions do not have the amino acid sequence as shown in SEQ ID NO: 2, SEQ ID NO: 6, or SEQ ID NO: 11.

In some embodiments, polypeptides, fusion polypeptides, or compositions provided herein comprise a peptide tag that is encoded by a nucleotide sequence that is at least 70% identical to SEQ ID NO: 3 or SEQ ID NO: 15. In some embodiments, polypeptides, fusion polypeptides, or compositions provided herein comprise a peptide tag that is encoded by a nucleotide sequence as shown in SEQ ID NO:3 or SEQ ID NO: 15. In some embodiments, polypeptides, fusion polypeptides, or compositions provided herein comprise a polypeptide encoded by a nucleotide sequence that is at least 70% identical to SEQ ID NO: 4, SEQ ID NO: 5, SEQ ID NO: 7, or SEQ ID NO: 12. In some embodiments, polypeptides, fusion polypeptides, or compositions provided herein comprise a polypeptide encoded by a nucleotide sequence as shown in SEQ ID NO: 4, SEQ ID NO: 5, SEQ ID NO: 7, or SEQ ID NO: 12.

In some embodiments, polypeptides, fusion polypeptides, or compositions provided herein comprise a polypeptide that has an amino acid sequence that is at least 70% identical to SEQ ID NO: 10. In some embodiments, polypeptides, fusion polypeptides, or compositions comprise a polypeptide that has an amino acid sequence as shown in SEQ ID NO: 10. In some embodiments, polypeptides, fusion polypeptides, or compositions comprise a polypeptide comprising a sequence motif that binds to a double stranded DNA. In some embodiments, polypeptides, fusion polypeptides, or compositions comprise a polypeptide that is encoded by a nucleotide sequence that is at least 70% identical to SEQ ID NO: 9. In some embodiments, polypeptides, fusion polypeptides, or compositions comprise a polypeptide that is encoded by a nucleotide sequence as shown in SEQ ID NO: 9. In some embodiments, the fusion polypeptide comprises a polypeptide encoded by SEQ ID NO: 3, SEQ ID NO: 5, SEQ ID NO: 7, SEQ ID NO: 12, SEQ ID NO: 15, SEQ ID NO: 17, SEQ ID NO: 19, SEQ ID NO: 21, or SEQ ID NO: 23.

In some embodiments, fusion polypeptides provided herein comprise a peptide tag that has an amino acid sequence that is 50% to 98% identical to SEQ ID NO: 1 and at least one polypeptide, wherein the peptide tag is linked to said at least one polypeptide, and the peptide tag stabilizes the fusion polypeptide at a temperature between −20° C. and 50° C. In one embodiment, the peptide tag is covalently linked to the at least one polypeptide. In one embodiment, the peptide tag is non-covalently linked to the at least one polypeptide. In one embodiment, the peptide tag is linked to the amino-terminus of the at least one polypeptide. In one embodiment, the peptide tag is linked to the carboxy-terminus of the at least one polypeptide. In some embodiments, the fusion polypeptide comprises a first polypeptide and a second polypeptide. In one embodiment, the first polypeptide is an enzyme and the second polypeptide is a double strand binding protein. In one embodiment, the peptide tag is linked to the amino-terminus of the first polypeptide, and the carboxy-terminus of the first polypeptide is linked to the amino-terminus of the second polypeptide. In one embodiment, the peptide tag is linked to the amino-terminus of the second polypeptide, and the carboxy-terminus of the second polypeptide is linked to the amino-terminus of the first polypeptide.

In one aspect, this disclosure provides a polypeptide, fusion polypeptide, or composition comprising a peptide tag linked to a polypeptide, wherein said polypeptide retains an enzymatic activity after exposure to a temperature of at least about −10° C. to about 50° C., and wherein said fusion polypeptide does not have the amino acid sequence of SEQ ID NO: 2.

In another aspect, this disclosure provides a composition comprising: (a) a fusion polypeptide comprising a first polypeptide linked to a peptide, wherein said fusion polypeptide retains an enzymatic activity after exposure to a temperature of at least about −10° C. to about 50° C.; and (b) a second polypeptide.

In some embodiments, the peptide is covalently linked to said polypeptide, said first polypeptide or said second polypeptide. In some embodiments, the peptide is non-covalently linked to polypeptide, said first polypeptide or said second polypeptide. In some embodiments, the peptide is linked to said polypeptide, said first polypeptide or said second polypeptide at the amino-terminus of said polypeptide, said first polypeptide or said second polypeptide. In some embodiments, said peptide is linked to said polypeptide, said first polypeptide or said second polypeptide at the carboxy-terminus of said polypeptide, said first polypeptide or said second polypeptide. In some embodiments, polypeptide, first polypeptide, or second polypeptide is a thermostable protein. In some embodiments, said thermostable protein is an enzyme. In some embodiments, said enzyme is a polymerase, a reverse transcriptase, a nuclease, a pyrophosphatase, a protease, or a deaminase. In some embodiments, said fusion polypeptide is a polypeptide encoded by SEQ ID NO: 4. In some embodiments, said fusion polypeptide is at least 70% identical to a polypeptide encoded by SEQ ID NO: 4, SEQ ID NO: 5, or SEQ ID NO: 12. In some embodiments, said peptide is at least 70% identical to SEQ ID NO: 1.

In some embodiments, provided herein are compositions comprising a fusion polypeptide comprising a peptide tag linked to a first polypeptide, and a second polypeptide, wherein the peptide tag stabilizes said first polypeptide or said second polypeptide at a temperature between −20° C. and 50° C. In one embodiment, the peptide tag stabilizes the first polypeptide or the second polypeptide for at least 1 day in a temperature between −20° C. and 50° C. In one embodiment, the fusion polypeptide or the second polypeptide retains enzymatic activity or hormone activity at a temperature between −20° C. and 50° C. In one embodiment, the enzymatic activity or hormone activity of the fusion polypeptide or the second polypeptide after exposure to a temperature between −20° C. and 50° C. is at least 50% of the enzymatic activity or hormone activity of the fusion polypeptide or the second polypeptide prior to exposure to said temperature. In one embodiment, the first polypeptide or the second polypeptide is a polymerase, reverse transcriptase, nuclease, pyrophosphatase, deaminase, or protease. In one embodiment, the first polypeptide or the second polypeptide is erythropoietin, human Leukemia Inhibitor Factor (hLIF), granulocyte macrophage colony-stimulating factor (GM-CSF), insulin, vascular endothelial growth factor (VEGF), leptin, or bevacizumab. In one embodiment, the first polypeptide or the second polypeptide comprises at least one mutation. In one embodiment, the fusion polypeptide comprises a polypeptide that has an amino acid sequence that is at least 70% identical to SEQ ID NO: 1, SEQ ID NO: 6, SEQ ID NO: 8, SEQ ID NO: 11, SEQ ID NO: 13, SEQ ID NO: 14, SEQ ID NO: 16, SEQ ID NO: 18, SEQ ID NO: 20, or SEQ ID NO: 22. In one embodiment, the fusion polypeptide comprises a polypeptide encoded by SEQ ID NO: 3, SEQ ID NO: 5, SEQ ID NO: 7, SEQ ID NO: 12, SEQ ID NO: 15, SEQ ID NO: 17, SEQ ID NO: 19, SEQ ID NO: 21, or SEQ ID NO: 23.

In some embodiments, compositions provided herein further comprise a third polypeptide. In one embodiment, the fusion polypeptide has a sequence as shown in SEQ ID NO: 2, the second polypeptide has a sequence as shown in SEQ ID NO: 6, and the third polypeptide has a sequence as shown in SEQ ID NO: 11.

In some embodiments, said second polypeptide is a polymerase. In some embodiments, said second polypeptide is at least 70% identical to a polypeptide encoded by SEQ ID NO: 5 or SEQ ID NO: 12. In some embodiments, said second polypeptide is at least 70% identical to a polypeptide encoded by SEQ ID NO: 4. In some embodiments, said fusion polypeptide comprises an enzyme or polymerase and said peptide has at least 70% identity to a peptide encoded by SEQ ID NO: 3, SEQ ID NO: 7, or SEQ ID NO: 9. In some embodiments, said polypeptide, first polypeptide, or second polypeptide is selected from the group consisting of: DNA polymerase I, *Thermus aquaticus* DNA polymerase I (Taq), and *Thermococcus gorgonarius* DNA polymerase (Tgo). In some embodiments, said polypeptide, first polypeptide, or second polypeptide is erythropoietin. In some embodiments, said polypeptide, first polypeptide or second polypeptide is a Taq polymerase. In some embodiments, said polypeptide, first polypeptide or second polypeptide is a Tgo polymerase, or 70% identical to Tgo polymerase. In some embodiments, said polypeptide, first polypeptide or second polypeptide is a Taq polymerase. In some embodiments, said polypeptide, first polypeptide, or second polypeptide is selected from the group consisting of: *Thermoplasma acidophilum* pyrophosphatase (TAPP), *Pyrococcus horikoshii* dCTP deaminase, cytidine deaminase and a deoxycytidine deaminase. In some embodiments, the deaminase is a RNA deaminase or a DNA deaminase. In some embodiments, said polypeptide, first polypeptide, or second polypeptide is a non-thermostable protein. In some embodiments, said non-thermostable protein is human Leukemia Inhibitor Factor (hLIF) or leptin. In some embodiments, said temperature is about 20° C. to about 30° C.

In some embodiments, the exposure to the temperature is for at least 1 week. In some embodiments, said enzymatic activity is greater than about 50% of the activity of the enzyme prior to exposure to a temperature of at least about −20° C. to about 35° C. In some embodiments, said peptide has an amino acid sequence with at least 70%, 75%, 80%, 85%, 90%, or 95% identity to the sequence of SEQ ID NO: 1, SEQ ID NO: 8, SEQ ID NO: 10, or SEQ ID NO: 13. In some embodiments, said fusion polypeptide has an amino acid sequence that is at least 70% identical to SEQ ID NO: 2. In some embodiments, the peptide is at least 70% identical to a peptide encoded by a nucleotide sequence that is SEQ ID NO: 3, SEQ ID NO: 7, or SEQ ID NO: 9. In some embodiments, the peptide-linked polypeptide is at least 70% identical to a polypeptide encoded by a nucleotide sequence that is SEQ ID NO: 5 or SEQ ID NO: 12. In some embodiments, the peptide-linked polypeptide is at least 70% identical to a polypeptide encoded by a nucleotide sequence that is SEQ ID NO: 4, SEQ ID NO: 5, or SEQ ID NO: 12.

In yet another aspect, the disclosure provides a polypeptide, fusion polypeptide, or composition comprising a peptide with an amino acid sequence that is at least 70% homologous to SEQ ID NO: 1, 8, or 13. In some embodiments, the peptide is linked to a polypeptide. In some embodiments, the peptide is linked to the polypeptide through a covalent or non-covalent linkage. In some embodiments, the polypeptide is a thermostable protein. In some embodiments, the thermostable protein is an enzyme. In some embodiments, the enzyme is a polymerase, a revere transcriptase, a nuclease, a protease, a pyrophosphatase, or a deaminase. In some embodiments, the polymerase is DNA polymerase I, *Thermus aquaticus* DNA polymerase I (Taq), or *Thermococcus gorgonarius* DNA polymerase (Tgo). In some embodiments, the polymerase is a Taq polymerase. In some embodiments, the pyrophosphatase is *Thermoplasma acidophilum* pyrophosphatase (TAPP). In some embodiments, the deaminase is *Pyrococcus horikoshii* dCTP deaminase. In some embodiments, the deaminase is a cytidine deaminase or a deoxycytidine deaminase. In some embodiments, the deaminase is a RNA deaminase or a DNA deaminase. In some embodiments, the polypeptide is a non-thermostable protein. In some embodiments, said polypeptide, first polypeptide or second polypeptide is *Thermus thermophilics* (Tth) DNA polymerase or ZO5 polymerase.

In some embodiments, the polypeptide, first polypeptide or second polypeptide is human Leukemia Inhibitor Factor (hLIF) or leptin. In some embodiments, the peptide-linked polypeptide retains an enzymatic activity after exposure to a temperature of about −20° C. to about 35° C. In some embodiments, the polypeptide exhibits an enzymatic activity after exposure to a temperature of about 20° C. to about 30° C. In some embodiments, the exposure to a temperature is for greater than 1 day. In some embodiments, the enzymatic activity is greater than about 50% of the activity of the composition prior to the exposure to a temperature of at least about −20° C. to about 35° C. In some embodiments, the peptide is encoded by a nucleotide sequence that is at least 70% identical to SEQ ID NO: 3 or SEQ ID NO: 7.

In yet a further aspect, this disclosure provides a fusion polypeptide comprising a first peptide that is at least 70% identical to a peptide encoded by SEQ ID NO: 3 and a second peptide that is at least 70% identical to a peptide encoded by SEQ ID NO: 9. In some embodiments, said first and second peptides are linked to a third peptide. In some embodiments, said first and second peptides are linked to each other. In some embodiments, said linkage is covalent. In some embodiments, said first peptide is linked to the N-terminus of a polypeptide and wherein said second peptide is linked to the C-terminus of said polypeptide.

In some embodiments, said second peptide is linked to the C-terminus of said first peptide. In some embodiments, said fusion polypeptide had at least 70% identity to a peptide encoded by SEQ ID NO: 7.

In yet another aspect, this disclosure provides a method of nucleic acid amplification comprising extending a nucleic acid primer with a mixture comprising a polymerase, wherein the polymerase is linked to a peptide that is at least 70% identical to a peptide encoded by SEQ ID NO: 3, SEQ ID NO: 7, to SEQ ID NO: 9, SEQ ID NO: 15, SEQ ID NO: 17 or SEQ ID NO: 19. In some embodiments, the polymerase is linked at its N-terminus to the peptide. In some embodiments, the polymerase is linked at its C-terminus to the peptide. In some embodiments, the polymerase is a Taq polymerase. In some embodiments, the polymerase exhibits an enzymatic activity after exposure to a temperature between −20° C. and 50° C. In some embodiments, the polymerase exhibits an enzymatic activity after exposure to a temperature of about −20° C. to about 35° C. In some embodiments, the mixture further comprises a second polymerase. In some embodiments, said second polymerase is linked to a peptide sequence that is at least 70% homologous to SEQ ID NO: 1, SEQ ID NO: 8, SEQ ID NO: 13, SEQ ID NO: 14, SEQ ID NO: 16, or SEQ ID NO: 18. In some embodiments, the polymerase exhibits an enzymatic activity after exposure to a temperature of about 20° C. to about 30° C. for at least one day. In some embodiments, the enzymatic activity is greater than about 50% of the activity of the composition prior to exposure to the temperature of about 20° C. to about 30° C. for at least one day.

In some embodiments, provided herein are methods of increasing stability of a polypeptide comprising providing a peptide tag that has an amino acid sequence that is at least 70% identical to SEQ ID NO: 1.

In some embodiments, provided herein are use of a peptide tag to increase stability of a polypeptide, wherein the peptide tag has an amino acid sequence that is at least 70% identical to SEQ ID NO: 1.

In some embodiments, the peptide tag has an amino acid sequence as shown in SEQ ID NO: 1, SEQ ID NO: 13, SEQ ID NO: 14, SEQ ID NO: 16, or SEQ ID NO: 18. In some embodiments, the peptide tag is encoded by a nucleic acid sequence as shown in SEQ ID NO: 3, SEQ ID NO: 15, SEQ ID NO: 17, or SEQ ID NO: 19. In some embodiments, the peptide tag comprises at least one to six histidine residues. In some embodiments, the peptide tag comprises a protease cleavage site. In some embodiments, the protease cleavage site comprises the amino acid sequence DDDDK (SEQ ID NO: 24). In some embodiments, the peptide tag inhibits degradation or denaturation of the polypeptide at a temperature between −20° C. and 50° C. In some embodiments, the peptide tag inhibits loss of protein function of the polypeptide at a temperature between −20° C. and 50° C. In some embodiments, the protein function of the polypeptide after exposure to said temperature is at least 50% of the protein function of the polypeptide prior to exposure to said temperature. In some embodiments, the peptide tag maintains stability of the polypeptide for at least one day in a temperature between −20° C. and 50° C. In some embodiments, the peptide tag linked to the polypeptide has an amino acid sequence as shown in SEQ ID NO: 6, SEQ ID NO: 8, SEQ ID NO: 11, SEQ ID NO: 20, or SEQ ID NO: 22.

In some embodiments, the peptide tag is linked to the polypeptide. In some embodiments, the peptide tag is covalently linked to the polypeptide. In some embodiments, the peptide tag is non-covalently linked to the polypeptide. In some embodiments, the peptide tag is linked to the amino-terminus of the polypeptide. In some embodiments, the peptide tag is linked to the carboxy-terminus of the polypeptide. In some embodiments, the polypeptide is erythropoietin, human Leukemia Inhibitor Factor (hLIF), granulocyte macrophage colony-stimulating factor (GM-CSF), insulin, vascular endothelial growth factor (VEGF), leptin, or bevacizumab. In some embodiments, the polypeptide comprises at least one mutation.

In some embodiments, the peptide tag is not linked to the polypeptide.

In some embodiments, the peptide tag linked to the polypeptide is encoded by a nucleic acid sequence as shown in SEQ ID NO: 5, SEQ ID NO: 7, SEQ ID NO: 12, SEQ ID NO: 21, or SEQ ID NO: 23. In some embodiments, the polypeptide is a thermostable protein or enzyme. In some embodiments, the enzyme is a polymerase, reverse transcriptase, nuclease, pyrophosphatase, deaminase, or protease. In some embodiments, the polymerase is a DNA polymerase I, *Thermus aquaticus* DNA polymerase I (Taq), *Thermococcus gorgonarius* DNA polymerase (Tgo), *Thermus thermophilics* (Tth) DNA polymerase, or ZO5 DNA polymerase. In some embodiments, the pyrophosphatase is a *Thermoplasma acidophilum* pyrophosphatase (TAPP). In some embodiments, the deaminase is a *Pyrococcus horikoshii* dCTP deaminase.

In some embodiments, provided herein are methods of increasing stability of a polypeptide, fusion polypeptide, or composition comprising providing a peptide tag that is 50% to 98% identical to SEQ ID NO: 1. In some embodiments, provided herein are methods of increasing stability of a polypeptide, fusion polypeptide, or composition comprising providing a polypeptide that is not SEQ ID NO: 2, SEQ ID NO: 6, or SEQ ID NO: 11. In some embodiments, provided herein are methods of inhibiting loss of enzymatic activity or hormone activity of a polypeptide, fusion polypeptide, or composition comprising providing a peptide tag that is 50% to 98% identical to SEQ ID NO: 1. In some embodiments, provided herein are methods of inhibiting loss of enzymatic activity or hormone activity of a polypeptide, fusion polypeptide, or composition comprising providing a polypeptide that is not SEQ ID NO: 2, SEQ ID NO: 6, or SEQ ID NO: 11. In some embodiments, provided herein are methods of inhibiting degradation of a polypeptide, fusion polypeptide, or composition comprising providing a peptide tag that is 50% to 98% identical to SEQ ID NO: 1. In some embodiments, provided herein are methods of inhibiting degradation of a polypeptide, fusion polypeptide, or composition comprising providing a polypeptide that is not SEQ ID NO: 2, SEQ ID NO: 6, or SEQ ID NO: 11. In some embodiments, the peptide is linked to the polypeptide. In some embodiments, the polypeptide or composition further comprises a second polypeptide, wherein the peptide tag linked to the polypeptide increases stability of the second polypeptide. In some embodiments, the polypeptide or composition further comprises a third polypeptide, wherein the peptide tag linked to the polypeptide increases stability of the second polypeptide or the third polypeptide.

In some embodiments, provided herein are methods of increasing stability of a polypeptide comprising providing a peptide tag that has an amino acid sequence that is at least 70% identical to SEQ ID NO: 1, wherein the peptide tag is not SEQ ID NO: 1. In some embodiments, provided herein are use of a peptide tag to increase stability of a polypeptide, wherein the peptide tag has an amino acid sequence that is at least 70% identical to SEQ ID NO: 1, wherein the peptide tag is not SEQ ID NO: 1. In some embodiments, provided herein are methods of increasing stability of a polypeptide, fusion polypeptide, or composition, wherein the polypeptide, fusion polypeptide, or composition is not SEQ ID NO: 1 linked to a polypeptide. In some embodiments, provided herein are use of a peptide tag to increase stability of a polypeptide, fusion polypeptide, or composition comprising, wherein the polypeptide, fusion polypeptide, or composition is not SEQ ID NO: 1 linked to a polypeptide. In some embodiments, provided herein are methods of increasing stability of a polypeptide, fusion polypeptide, or composition, wherein the polypeptide, fusion polypeptide, or composition is not SEQ ID NO: 1 linked to a Taq polymerase. In some embodiments, provided herein are use of a peptide tag to increase stability of a polypeptide, fusion polypeptide, or composition comprising, wherein the polypeptide, fusion polypeptide, or composition is not SEQ ID NO: 1 linked to a Taq polymerase. In some embodiments, provided herein are methods of increasing stability of a polypeptide, fusion polypeptide, or composition, wherein the polypeptide, fusion polypeptide, or composition is not SEQ ID NO: 1 linked to a Tgo polymerase. In some embodiments, provided herein are use of a peptide tag to increase stability of a polypeptide, fusion polypeptide, or composition comprising, wherein the polypeptide, fusion polypeptide, or composition is not SEQ ID NO: 1 linked to a Tgo polymerase.

In yet another aspect, this disclosure provides a nucleic acid vector for use in a bacterium comprising a eukaryotic translation initiation sequence upstream of a nucleic acid sequence encoding a polypeptide linked to a peptide, wherein said polypeptide retains enzymatic activity at a temperature between about −20° C. to about 35° C., or 20° C. to about 50° C. In some embodiments, said polypeptide is translated as both a short and long form. In some embodiments, the eukaryotic translation initiation sequence at least partially encodes a polypeptide that retains an enzymatic activity at a temperature between about −20° C. to about 35° C. In some embodiments, the eukaryotic translation initiation sequence is a Kozak sequence (GCCGCCACCATGGTC) (SEQ ID NO: 25). In some embodiments, the eukaryotic translation initiation sequence is upstream of a nucleic acid sequence encoding a polypeptide that is SEQ ID NOs: 1, 2, 6, 8, 10, 11 or 13 or variants, fragments, or mutants thereof. In some embodiments, the composition comprises a bacterium comprising a nucleic acid vector described herein.

In yet another aspect, this disclosure provides a composition comprising a polypeptide linked to a peptide, wherein said polypeptide retains an enzymatic activity at a temperature between about −20° C. to about 35° C., wherein said polypeptide is encoded by a nucleic acid sequence having a eukaryotic translation initiation sequence. In some embodiments, the polypeptide is a thermostable protein. In some embodiments, the thermostable protein is an enzyme. In some embodiments, the enzyme is a polymerase, a pyrophosphatase, or a deaminase. In some embodiments, the polymerase is a DNA polymerase I, *Thermus aquaticus* DNA polymerase I (Taq), or *Thermococcus gorgonarius* DNA polymerase (Tgo). In some embodiments, the polymerase is a Taq polymerase. In some embodiments, the polymerase is not Taq polymerase. In some embodiments, the pyrophosphatase is *Thermoplasma acidophilum* pyrophosphatase (TAPP). In some embodiments, the deaminase is *Pyrococcus horikoshii* dCTP deaminase. In some embodiments, the deaminase is a cytidine deaminase or a deoxycytidine deaminase. In some embodiments, the deaminase is a RNA deaminase or a DNA deaminase. In some embodiments, said eukaryotic translation initiation sequence is a Kozak sequence (GCCGCCAC-CATGGTC) (SEQ ID NO: 25). In some embodiments, said composition comprises both a short form and a long form of said polypeptide. In some embodiments, said polypeptide linked to a peptide is at least 70% identical to a polypeptide encoded by the nucleic acid sequence of SEQ ID NO: 4, SEQ ID NO: 5, or SEQ ID NO: 12. In some embodiments, said polypeptide is linked to a peptide at least 70% identical to SEQ ID NO: 1, 3 or 10.

In some cases, when the enzyme (e.g., Taq polymerase, DNA deaminase, RNA deaminase) is linked to the peptide (e.g., a peptide at least 70% identical to SEQ ID NO: 1) it exhibits at least 20%, 50%, 75%, 80%, 85%, 90%, 95%, or 100% of its activity prior to short-term or long-term exposure to temperatures of from about −20° C. to about 35° C. In some cases, the exposure occurs for at least 1, 2, 3, 4, 5, 6, or 10 hours, at least 1, 2, 3, 4, 5, or 6 days, or at least 1, 2, 3, 4, 5, 6, or 10 weeks, or at least 1, 2, 3, 4, 5, 6, or 10 months.

All publications, patents, and patent applications mentioned in this specification are herein incorporated by reference in their entirety to the same extent as if each individual publication, patent, or patent application was specifically and individually indicated to be incorporated by reference.

BRIEF DESCRIPTION OF THE DRAWINGS

The novel features of the embodiments provided herein are set forth with particularity in the appended claims. A better understanding of the features and advantages of the embodiments provided herein will be obtained by reference to the following detailed description and drawings that set forth illustrative embodiments, in which the principles of the embodiments are utilized.

FIG. 2 depicts the amino acid sequence (SEQ ID NO: 1) of a 42 amino acid peptide tag.

FIG. 3 depicts the amino acid sequence of a fusion polypeptide (SEQ ID NO: 2) consisting of the peptide tag of FIG. 2 (SEQ ID NO: 1) linked to the N-terminus of wild-type Taq polymerase. The sequence of the 42 amino acid peptide tag is underlined.

FIG. 4 depicts a nucleotide sequence (SEQ ID NO: 3) encoding the 42 amino acid peptide tag (SEQ ID NO: 1).

FIG. 5 depicts the nucleotide sequence of a fusion polypeptide (SEQ ID NO: 2) consisting of the 42 amino acid (a.a.) peptide tag of FIG. 2 (SEQ ID NO: 1) linked to the N-terminus of wild-type Taq polymerase. The entire nucleotide sequence is designated SEQ ID NO: 4. The nucleotide sequence that encodes the 42 amino acid peptide tag is underlined.

FIG. 6 depicts the nucleotide sequence of a fusion polypeptide (SEQ ID NO: 6) consisting of the modified peptide tag fragment of FIG. 2 (SEQ ID NO: 1) (bold and underlined) linked to a peptide corresponding to a fragment of Double-Stranded Binding protein (DSP) (underlined portion, not bolded), linked to the N-terminus of wild-type Taq polymerase. The entire nucleotide sequence is designated SEQ ID NO: 5.

FIG. 7 depicts the amino acid sequence of a fusion polypeptide (SEQ ID NO: 6) consisting of the modified peptide tag fragment of FIG. 2 (SEQ ID NO: 1) (bold and underlined) linked to a peptide corresponding to a fragment of Double-Stranded Binding protein (DSP) (underlined portion, not bolded), linked to the N-terminus of wild-type Taq polymerase.

FIG. 8 depicts the nucleotide sequence (SEQ ID NO: 7) encoding a peptide tag consisting of the modified peptide tag fragment of FIG. 2 (SEQ ID NO: 1) (bold and underlined) linked to a peptide corresponding to a fragment of Double-Stranded Binding protein (DSP) (underlined portion, not bolded).

FIG. 9 depicts the amino acid sequence (SEQ ID NO: 8) of a tag peptide consisting of the modified peptide tag fragment of FIG. 2 (SEQ ID NO: 1) (bold and underlined) linked to a peptide corresponding to a fragment of Double-Stranded Binding protein (DSP) (underlined portion, not bolded).

FIG. 10 depicts the nucleotide sequence (SEQ ID NO: 9) encoding a DSP tag peptide.

FIG. 11 depicts the amino acid sequence (SEQ ID NO: 10) of the DSP tag.

FIG. 12 depicts the amino acid sequence (SEQ ID NO: 11) of a fusion polypeptide of the modified peptide tag fragment of FIG. 2 (SEQ ID NO: 1) (bold and underlined) linked to a Tgo polymerase polypeptide linked to a DSP peptide (underlined portion, not bolded).

FIG. 13 depicts the nucleotide sequence (SEQ ID NO: 12) encoding a a fusion polypeptide of the modified peptide tag fragment of FIG. 2 (SEQ ID NO: 1) (bold and underlined) linked to a Tgo polymerase polypeptide, which is linked to a DSP peptide (underlined portion, not bolded).

FIG. 14 depicts the amino acid sequence (SEQ ID NO: 13) of a fragment of the peptide of SEQ ID NO: 1.

FIG. 16 depicts an amino acid sequence (SEQ ID NO: 14) of a modified fragment of the peptide of SEQ ID NO: 1.

FIG. 17 depicts a nucleotide sequence (SEQ ID NO: 15) encoding the 36 amino acid peptide (SEQ ID NO: 14).

FIG. 18 depicts an amino acid sequence (SEQ ID NO: 16) of a modified fragment of the peptide of SEQ ID NO: 1.

FIG. 19 depicts a nucleotide sequence (SEQ ID NO: 17) encoding the 40 amino acid peptide (SEQ ID NO: 16).

FIG. 20 depicts an amino acid sequence (SEQ ID NO: 18) of a modified fragment of the peptide of SEQ ID NO: 1.

FIG. 21 depicts a nucleotide sequence (SEQ ID NO: 19) encoding the 29 amino acid peptide (SEQ ID NO: 18).

FIG. 22 depicts an amino acid sequence (SEQ ID NO: 20) of a modified fragment of the peptide of SEQ ID NO: 1 linked to a human erythropoietin polypeptide.

FIG. 23 depicts a nucleotide sequence (SEQ ID NO: 21) encoding the polypeptide of SEQ ID NO: 20.

FIG. 24 depicts an amino acid sequence (SEQ ID NO: 22) of a modified fragment of the peptide of SEQ ID NO: 1 linked to a human leukemia inhibitory factor.

FIG. 25 depicts a nucleotide sequence (SEQ ID NO: 23) encoding the polypeptide of SEQ ID NO: 22.

DETAILED DESCRIPTION OF THE INVENTION

Overview

Figure 1:
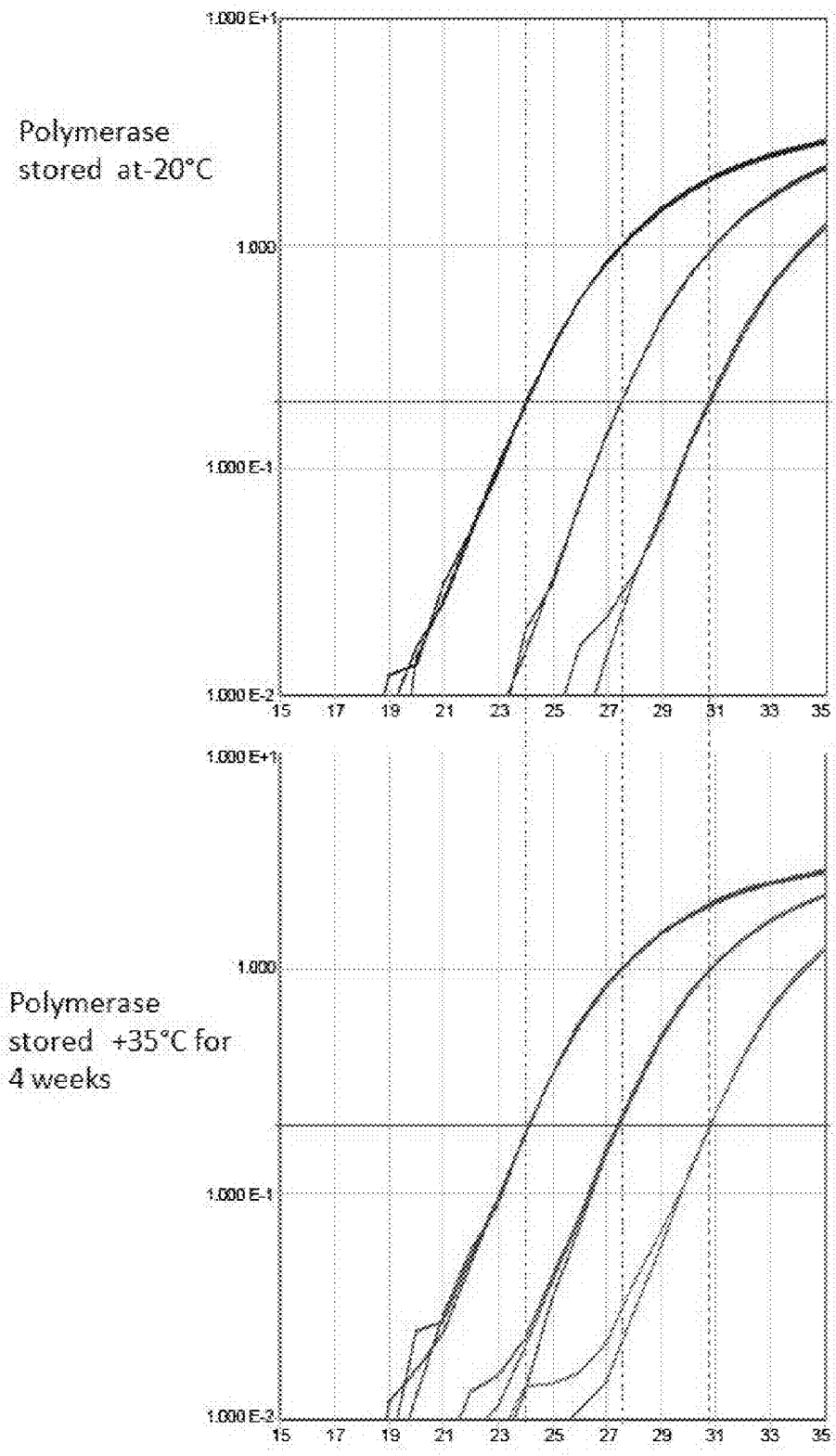
FIG. 1 depicts a qPCR amplification that is performed in order to test the stability of a peptide-polypeptide fusion protein (SEQ ID NO: 2) after exposure to 35° C. The first sample of fresh qPCR mix is stored at −20° C. (top panel) and the second sample is stored at 35° C. for 4 weeks (lower panel).

The present disclosure provides compositions and methods that enhance the stability of proteins (e.g., thermostable enzymes, non-thermostable enzymes) following short-term or long-term exposure to a temperature between −20° C. and +50° C. or from about −20° C. to +35° C. In some embodiments, the compositions are peptide tags or fusion proteins comprising peptide tags. The proteins can be any type of protein. The peptide tags may aid the retention of protein structure, stability, enzymatic activity, binding activity, and any other property. In some embodiments, the proteins are nucleic acid binding proteins. In some embodiments, the fusion proteins demonstrate enhanced stability or enzymatic activity when compared to a similar protein that does not have the tag, especially after short-term or long-term exposure to a certain temperature (e.g., room temperature). Also disclosed herein are fusion polypeptides that enhance the activity (e.g., sensitivity, yield, specificity) of other proteins, when the fusion polypeptides are mixed together with such proteins in a reaction sample. Also provided are vectors for the compositions described herein, kits, as well as methods of using the compositions.

Peptide Tags

The compositions disclosed herein include peptides (e.g., a peptide with the amino acid sequence of SEQ ID NO: 1 (FIG. 2), SEQ ID NO: 8 (FIG. 9), SEQ ID NO: 10 (FIG. 11), SEQ ID NO: 13 (FIG. 14), SEQ ID NO: 14 (FIG. 16)) that enhance the stability of a polypeptide (e.g., enzyme, Taq polymerase), and variants, mutants, and fragments thereof.

As used herein, enhancing or increasing stability of a polypeptide refers to, for example, maintaining stability of the polypeptide, inhibiting degradation of the polypeptide, inhibiting denaturation of the polypeptide, inhibiting loss of protein activity (e.g., enzymatic or hormone activity) of the polypeptide, inhibiting aggregation of the polypeptide, inhibiting crystallization of the polypeptide, inhibiting absorption of the polypeptide, preserving the function of the polypeptide, or preserving the primary, secondary, or tertiary structure of the polypeptide.

SEQ ID NO: 1 (FIG. 2) shows the amino acid sequence of a long form (42 amino acids) of peptide tag described herein. SEQ ID NO: 13 (FIG. 14) discloses a 31 amino acid fragment of SEQ ID NO: 1, that can also be used as a peptide tag for the polypeptides, fusion polypeptides, compositions, and methods disclosed herein. SEQ ID NO: 14 (FIG. 16) discloses a 36 amino acid fragment of SEQ ID NO: 1, which can also be used as a peptide tag for the polypeptides, fusion polypeptides, compositions, and methods disclosed herein. SEQ ID NO: 1, SEQ ID NO: 13, and SEQ ID NO: 14 can be used singly, together, or in combination with other tags, in order to enhance the stability, binding affinity, enzymatic activity, yield, or other property of a polypeptide.

SEQ ID NO: 10 discloses the sequence of a fragment of a double-stranded DNA binding protein (DSP). The peptide of SEQ ID NO: 10 can also be used in the compositions and methods described herein, either on its own, or with the peptide tag of SEQ ID NO: 1, or other peptide tag described herein. For example, FIG. 7 (SEQ ID NO: 6) provides an example of a polymerase linked to a fragment of SEQ ID NO; 1 and to a fragment of SEQ ID NO: 10. FIG. 12 (SEQ ID NO: 11) provides an example of a polymerase (here, tgo polymerase) that is linked both to a fragment of SEQ ID NO: 1 and to a fragment of DSP, SEQ ID NO: 10, which is disclosed as the unbolded, underlined sequence in SEQ ID NO: 11 (FIG. 12).

The compositions also include peptides that are at least 50%, 60%, 65%, 70%, 75%, 80%, 85%, 90%, or 95% identical (or homologous) to SEQ ID NO: 1 (FIG. 2) SEQ ID NO: 8 (FIG. 9), SEQ ID NO: (FIG. 11), SEQ ID NO: 13 (FIG. 14), or SEQ ID NO: 14 (FIG. 16). Similarly, the compositions further include peptides that are at least 50%, 60%, 65%, 70%, 75%, 80%, 85%, 90%, or 95% identical to peptides encoded by SEQ ID NO: 3, SEQ ID NO: 7, SEQ ID NO: 9, or SEQ ID NO: 15.

In some embodiments, the peptide tag is limited to 50 amino acids. In some embodiments, the peptide tag is limited to 55, 60, 65, 70, 75, 80, 85, 90, 95, or 100 amino acids.

The percent sequence identity of two amino acid sequences are aligned using a global alignment that takes account the entire length of the peptide or polypeptide, as described by the Needleman-Wunsch-Sellers algorithm (Needleman et al., (1970), J. Mol. Biol. 48:444; Sellers (1974), SIAM J. Appl. Math., 26:787. Illustrative parameters for FASTA analysis are: ktup=1, gap opening penalty=10, gap extension penalty=1, and substitution matrix=BLOSUM62.

In some embodiments, peptide tags provided herein comprise a His peptide tag, wherein the His peptide tag comprises at least 1, 2, 3, 4, 5, 6, 7, 8, 9, 10, 11, 12, 13, 14, 15, or 20 His residues (SEQ ID NO: 26). In some embodiments, peptide tags provided herein comprise a His peptide tag, wherein the His peptide tag comprises no more than 1, 2, 3, 4, 5, 6, 7, 8, 9, 10, 11, 12, 13, 14, 15, or 20 His residues (SEQ ID NO: 27). In some embodiments, the His peptide tag comprises from 1 to 5 (SEQ ID NO: 28), 2 to 6 (SEQ ID NO: 29), 3 to 7 SEQ ID NO: 30), 4 to 8 (SEQ ID NO: 31), 5 to 9 (SEQ ID NO: 32), 6 to 10 (SEQ ID NO: 33), 7 to 11 (SEQ ID NO: 34), 8 to 12 (SEQ ID NO: 35), 9 to 13 (SEQ ID NO: 36), 10 to 14 (SEQ ID NO: 37), 1 to 10 (SEQ ID NO: 38), 2 to 11 (SEQ ID NO: 39), 3 to 12 (SEQ ID NO: 40), 4 to 13 (SEQ ID NO: 41), 5 to 14 (SEQ ID NO: 42), 6 to 15 (SEQ ID NO: 43), 7 to 16 (SEQ ID NO: 44), 8 to 17 (SEQ ID NO: 45), 9 to 19 (SEQ ID NO: 46), 10 to 20 (SEQ ID NO: 47), 1 to 20 (SEQ ID NO: 48), 2 to 19 (SEQ ID NO: 49), 3 to 18 (SEQ ID NO: 50), 4 to 17 (SEQ ID NO: 51), 5 to 16 (SEQ ID NO: 52), 6 to 15 (SEQ ID NO: 53), 7 to 14 (SEQ ID NO: 54), 8 to 13 (SEQ ID NO: 55), 9 to 12 (SEQ ID NO: 56), 10 to 11 (SEQ ID NO: 57), 1 to 6 (SEQ ID NO: 58), 1 to 7 (SEQ ID NO: 59), 1 to 8 (SEQ ID NO: 60), 1 to 9 (SEQ ID NO: 61), or 1 to 10 (SEQ ID NO: 38) His residues.

In some embodiments, peptide tags provided herein comprise a sequence that can be cleaved by a protease. In some embodiments, the peptide tag comprises a protease cleavage site. Non-limiting examples of proteases and associated cleavage residues (in parenthesis) include trypsin (Arg or Lys), chymotrypsin (Trp, Tyr, Phe, Leu, Met, or His), endoproteinase Asp-N(Asp), endoproteinase Arg-C(Arg), endoproteinase Glu-C(Glu), endoproteinase Lys-C(Lys), prolin-endopeptidase (Pro), pepsin (Phe, Tyr, Trp, or Leu), thermolysin (Ile, Leu, Val, Ala, Met, or Phe), thrombin (Arg) elastase (Ala or Val), papain (Leu or Gly), proteinase K (aromatic amino acids), subtilisin (His, Ser, Asp), and clostripain (Arg). In some embodiments, the peptide tags comprise a sequence that can be cleaved by a carboxypeptidase, carboxypeptidase A, carboxypeptidase B, carboxypeptidase P, carboxypeptidase Y, cathepsin C, acycloamino-acid-releasing enzyme, and pyroglutamate aminopeptidase. In some embodiments, the peptide tags provided herein comprise a protease cleavage site, wherein the peptide tag comprises at least 1, 2, 3, 4, 5, 6, 7, 8, 9, 10, 11, 12, 13, 14, 15, or 20 protease cleavage sites. In some embodiments, peptide tags provided herein comprise a protease cleavage site, wherein the protease cleavage site comprises no more than 1, 2, 3, 4, 5, 6, 7, 8, 9, 10, 11, 12, 13, 14, 15, or 20 protease cleavage sites. In some embodiments, the peptide tag comprises from 1 to 5, 2 to 6, 3 to 7, 4 to 8, 5 to 9, 6 to 10, 7 to 11, 8 to 12, 9 to 13, 10 to 14, 1 to 10, 2 to 11, 3 to 12, 4 to 13, 5 to 14, 6 to 15, 7 to 16, 8 to 17, 9 to 19, 10 to 20, 1 to 20, 2 to 19, 3 to 18, 4 to 17, 5 to 16, 6 to 15, 7 to 14, 8 to 13, 9 to 12, 10 to 11, 1 to 6, 1 to 7, 1 to 8, 1 to 9, or 1 to 10 protease cleavage sites. In some cases the protease cleavage site has the sequence: DDDDK (SEQ ID NO: 24). In some cases, the protease cleavage site has at least four "D" residues. The protease cleavage site may be at least 50%, 60%, 65%, 70%, 75%, 80%, 85%, 90%, or 95% identical to the sequence DDDDK (SEQ ID NO: 24). In some cases, the peptide tag may comprise a sequence that resembles a protease cleavage site, but that actually does not serve as a site of proteolytic cleavage. In some embodiments, peptide tags provided herein comprise a (Asp) D tag, wherein the peptide tag comprises at least 1, 2, 3, 4, 5, 6, 7, 8, 9, 10, 11, 12, 13, 14, 15, or 20 Asp residues, e.g., DD, DDD, DDDD (SEQ ID NO: 25), etc. In some embodiments, the Asp tag comprises at least 4 Asp residues. In some embodiments, peptide tags provided herein comprise an Asp tag with no more than 1, 2, 3, 4, 5, 6, 7, 8, 9, 10, 11, 12, 13, 14, 15, or 20 Asp residues. In some embodiments, the Asp tag comprises from 1 to 5, 2 to 6, 3 to 7, 4 to 8, 5 to 9, 6 to 10, 7 to 11, 8 to 12, 9 to 13, 10 to 14, 1 to 10, 2 to 11, 3 to 12, 4 to 13, 5 to 14, 6 to 15, 7 to 16, 8 to 17, 9 to 19, 10 to 20, 1 to 20, 2 to 19, 3 to 18, 4 to 17, 5 to 16, 6 to 15, 7 to 14, 8 to 13, 9 to 12, 10 to 11, 1 to 6, 1 to 7, 1 to 8, 1 to 9, or 1 to 10 Asp residues. In some embodiments, the peptide tag comprises a His tag (as described herein) and an Asp tag. In some embodiments, one or more Asp residues is substituted with another amino acid (e.g., one or more Glu residues). In some embodiments, the His tag is substituted with one or more amino acids (e.g., Lys or Arg).

All references to polypeptides, proteins and peptides, as used herein, refer to a polymer of amino acid residues. That is, a description directed to a polypeptide applies equally to a description of a peptide and a description of a protein, and vice versa. The terms apply to naturally occurring amino acid polymers as well as amino acid polymers in which one or more amino acid residues is a non-naturally occurring amino acid, e.g., an amino acid analog. As used herein, the terms encompass amino acid chains of any length, including full length proteins (i.e., antigens), wherein the amino acid residues are linked by covalent peptide bonds.

The term "amino acid" refers to naturally occurring and non-naturally occurring amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrolysine and selenocysteine. Amino acid analogs refers to compounds that have the same basic chemical structure as a naturally occurring amino acid, i.e., an a carbon that is bound to a hydrogen, a carboxyl group, an amino group, and an R group, such as, homoserine, norleucine, methionine sulfoxide, methionine methyl sulfonium. Such analogs have modified R groups (such as, norleucine) or modified peptide backbones, but retain the same basic chemical structure as a naturally occurring amino acid.

As used herein, the term "unnatural amino acid" or "non-naturally encoded amino acid" refers to any amino acid, modified amino acid, and/or amino acid analogue that is not one of the 20 common naturally occurring amino acids or selenocysteine or pyrrolysine. Other terms that may be used synonymously with the term "non-naturally encoded amino acid" and "unnatural amino acid" are "non-natural amino acid," "non-naturally-occurring amino acid," and variously hyphenated and non-hyphenated versions thereof. The term "non-naturally encoded amino acid" also includes, but is not limited to, amino acids that occur by modification (e.g. post-translational modifications) of a naturally encoded amino acid (including but not limited to, the 20 common amino acids or pyrrolysine and selenocysteine) but are not themselves naturally incorporated into a growing polypeptide chain by the translation complex. Examples of such non-naturally-occurring amino acids include, but are not limited to, N-acetylglucosaminyl-L-serine, N-acetylglucosaminyl-L-threonine, O-phosphotyrosine, aminoadipic acid, beta-alanine, beta-aminopropionic acid, aminobutyric acid, piperidinic acid, aminocaprioic acid, aminoheptanoic acid, aminoisobutyric acid, aminopimelic acid, diaminobutyric acid, desmosine, diaminopimelic acid, diaminopropionic acid, N-ethylglycine, N-ethylasparagine, hyroxylysine, allo-hydroxylysine, hydroxyproline, isodesmosine, allo-isoleucine, N-methylglycine, sarcosine, N-methylisoleucine, N-methylvaline, norvaline, norleucine, orithine, 4-hydroxyproline, gamma-carboxyglutamate, epsilon-N,N,N-trimethyllysine, epsilon-N-acetyllysine, O-phosphoserine, N-acetylserine, N-formylmethionine, 3-methylhistidine, 5-hydroxylysine, sigma-N-methylarginine, and other similar amino acids and amino acids (e.g., 4-hydroxyproline).

The term "peptide" refers to a polymer composed of one to about 50 amino acid residues related naturally occurring structural variants, and synthetic non-naturally occurring analogs thereof linked via peptide bonds.

The term "polypeptide" refers to a polymer composed of at least about 50 amino acid residues, related naturally occurring structural variants, and synthetic non-naturally occurring analogs thereof linked via peptide bonds. As used herein, polypeptides provided herein may be fusion polypeptides or proteins.

The term "nucleic acid" refers to naturally occurring and non-naturally occurring nucleic acids, as well as nucleic acid analogs that function in a manner similar to the naturally occurring nucleic acids. The nucleic acids may be selected from RNA, DNA or nucleic acid analog molecules, such as sugar- or backbone-modified ribonucleotides or deoxyribonucleotides. It should be noted, however, that other nucleic analogs, such as peptide nucleic acids (PNA) or locked nucleic acids (LNA), are also suitable. Examples of non-naturally occurring nucleic acids include: halogen-substituted bases, alkyl-substituted bases, hydroxy-substituted bases, and thiol-substituted bases, as well as 5-propynyl-uracil, 2-thio-5-propynyl-uracil, 5-methylcytosine, isoguanine, isocytosine, pseudoisocytosine, 4-thiouracil, 2-thiouracil and 2-thiothymine, inosine, 2-aminopurine, N9-(2-amino-6-chloropurine), N9-(2,6-diaminopurine), hypoxanthine, N9-(7-deaza-guanine), N9-(7-deaza-8-aza-guanine) and N8-(7-deaza-8-aza-adenine), 2-amino-6-"h"-purines, 6-amino-2-"h"-purines, 6-oxo-2-"h"-purines, 2-oxo-4-"h"-pyrimidines, 2-oxo 6-"h"-purines, 4-oxo-2-"h"-pyrimidines. Those will form two hydrogen bond base pairs with non-thiolated and thiolated bases; respectively, 2,4 dioxo and 4-oxo-2-thioxo pyrimidines, 2,4 dioxo and 2-oxo-4-thioxo pyrimidines, 4-amino-2-oxo and 4-amino-2-thioxo pyrimidines, 6-oxo-2-amino and 6-thioxo-2-amino purines, 2-amino-4-oxo and 2-amino-4-thioxo pyrimidines, and 6-oxo-2-amino and 6-thioxo-2-amino purines.

The term "about," as used herein, unless otherwise indicated, refers to a value that is no more than 10% above or below the value being modified by the term. For example, the term "about −20° C." means a range of from −22° C. to −18° C. As another example, "about 1 hour" means a range of from 54 minutes to 66 minutes.

Linkages

In some embodiments, peptide tags provided herein enhance the stability of a protein (or polypeptide) after being linked to the protein in some manner (e.g., covalent or non-covalent linkage). In some cases, a peptide (e.g., the peptide of SEQ ID NO: 1, 8, 10, 13, or 14) is covalently linked to a polypeptide or enzyme (e.g., Taq, Tgo, TAPP, CDA, *Pyrococcus horikoshii* deaminase). The peptide may be linked to the N-terminus of the polypeptide or enzyme (e.g., Taq, Tgo, TAPP, CDA, *Pyrococcus horikoshii* deaminase). For example, a peptide that is at least 70% identical to a peptide encoded by SEQ ID NO: 3 may be linked to the N-terminus of Taq polymerase as depicted in FIG. 3. Similarly, a peptide that is at least 70% identical to a peptide encoded by SEQ ID NO: 7 may be linked to the N-terminus of Taq polymerase as depicted in FIG. 7. In other cases, the peptide is linked to the C-terminus of a polypeptide or enzyme. For example, FIG. 13 depicts the nucleic acid sequence of Tgo polymerase that is linked at its C-terminus to a fragment of DSP peptide.

In some cases, multiple peptide tags are linked to a polypeptide described herein. A polypeptide can be linked to multiple copies of the same peptide tag or to two or more different peptide tags. In some examples, one peptide tag is linked to the N-terminus of the polypeptide, while a second peptide tag is linked to the C-terminus of the polypeptide. For example, the polypeptide shown in FIG. 12 (SEQ ID NO: 11) includes a peptide tag (SEQ ID NO: 1) linked to the N-terminus of tgo polymerase and also a different peptide tag (DSP fragment) (underlined portion of SEQ ID NO: 11) fused to the C-terminus of the tgo polymerase. In still other examples, two or more (same or different) tags are linked in tandem to a polypeptide. For example, FIG. 7 (SEQ ID NO: 6) depicts a fragment of SEQ ID NO: 1 linked to the DSP peptide of SEQ ID NO: 10 (FIG. 11), which is then linked to another fragment of SEQ ID NO: 1, which is linked to the N-terminus of Taq polymerase.

In some cases, peptide tags provided herein are directly linked to each other and/or to the polypeptide. FIG. 7 shows an example of tags directly linked to each other, and then directly linked to a polypeptide. In other cases, the tags are separated from each other by a linker, (e.g., peptide linker or other linker described herein). The tags may also be linked to the polypeptide by a linker.

In some embodiments, a peptide is linked to the polypeptide or enzyme (e.g., polymerase) via genetic engineering. For example, a DNA construct is created that is capable of expressing a polypeptide comprising the peptide (e.g., the peptide of SEQ ID NO: 1) fused to an enzyme (e.g., Taq polymerase). One example of a portion of the nucleic acid sequence of such construct is depicted in FIG. 5 (SEQ ID NO: 4). Another example is depicted in FIG. 6, SEQ ID NO: 5, and still another is depicted in FIG. 13 (SEQ ID NO: 12).

In some cases a polypeptide (e.g., polymerase, Taq polymerase, etc.) is linked to a peptide comprising a fragment (also referred to herein as a "portion") of double stranded binding protein (DSP) (SEQ ID NO:6, underlined but not bolded portion), or variants, fragments, or mutants thereof. In some cases the DSP fragment is linked to a peptide tag (e.g., to a peptide that is SEQ ID NO:1 or 13, or mutants or variants thereof. In still other cases, the peptide (e.g., the peptide of SEQ ID NO: 1 or 13) is linked to a fragment of a polymerase, which is linked to a second polymerase.

In some embodiments, a peptide may also be linked to the enzyme through a linker, such as a peptide linker. The peptide sequence linker may be 1, 2, 3, 4, 5, 6, 7, 8, 9, 10, or more than 10 amino acids in length. Examples are polypeptides that contain multiple aspartate or glutamate residues. The sequence and length of an appropriate peptide can be determined by methods known in the art, for example by employing a peptide linker prediction software program to identify potential linkers. One example of such linker program is disclosed in George and Heringa, (2003), *Protein Engineering*, 15(11):871-879.

In still other cases, a peptide (e.g., the peptide of SEQ ID NO: 1) is linked to an enzyme via a non-covalent linkage. Examples of linkers that may be useful include: acid labile linkers, ester linkers, hydrazone linkers, sulfonamide-containing linkers, enzymatically cleavable linkers, or polymer based linkers. Polymer-based linkers, such as polyethyleneglycol (PEG, Formula VI), are widely used to conjugate both small molecule and large molecule drugs. When used to link a peptide to a therapeutic, the PEG conjugated polypeptides may offer a number of desirable advantages including higher solubility, less immunogenicity, improved half-life, targeted delivery and enhanced activity of the drugs.

Many molecules with multiple reactive groups can serve as useful cross-linking components and are commercially available from companies like Sigma-Aldrich, or Pierce. Of particular utility are cross-linking components that are available in activated form and can be directly used for conjugation. Cross-linking components can comprise multiple reactive groups with similar or identical chemical structure. Such reactive groups can be simultaneously activated and coupled to multiple identical non-cross-linking components resulting in the direct formation of homomultimeric products. Examples for cross-linking components with multiple similar reactive groups are citric acid, EDTA, TSAT. Branched PEG molecules containing multiple identical reactive groups may also be useful.

There are a large number of specific chemical products that work based on the following small number of basic reaction schemes, all of which are described in detail at www.piercenet.com. Examples of useful crosslinking agents are imidoesters, active halogens, maleimide, pyridyl disulfide, and NHS-esters. Homobifunctional crosslinking agents have two identical reactive groups and are often used in a one-step chemical crosslinking procedure. Examples are BS3 (a non-cleavable water-soluble DSS analog), BSOCOES (base-reversible), DMA (Dimethyl adipimidate-2HCl), DMP (Dimethyl pimelimidate-2HCl), DMS (Dimethyl suberimidate-2HCl), DSG (5-carbon analog of DSS), DSP (Lomant's reagent), DSS (non-cleavable), DST (cleavable by oxidizing agents), DTBP (Dimethyl 3,3'-dithiobispropionimidate-2HCl), DTSSP, EGS, Sulfo-EGS, THPP, TSAT, DFDNB (1,5-Difluoro-2,4-dinitrobenzene) is especially useful for crosslinking between small spacial distances (Kornblatt, J. A. and Lake, D. F. (1980). Cross-linking of cytochrome oxidase subunits with difluorodinitrobenzene. Can J. Biochem. 58, 219-224).

Sulfhydryl-reactive homobifunctional crosslinking agents are homobifunctional protein crosslinkers that react with sulfhydryls and are often based on maleimides, which react with —SH groups at pH 6.5-7.5, forming stable thioether linkages. BM[PEO]3 is an 8-atom polyether spacer that reduces potential for conjugate precipitation in sulfhydryl-to-sulfhydryl cross-linking applications. BM[PEO]4 is similar but with an 11-atom spacer. BMB is a non-cleavable crosslinker with a four-carbon spacer. BMDB makes a linkage that can be cleaved with periodate. BMH is a widely used homobifunctional sulfhydryl-reactive crosslinker. BMOE has an especially short linker. DPDPB and DTME are cleavable crosslinkers. HVBS does not have the hydrolysis potential of maleimides. TMEA is another option. Hetero-bifunctional crosslinking agents have two different reactive groups. Examples are NHS-esters and amines/hydrazines via EDC activation, AEDP, ASBA (photoreactive, iodinatable), EDC (water-soluble carbodiimide) Amine-Sulfhydryl reactive bifunctional crosslinkers are AMAS, APDP, BMPS, EMCA, EMCS, GMBS, KMUA, LC-SMCC, LC-SPDP, MBS, SBAP, SIA (extra short), SIAB, SMCC, SMPB, SMPH, SMPT, SPDP, Sulfo-EMCS, Sulfo-GMBS, Sulfo-KMUS, Sulfo-LC-SMPT, Sulfo-LC-SPDP, Sulfo-MBS, Sulfo-SIAB, Sulfo-SMCC, Sulfo-SMPB. Amino-group reactive heterobifunctional crosslinking agents are ANB-NOS, MSA, NHS-ASA, SADP, SAED, SAND, SANPAH, SASD, SFAD, Sulfo-HSAB, Sulfo-NHS-LC-ASA, Sulfo-SADP, Sulfo-SANPAH, TFCS. Arginine-reactive crosslinking agents are, for example APG, which reacts specifically with arginines at pH 7-8.

Some Properties of the Peptide Tags

In some cases, the peptide enables an enzyme to exhibit at least 10%, 15%, 20%, 25%, 30%, 35%, 40%, 45%, 50%, 55%, 60%, 65%, 70%, 75%, 80%, 85%, 90%, 95%, 96%, 97%, 98%, 99%, or 100% of the activity of the same or similar enzyme that is not linked to the peptide. In some cases, the peptide enables an enzyme to exhibit at least 10%, 20%, 30%, 40%, 50%, 60%, 70%, 75%, 80%, 85%, 90%, 95%, 96%, 97%, 98%, 99%, or 100% of its enzymatic activity prior to long-term or short-term exposure to a temperature (e.g, room temperature, any temperature above −20° C.). In some cases, the peptide enables a polypeptide to exhibit at least 10%, 20%, 30%, 40%, 50%, 60%, 70%, 75%, 80%, 85%, 90%, 95%, 96%, 97%, 98%, 99%, or 100% of its binding affinity compared to its binding affinity prior to long-term or short-term exposure to a temperature (e.g., room temperature, any temperature above −20° C.).

In some cases, a polypeptide fusion protein described herein can enhance the activity of other polypeptides in a reaction mixture. For example, in some cases, a fusion polypeptide (e.g., a fusion polypeptide encoded by SEQ ID NO: 4, SEQ ID NO: 5, or SEQ ID NO: 12), enhances the sensitivity, specificity, fidelity, or yield of a reaction. For example, a fusion polypeptide with DNA polymerase activity (e.g., SEQ ID NO: 2, SEQ ID NO: 6, or SEQ ID NO: 11) can be added to a sample containing a second (different) DNA polymerase (e.g., Taq polymerase, the Taq fusion of SEQ ID NO: 2, SEQ ID NO: 6, or SEQ ID NO: 11), and thereby enhance the specificity, fidelity, sensitivity or yield of the second DNA polymerase. In some cases, the enhancement is more than 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, 100%, 125%, 150%, 175%, 200%, 250%, 300%, 350%, 400%, 450%, 500%, 600%, 700%, 800%, 900%, 1000%, 2000%, 2500%, 3000%, 4000%, or 5000%. In some cases, the fusion polypeptide also enhances the specificity, fidelity or yield of a third polymerase, or of a reaction mix containing three or more polymerases.

In some embodiments, peptide tags described herein will enhance the stability, enzymatic activity, or other property of a fusion polypeptide after short- or long-term exposure to a certain temperature (e.g., room temperature). For example, a polymerase (e.g., Taq polymerase) may lose a substantial portion of its activity after exposure to room temperature for a period of a week or more, or even a day or more or three hours or more.

In some embodiments, a composition disclosed herein (e.g., a peptide with the amino acid sequence of SEQ ID NO: 1 (FIG. 2), of SEQ ID NO: 8 (FIG. 9), or of SEQ ID NO: 10 or 13) may be linked to the enzyme or polymerase (e.g., Taq polymerase, TGO polymerase) and thereby enable the enzyme or polymerase to retain activity after exposure to a temperature (e.g., room temperature) over time. In some cases, a peptide is linked to a polymerase (e.g., Taq polymerase) and thereby enables the polymerase to retain at least 10%, 15%, 20%, 25%, 30%, 35%, 40%, 45%, 50%, 55%, 60%, 65%, 70%, 75%, 80%, 85%, 90%, 95%, 96%, 97%, 98%, 99%, or 100% of its activity, even after long-term or short-term exposure to a certain temperature (e.g., room temperature of about 20° C. to 22° C.). In some cases, the peptide is linked to a polymerase or enzyme that is not Taq polymerase.

In some embodiments, peptide tags described herein may also enhance the ability of a polypeptide (e.g., polymerase) to bind to single-stranded DNA and/or double-stranded DNA. Often, such DNA-binding is nonspecific. In some cases, the enhancement is more than 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, 100%, 125%, 150%, 175%, 200%, 250%, 300%, 350%, 400%, 450%, 500%, 600%, 700%, 800%, 900%, 1000%, 2000% 2500%, 3000%, 4000%, or 5000%. The DSP peptide tag depicted in SEQ ID NO: 10 and fragments, variants, and mutants thereof, may be especially suited for enhancing the non-specific double- or single-stranded DNA-binding ability of a polypeptide.

In some embodiments, polypeptides, fusion polypeptides, or compositions retain activity thereof at a temperature between −20° C. and 50° C. In some embodiments, polypeptides, fusion polypeptides, or compositions retain activity thereof at a temperature between −15° C. and 50° C.; between −10° C. and 50° C.; between −5° C. and 50° C.; between 0° C. and 50° C.; between 5° C. and 50° C.; between 10° C. and 50° C.; between 15° C. and 50° C.; between 20° C. and 50° C.; between 20° C. and 45° C.; between 20° C. and 40° C.; between 20° C. and 35° C.; between 20° C. and 30° C.; between 20° C. and 25° C.; between 20° C. and 22° C.; between 15° C. and 25° C.; between 10° C. and 25° C.; between 5° C. and 25° C.; between 0° C. and 25° C.; between 0° C. and 30° C.; between 0° C. and 35° C.; between 0° C. and 40° C.; between 0° C. and 45° C.; between 5° C. and 10° C.; between 5° C. and 15° C.; between 5° C. and 20° C.; between 5° C. and 25° C.; between 5° C. and 30° C.; between 5° C. and 35° C.; between 5° C. and 40° C.; between 5° C. and 45° C.; between 10° C. and 15° C.; between 10° C. and 20° C.; between 10° C. and 25° C.; between 10° C. and 30° C.; between 10° C. and 35° C.; between 10° C. and 40° C.; between 10° C. and 45° C.; between 15° C. and 20° C.; between 15° C. and 30° C.; between 15° C. and 35° C.; between 15° C. and 40° C.; between 15° C. and 45° C.

In some cases, the fusion polypeptide (e.g., fusion protein of SEQ ID NO: 2, 6, or 11) is exposed to a temperature that is at least about −20° C., −19° C., −18° C., −17° C., −16° C., −15° C., −14° C., −13° C., −12° C., −11° C., −10° C., −9° C., −8° C., −7° C., −6° C., −5° C., −4° C., −3° C., −2° C., −1° C., 0° C., 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., or 50° C. and then retains a certain percentage of its stability, activity, sensitivity, fidelity, yield, or other property. The exposure to the temperature may be short-term or long-term. The exposure to a temperature may be for at least 1, 2, 3, 4, 5, 10, 15, 20, 25, 30, 35, 40, 45, 50, 55, or 60 minutes. The exposure to the temperature may be for at least 1, 2, 3, 4, 5, 6, 7, 8, 9, 10, 11, 12, 13, 14, 15, 16, 17, 18, 19, 20, 21, 22, 23, or 24 hours, at least 1, 2, 3, 4, 5, or 6 days, or at least 1, 2, 3, 4, 5, 6, 7, 8, 9, or 10 weeks, or for at least 1, 2, 3, 4, 5, 6, 7, 8, 9, 10, 11, or 12 months, or for at least 1, 2, 3, 4, 5, 6, 7, 8, 9, or 10 years. In some cases, the temperature is room temperature (e.g., about 20° C. to 22° C.). In some cases, the polymerase is exposed to room temperature for at least 1, 2, 3, 4, 5, 6, 7, 8, 9, or 10 weeks. For example, the polymerase (e.g., Taq) may be exposed to room temperature or at least 35° C. for at least 4 weeks, at least 6 weeks, at least 10 weeks, or at least 15 weeks.

In one example, FIG. 1 depicts the activity of a Taq polymerase fused to a peptide either after storage at −20° C. or after storage at +35° C. for 4 weeks. The top panel shows the polymerase activity when the polymerase is stored at −20° C.; the lower panel shows the polymerase activity of peptide-fusion polypeptide after being stored at 35° C. for 4 weeks. As shown in FIG. 1, the Taq polymerase fusion enzyme exhibits similar activity after being stored under both conditions.

Polypeptides

In some embodiments, a composition described herein (e.g., the peptide of SEQ ID NO: 1, SEQ ID NO:8 or SEQ ID NO: 10 or SEQ ID NO: 13, or fragments, variants, or mutants thereof) may be linked to a variety of polypeptides, proteins, enzymes, or peptides.

In some embodiments, a peptide tag described herein may be linked to any enzyme useful for a polymerase chain reaction (PCR), the method of K. B. Mullis, e.g., as described in U.S. Pat. Nos. 4,683,195 4,683,202, and 4,965,188 and any other improved method known in the art. PCR is a method for increasing the concentration of a segment of a target sequence in a mixture of DNA without cloning or purification. This process for amplifying the target sequence typically consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one cycle) to obtain a high concentration of an amplified segment of the desired target sequence.

In some embodiments, various polymerases may be linked to the peptide tags described herein. Such polymerases include Taq polymerase (useful e.g. in polymerase chain reaction (PCR) assays), DNA polymerase I (useful e.g. in nick-translation and primer-extension assays), Klenow polymerase (useful e.g. in random-primer labeling), Terminal deoxynucleotidyl transferase (TdT) (useful e.g. for 3′-end labeling), Reverse transcriptase (e.g. for synthesizing DNA from RNA templates) or other polymerases such as SP6 RNA polymerase, T3 RNA polymerase and T7 RNA polymerase for in vitro transcription.

In some embodiments, a peptide tag described herein may be linked to a DNA-dependent DNA polymerase, which is an enzyme that synthesizes a complementary DNA copy from a DNA template by adding a nucleotide to the 3′ end of a newly-forming strand. Some DNA polymerases also have proof-reading ability, which is conferred by 3′ to 5′ exonuclease activity.

In some embodiments, DNA-dependent DNA polymerases provided herein may be the naturally occurring enzymes isolated from bacteria or bacteriophages or expressed recombinantly, or may be modified or have evolved forms which have been engineered to possess certain desirable characteristics, e.g., thermostability, or the ability to recognize or synthesize a DNA strand from various modified templates. DNA-dependent DNA polymerases require a complementary primer to initiate synthesis. It is known that under suitable conditions a DNA-dependent DNA polymerase may synthesize a complementary DNA copy from an RNA template. RNA-dependent DNA polymerases (described herein) typically also have DNA-dependent DNA polymerase activity.

Non-limiting examples of DNA polymerases include *Thermus aquaticus* (Taq) DNA polymerase, *E. coli* DNA polymerase I, *Thermus thermophilus* (Tth) DNA polymerase, *Bacillus stearothermophilus* DNA polymerase, *Thermococcus littoralis* DNA polymerase, bacteriophage T7 DNA polymerase, *Thermococcus gorgonarius* (Tgo) polymerase, Pfu polymerase, Klenow fragment of *E. coli* DNA polymerase, Tma DNA polymerase, exo-Tli DNA polymerase, exo-KOD DNA polymerase, exo-JDF-3 DNA polymerase, exo-PGB-D DNA polymerase, U1Tma (N-truncated) *Thermatoga martima* DNA polymerase, or DNA polymerases from bacteriophages T4, Phi-29, M2, or T5.

In some embodiments, where desired, temperature stable polymerases may be linked to a peptide tag disclosed herein. See, e.g., U.S. Pat. No. 4,889,818 that discloses a representative thermostable enzyme isolated from *Thermus aquaticus*. Additional representative temperature stable polymerases include without limitation, e.g., polymerases extracted from bacteria such as *Thermus aquaticus* DNA polymerase I (Taq), *Thermococcus gorgonarius* (Tgo), *Pyrococcus horikoshii, Pyrococcus furiosus, Pyrococcus woesei, Thermus filiformis, Thermus flavus, Thermus ruber, Thermus thermophilus, Bacillus stearothermophilus* (which has a somewhat lower temperature optimum than the others listed), *Thermus lacteus, Thermus rubens, Thermotoga maritima, Thermococcus littoralis,* and *Methanothermus fervidus.*

In some cases, a peptide tag described herein is linked to a thermostable enzyme that may or may not necessarily have polymerase activity (e.g., *Thermoplasma acidophilum* pyrophosphatase (TAPP), pyrophosphatase, dCTP deaminase (CDA), deoxycytidine deaminase, cytidine deaminase, RNA deaminase, DNA deaminase). In some cases, a peptide tag (e.g., the peptide of SEQ ID NO: 1 or 8), is linked to a nonthermostable polypeptide (e.g., human Leukemia Inhibitor Factor (hLIF), leptin).

In some embodiments, a peptide tag described herein may be linked to polymerases that exhibit strand-displacement activity (also known as rolling circle polymerization). Strand displacement can result in the synthesis of tandem copies of a circular DNA template, and is particularly useful in isothermal PCR reaction. Non-limiting examples of suitable rolling circle polymerases provided herein include but are not limited to T5 DNA polymerase (Chatterjee et al., Gene 97:13-19 (1991)), and T4 DNA polymerase holoenzyme (Kaboord and Benkovic, Curr. Biol. 5:149-157 (1995)), phage M2 DNA polymerase (Matsumoto et al., Gene 84:247 (1989)), phage PRD1 DNA polymerase (Jung et al., *Proc. Natl. Aced. Sci. USA* 84:8287 (1987), and Zhu and Ito, *Biochim. Biophys. Acta.* 1219:267-276 (1994)), Klenow fragment of DNA polymerase I (Jacobsen et al., *Eur. J. Biochem.* 45:623-627 (1974)).

One example of a class of rolling circle polymerases utilizes protein priming as a way of initiating replication. Exemplary polymerases of this class are modified and unmodified DNA polymerase, chosen or derived from the phages ÿ29, PRD1, Cp-1, Cp-5, Cp-7, ÿ45, ÿ1, ÿ21, ÿ25, BS 32 L17, PZE, PZA, Nf, M2Y (or M2), PR4, PR5, PR722, B103, SFS, GA-1, and related members of the Podoviridae family.

In some embodiments, a peptide tag described herein may be linked to a DNA-dependent RNA polymerase or transcriptase, which is an enzyme that synthesizes multiple RNA copies from a double-stranded or partially-double-stranded DNA molecule having a promoter sequence that is usually double-stranded. The RNA molecules are synthesized in the 5'-to-3' direction beginning at a specific position just downstream of the promoter. Examples of transcriptases are the DNA-dependent RNA polymerase from *E. coli* and bacteriophages T7, T3, and SP6.

In some embodiments, a peptide tag described herein may be linked a RNA-dependent DNA polymerase or reverse transcriptase (RT), which is an enzyme that synthesizes a complementary DNA copy from an RNA template. In this method, reverse transcription is coupled to PCR, e.g., as described in U.S. Pat. No. 5,322,770. In RT-PCR, the RNA template is converted to cDNA due to the reverse transcriptase activity of an enzyme, and then amplified using the polymerizing activity of the same or a different enzyme. All known reverse transcriptases also have the ability to make a complementary DNA copy from a DNA template; thus, they are both RNA- and DNA-dependent DNA polymerases. RTs may also have an RNAse H activity. Both thermostable and thermolabile reverse transcriptase and polymerase can be used.

A common reverse transcriptase can be derived from Maloney murine leukemia virus (MMLV-RT). The peptide tags described herein may be linked to polypeptides having reverse transcriptase activity including but not limited to: Moloney Murine Leukemia Virus (M-MLV) reverse transcriptase, Rous Sarcoma Virus (RSV) reverse transcriptase, Avian Myeloblastosis Virus (AMV) reverse transcriptase, Rous-Associated Virus (RAV) reverse transcriptase, Myeloblastosis Associated Virus (MAV) reverse transcriptase, Human Immunodeficiency Virus (HIV) reverse transcriptase, Avian Sarcoma-Leukosis Virus (ASLV) reverse transcriptase, retroviral reverse transcriptase, retrotransposon reverse transcriptase, hepatitis B reverse transcriptase, cauliflower mosaic virus reverse transcriptase, bacterial reverse transcriptase, *Thermus thermophilus* (Tth) DNA polymerase, *Thermus aquaticus* (Taq) DNA polymerase, *Thermotoga neopolitana* (Tne) DNA polymerase, *Thermotoga maritima* (Tma) DNA polymerase, *Thermococcus litoralis* (Tli or VENTR™) DNA polymerase, *Pyrococcus furiosus* (Pfu) DNA polymerase, DEEPVENT™, *Pyrococcus* species GB-D DNA polymerase, *Pyrococcus woosii* (Pwo) DNA polymerase, *Bacillus sterothermophilus* (Bst) DNA polymerase, *Bacillus caldophilus* (Bca) DNA polymerase, *Sulfoloblus acidocaldarius* (Sac) DNA polymerase, *Thermoplasma acidophilum* (Tac) DNA polymerase, *Thermus flavus* (Tfl/Tub) DNA polymerase, *Thermus ruber* (Tru) DNA polymerase, *Thermus brockianus* (DYNAZYME™) DNA polymerase, *Methanobacterium thermoautotrophicum* (Mth) DNA polymerase, and mutants, variants and derivatives thereof.

In some embodiments, a peptide tag described herein may be linked to an amylase. Non-limiting examples of amylases include those from *Bacillus amyloliquefaciens*, *Bacillus licheniformis*, *Bacillus stearothermophilus*, *Bacillus subtilis*, *Lactobacillus manihotivorans*, *Myceliophthora thermophila*, *Pyrococcus furiosus*, *Pyrococcus woesei*, *Staphylothermus marinus*, *Sulfolobus solfataricus*, *Thermococcus aggreganes*, *Thermococcus fumicolans*, *Thermococcus hydrothermalis*, *Thermomyces lanuginosas*, *Thermococcus profoundus*, *Bacillus ciculans*, *Bacillus cereus* var. *Mycoides*, and *Clostridium thermosulphurogenes*.

In some embodiments, a peptide tag described herein may be linked to a pullulanase. Non-limiting examples of pullulanases include those from *Bacillus* sp., *Pyrococcus furiosus*, *Pyrococcus woesi*, *Thermococcus aggregans*, *Thermus caldophilus* GK24, *Thermococcus celer*, *Thermococcus hydrothermalis*, *Thermococcus litoralis*, and *Thermotoga maritima* MSB8.

In some embodiments, a peptide tag described herein may be linked to a xylanase. Non-limiting examples of xylanases include those from *Bacillus amyloliquefaciens*, *Bacillus circulans*, *Bacillus* sp. Strain SPS-0, *Bacillus subtilis*, *Clostridium abosum*, *Dictyoglomus* sp. Strain $B_1$, *Fusarium proliferatum*, *Pyrococcus furiosus*, *Scytalidium thermophilum*, *Streptomyces* sp. Strain S38, *Sulfolobus solfataricus*, *Teheromyces lanuginosus*, *Thermoasus aurantiacus*, *Thermotoga maritima* MSB8, *Thermotoga neapolitana*, *Thermotoga* sp. Strain FjSS3-B1, and *Thermotoga thermarum*.

In some embodiments, a peptide tag described herein may be linked to a cellulase. Non-limiting examples of cellulases include those from *Anaerocellu thermophilum*, *Bacillus subtilis*, *Pyrococcus furiosus*, *Pyrococcus horicoshi*, *Rhodothermus marinus*, *Thermotoga maritema* MSB8, and *Thermotoga neapoltana* (Endocellulase A or B).

In some embodiments, a peptide tag described herein may be linked to a proteolytic enzyme. Non-limiting examples of proteolytic enzymes include those from *Bacillus brevis*, *Bacillus licheniformis*, *Bacillus stearothermophilus*, *Bacillus* sp. JB-99, *Bacillus stearothermophilus* TP26, *Bacillus* sp. No. AH-101, *Bacillus thermoruber*, *Pyrococcus* sp. KODI, *Staphylothermus marinus*, *Thermoacidophiles*, *Thermococcus aggreganes*, *Thermococcus celer*, *Thermococcus litoralis*, and *Thermotoga maritema*.

In some embodiments, a peptide tag described herein may be linked to a lipase. Non-limiting examples of lipases include those from *Bacillus acidocaldarius*, *Bacillus* sp. RSJ-1, *Bacillus strin* J33, *Bacillus stearothermophilus*, *Bacillus thermocatenletus*, *Bacillus thermoleovorans* ID-1, *Geobacillus* sp., *Pseudomonas* sp., *Pyrobaculum calidifontis*, *Pyrococcus furiosus*, and *Pyrococcus horikoshii*.

In some cases, one or more of the following polymerases are linked to a peptide tag encoded by SEQ ID NO: 3, by SEQ ID NO: 7, or by SEQ ID NO: 9, or other peptide tag described herein: G46E E678G CS5 DNA polymerase, a G46E L329A E678G CS5 DNA polymerase, G46E E678G CS6 DNA polymerase, ΔZO5R DNA polymerase, ZO5 polymerase, E615G Taq DNA polymerase, *Thermus flavus* (Tfl) polymerase (e.g., a modified Tfl polymerase that incorporates the T-terminator nucleotides described herein), *Thermatoga maritime*- or Tma-25 polymerase, Tma-30 polymerase, *Thermus thermo-*

*philics* (Tth) DNA polymerase, Pfu DNA polymerase, Pfx DNA polymerase, *Thermus* specie SPS-17 polymerase, E615G Taq polymerase, *Thermus* ZO5R polymerase, T7 DNA polymerase, Kornberg DNA polymerase I or *E. coli* DNA Polymerase I, Klenow DNA polymerase, Taq DNA polymerase, Micrococcal DNA polymerase, alpha DNA polymerase, reverse transcriptase, AMV reverse transcriptase, M-MuLV reverse transcriptase, DNA polymerase, RNA polymerase, *E. coli* RNA polymerase, SP6 RNA polymerase, T3 RNA polymerase, T4 DNA polymerase, T7 RNA polymerase, RNA polymerase II, terminal transferase, polynucleotide phosphorylase (PNP), ribonucleotide incorporating DNA polymerase, or the like. In some cases, a proofreading enzyme is linked to to a polypeptide encoded by SEQ ID NO: 3, or to a polypeptide encoded by SEQ ID NO: 7. Alternative, any polymerase (e.g., a polymerase described herein), may be linked to a fragment of a polypeptide encoded by SEQ ID NO: 7 or SEQ ID NO: 9, e.g., to double stranded-binding protein (DSP).

In some embodiments, peptide tags (or structures) provided herein may also provide stability to polypeptides that are not polymerases. The peptide tags may aid the retention of any activity of a polypeptide, e.g., binding activity, enzymatic activity, especially when the polypeptide is exposed to a temperature (e.g., room temperature) for a certain period of time. For example, the peptide tags described herein may be linked to erythropoietin (EPO) (also known as hematopoietin or hemopoietin), for instance, to enhance its stability at room temperature. EPO is a glycoprotein hormone that controls erythropoiesis, or red blood cell production. It is a cytokine for erythrocyte (red blood cell) precursors in the bone marrow. Purified forms of EPO can be used to treat diseases such as anemia or neurological diseases (e.g., schizophrenia). Types of EPO available on the market include but are not limited to erythropoietin (Epoeitin-alpha™) and Darbepoietin-alpha™. Trade names include, but are not limited to: Epogen™; Epoetin™, Procrit™, Eprex™, NeoRecormon™, Darbepoetin™, Epoetin Delta™, PDpoetin™, Aranesp™, and Methoxy polyethylene glycol-epoetin beta (Mircera™).

EPO is encoded by a single-copy gene which has five exons. The human and mouse EPO genes have 90% similar sequences immediately upstream of the transcription start site, 80% in the coding regions, and 65% in the first intron. The locations of introns and splice donor and acceptor sites are conserved between human and mouse EPO genes. The mRNA for EPO contains both 5' and 3' untranslated regions and codes for a leader peptide sequence and a predicted mature EPO protein of 166 amino acids for human and mouse, and 168 amino acids for monkey. The secreted form of human EPO, both the naturally occurring EPO recovered from urine (uh-EPO0 or the recombinant EPO (rh-EPO) expressed in Chinese hamster ovary (CHO) cells, lacks the C-terminal arginine, which is removed by postranslational cleavage. Mature human EPO protein comprises 165 amino acids and has a molecular weight of 34 kDa, with glycosyl residues contributing about 40% of the weight of the molecule. The EPO molecule comprises four helices that interact via their hydrophobic domains to form a predominantly globular structure within an aqueous environment (Cheetham et al., 1998, *Nat. Struct. Biol.* 5:861-866). Human and murine EPO have four cysteines and monkey EPO has five. Internal disulfide bridges exist in human EPO, between Cys7 and Cys161, and between Cys29 and Cys33. At least one of these disulfide bridges is important in the secondary structure.

EPO initiates erythropoiesis by binding to the extracellular portion of a preformed erythropoietin receptor (EPOR) homodimer (i.e., $(EPOR)_2$) in a manner that bridges between specific locations on the individual EPOR subunits. When EPO binds to the $(EPOR)_2$, large portions of the globular ligand are remote from the binding regions and face outward, away from the complex of EPO and $(EPOR)_2$ into the aqueous medium. Human EPO has four glycosylation sites: a single O-lined site at Ser126 and three N-linked sites at Asn24, Asn38, and Asn83. The N-linked glycosylation sites are conserved in murine and monkey EPO. The oligosaccharide chains of human EPO are fucose-containing, sialylated tetraantennary oligosaccharides, some of which contain repeated N-acetyllactoseamines. The remaining N-linked oligosaccharides are triantennary and biantennary oligosaccharides.

In some embodiments, polypeptides, fusion polypeptides, or compositions provided herein comprise EPO in its native form. In some embodiments, polypeptides, fusion polypeptides, or compositions comprise EPO with one or more mutations. In some embodiments, polypeptides, fusion polypeptides, or compositions comprise EPO with one or more mutations at the four glycosylation sites: a single O-lined site at Ser126 and three N-linked sites at Asn24, Asn38, and Asn83. In some embodiments, polypeptides, fusion polypeptides, or compositions comprise EPO with one or more mutations at the four helices. In some embodiments, polypeptides, fusion polypeptides, or compositions comprise EPO with one or more mutations at the residues that form the disulfide bridges: at Cys7, Cys161, Cys29, and Cys33. In some embodiments, the EPO mutations may comprise conserved or non-conserved amino acid substitution, deletion, or addition.

In some embodiments, any protein therapeutic may be linked to a peptide tag disclosed herein. A summary of protein therapeutics can be found in Leader et al. (2008) *Nature Review/Drug Discovery* 7: 21-39. Examples of protein therapeutics include protein therapeutics with enzymatic or regulatory activity, protein therapeutics with special targeting activity, protein vaccines, and protein diagnostics.

In some embodiments, polypeptides, fusion polypeptides, or compositions provided herein comprise a cosmetic peptide or polypeptide. In some embodiments, the cosmetic peptide or polypeptide includes, but not limited to, epidermal growth factor (EGF), keratinocyte growth factor (KGF), vascular endothelial growth factor (VEGF), fibroblast growth factor (FGF), granulocyte-colony stimulation factor (G-CSF), growth differentiation factor 9 (GDF9), hepatocyte growth factor (HGF), hepatoma derived growth factor (HDGF), insulin-like growth factor (IGF), nerve growth factor (NGF), thrombopoietin, transforming growth factor alpha (TGF-α), transforming growth factor beta (TGF-β) placental growth factor, human bone morphogenetic protein (BMP), BMP2, BMP7, platelet-derived growth factor (PDGF), collagenase, gelatinase, matrix metalloproteinase-1, -2, -3, -7, -8, -9, -10, -11, -12, -13, -14, -15, -16, -17, -18, -19, -20, -21, -23A, -23B, -24, -25, -26, -27, or -28.

Examples of protein therapeutics with enzymatic or regulatory activity, include therapeutics for treating: endocrine disorders (e.g., insulin, Growth hormone (GH) somatotropin, Salmon calcitonin, human parthyroid hormone residues 1-34); haemostasis and thrombosis disorders (e.g., Factor VIIa, VIII, Factor IX, Antithrombin III, Protein C concentrate, tissue plasminogen activator (tPA), urokinase); metabolic deficienices (e.g., beta-gluco-cerebrosidase, alpha-L iduronidase); pulmonary and gastrointestinal disorders (e.g., alpha-1-proteinase inhibitor, lactase, pancreatic enzymes); immunodeficiency disorders (e.g., adenosine deaminase, pooled immunoglobulins); blood disorders (e.g., Human albumin, erythropoietin, as described herein); fertility (human follicle stimulating hormone (FSH), Human chorionic gonadotropin (HCH), Lutropin-alpha); immunoregulation (e.g., interferon (IFN), granulocyte macrophage colony stimulating factor (GM-CSF), type 1 alpha-IFN, IFN-beta, IFN-gamma, IFN-gamma1beta, interleukin-1, interleukin-2, interleukin-3, interleukin-4, interleukin-5, interleukin-6, interleukin-7, interleukin-8, interleukin-9, interleukin-10, interleukin-11, interleukin-12, interleukin-13, interleukin-14, interleukin-15, interleukin-16, interleukin-17, interleukin-18, interleukin-19, interleukin-20, interleukin-21, interleukin-22, interleukin-23, interleukin-24, interleukin-25, interleukin-26, interleukin-27, interleukin-28, interleukin-29, interleukin-30, interleukin-31, interleukin-32, interleukin-33, interleukin-34, interleukin-35); growth regulation (e.g., vascular endothelial growth factor (VEGF), epidermal growth factor (EGF), fibroblast growth factor (FGF), granulocyte-colony stimulation factor (G-CSF), growth differentiation factor 9 (GDF9), hepatocyte growth factor (HGF), hepatoma derived growth factor (HDGF), insulin-like growth factor (IGF), nerve growth factor (NGF), thrombopoietin, transforming growth factor alpha (TGF-α), transforming growth factor beta (TGF-β) placental growth factor, human bone morphogenetic protein (BMP), BMP2, BMP7, platelet-derived growth factor (PDGF)). Other protein therapeutics include proteolytic therapeutics (e.g., trypsin), Nesiritide; botulinum toxin type A or B, collagenase, human deoxyribonuclease I, dornase alpha, hyaluronidase, papain, L-asparaginase, humanized antibodies (e.g., bevacizumab (Avastin™), rituximab, trastuzumab); enfuvirtide, abciximab, protein vaccines (e.g., HBsAg vaccine, HPV vaccine, OspA), and anti-rhesus IgG.

In some embodiments, protein diagnostics may also be linked to the peptide tags described herein. Examples include but are not limited to: glucagon, growth hormone releasing hormone, imaging agents for cancer and other diseases, and HIV antigens and HCV antigens.

In some embodiments, polypeptides linked to the peptide tags described herein may be fibrous proteins or globular proteins. Types of proteins to which the peptide tags can be linked include, without limitation: Cytoskeletal proteins (e.g. actin, Arp2/3, Coronin, dystrophin, FtsZ %, keratin, myosin, Spectrin, Tau (protein), tubulin); extracellular matrix proteins (e.g., collagen, elastin, F-spondin, Pikachurin); plasma protein (e.g., serum albumin, Serum Amyloid P Component); coagulation factors (e.g., complement proteins, C1-inhibitor, C3-convertase, Factor VIII, Factor IX, Factor XIII, Fibrin, protein C, Protein S, Protein Z, Protein Z-related protease inhibitor, thrombin, von Willebrand Factor); acute phase proteins (e.g., C-reactive protein); hemoproteins; cell adhesion proteins (e.g., cadherin, integrin, NCAM, selectin); transmembrane transport proteins (e.g., CFTR, glychophorin D, scramblase); ion channels (e.g., acetylcholine receptor); G-protein coupled receptors; potassium channels; synport/antiport proteins; hormones and growth factors (e.g., epidermal growth factor, insulin, insulin-like growth factor, oxytocin, follicle stimulating hormone, leutinizing hormone); transcription regulatory proteins (e.g., MyoD, C-myc); nutrient storage/transport proteins (e.g., ferritin); immunoglobulins; trypsin.

In some embodiments, the polypeptides linked to the peptide tags described herein may be nucleic acid binding peptides (e.g., a peptide capable of binding any nucleic acid, including DNA, RNA, mRNA, cRNA, miRNA, siRNA, cDNA).

In some embodiments, a peptide provided herein is a restriction enzyme. Examples of restriction enzymes include AatII, Acc65I, AccI, AciI, AclI, AcuI, AfeI, AflII, AflIII, AgeI, AhdI, AleI, AluI, AlwI, AlwNI, ApaI, ApaLI, ApeKI, ApoI, AscI, AseI, AsiSI, AvaI, AvaII, AvrII, BaeGI, BaeI, BamHI, BanI, BanII, BbsI, BbvCI, BbvI, BccI, BceAI, BcgI, BciVI, BclI, BfaI, BfuAI, BfuCI, BglI, BglII, BlpI, BmgBI, BmrI, BmtI, BpmI, Bpu10I, BpuEI, BsaAI, BsaBI, BsaHI, BsaI, BsaJI, BsaWI, BsaXI, BseRI, BseYI, BsgI, BsiEI, BsiHKAI, BsiWI, BslI, BsmAI, BsmBI, BsmFI, BsmI, BsoBI, Bsp1286I, BspCNI, BspDI, BspEI, BspHI, BspMI, BspQI, BsrBI, BsrDI, BsrFI, BsrGI, BsrI, BssHII, BssKI, BssSI, BstAPI, BstBI, BstEII, BstNI, BstUI, BstXI, BstYI, BstZ17I, Bsu36I, BtgI, BtgZI, BtsCI, BtsI, Cac8I, ClaI, CspCI, CviAII, CviKI-1, CviQI, DdeI, DpnI, DpnII, DraI, DraIII, DrdI, EaeI, EagI, EarI, EciI, Eco53kI, EcoNI, EcoO109I, EcoP15I, EcoRI, EcoRV, FatI, FauI, Fnu4HI, FokI, FseI, FspI, HaeII, HaeIII, HgaI, HhaI, HincII, HindIII, HinfI, HinP1I, HpaI, HpaII, HphI, Hpy166II, Hpy188I, Hpy188III, Hpy99I, HpyAV, HpyCH4III, HpyCH4IV, HpyCH4V, KasI, KpnI, MboI, MboII, MfeI, MluI, MlyI, MmeI, MnlI, MscI, MseI, MslI, MspA1I, MspI, MwoI, NaeI, NarI, Nb.BbvCI, Nb.BsmI, Nb.BsrDI, Nb.BtsI, NciI, NcoI, NdeI, NgoMIV, NheI, NlaIII, NlaIV, NmeAIII, NotI, NruI, NsiI, NspI, Nt.AlwI, Nt.BbvCI, Nt.BsmAI, Nt.BspQI, Nt.BstNBI, Nt.CviPII, PacI, PaeR7I, PciI, PflFI, PflMI, PhoI, PleI, PmeI, PmlI, PpuMI, PshAI, PsiI, PspGI, PspOMI, PspXI, PstI, PvuI, PvuII, RsaI, RsrII, SacI, SacII, SalI, SapI, Sau3AI, Sau96I, SbfI, ScaI, ScrFI, SexAI, SfaNI, SfcI, SfiI, SfoI, SgrAI, SmaI, SmlI, SnaBI, SpeI, SphI, SspI, StuI, StyD4I, StyI, SwaI, T, TaqαI, TfiI, TliI, TseI, Tsp45I, Tsp509I, TspMI, TspRI, Tth111I, XbaI, XcmI, XhoI, XmaI, XmnI, and ZraI.

In some embodiments, the peptide may also be a homing endonuclease. Examples of homing endonucleases include I-CeuI, I-SceI, PI-PspI, and PI-SceI. The peptide may also be a nicking endonuclease. Examples of nicking endonucleases include Nb.BbvCI, Nb.BsmI, Nb.BsrDI, Nb.BtsI, Nt.AlwI, Nt.BbvCI, Nt.BsmAI, Nt.BspQI, Nt.BstNBI, and Nt.CviPII.

In some embodiments, the peptide is high-fidelity. The peptide can be a high-fidelity variant of any peptide described herein.

In some embodiments, the peptide is a Cell nuclease, a mung bean nuclease, a P1 nuclease, an S1 nuclease. In some embodiments, the peptide is a single-strand specific (sss) nucleases. In some embodiments, the peptide is a nuclease useful for mutational analysis and/or single nucleotide polymorphism analysis. Cell nuclease may be used for mutational analysis and single-nucleotide polymorphism analysis to cleave single base pair mismatches in heteroduplex DNA templates—the TILLING (Targeting Induced Local Lesions IN Genomes) mismatch cleavage method. In other embodiments, the peptide is capable of fastdigestion.

In some embodiments, the peptide linked to a peptide tag described herein can be a deoxyribonuclease, ribonuclease, exonuclease, endonuclease, exodeoxyribonuclease, exoribonuclease, endodeeoxyribonuclease, endoribonuclease, oligonuclease, RecBCD, deoxyribonuclease I, deoxyribonuclease II, deoxyribonuclease IV, UvrABC endonuclease, *aspergillus* nuclease S1, or micrococcal nuclease.

Modified Polypeptides

In some embodiments, polypeptides described herein may be modified in any manner known in the art. For example, the polymerases described herein may be modified for us in Hot Start PCR methods. "Hot Start PCR" is a modified form of conventional polymerase chain reaction (PCR). The polymerases disclosed herein may also be modified to be used in Hot Start PCR methods. Hot Start PCR typically involves the use of a polymerase that is inactivated at lower and ambient temperatures, and that is subsequently activated at higher temperatures, usually during the denaturation step of PCR (e.g., when the reaction reaches a temperature 90 to 105° C., e.g., 95° C.). In some examples, the sample must be incubated for a certain period of time (e.g., more than 1, 5, 7, 10, 15, 20, or 30 minutes) at a specific temperature (e.g., about 85° C., 90° C., 95° C., 100° C., 105° C. or 110° C. For example, the reaction may be incubated for 15 min at 95° C. in order to activate a Hot Start PCR polymerase. The use of such a polymerase prevents extension of non-specifically annealed primers and primer-dimers formed at low temperatures during PCR setup. A Hot Start PCR technique is especially useful for avoiding non-specific amplification of DNA, and increasing sensitivity and yield.

The inhibition of the polymerase used for Hot Start PCR is caused either by an antibody, peptide, or chemical modification. The modification is usually made at active site side chains (e.g. ABgene Thermostart). One example of a chemically-modified polymerase useful for Hot Start PCR is a polymerase modified with an aldehyde modifying reagents, preferably formaldehyde (see, e.g., U.S. Pat. No. 6,183,998). Other examples include polymerases modified via other chemical reactions, such as by an anhydride reaction, and other modifications described in U.S. Pat. No. 5,773,258. Polymerases useful for Hot Start PCR may also be modified by linkage to a polymerase-specific antibody (see, e.g., U.S. Pat. No. 5,338,671). In some cases, polymerases are sequestered from other reagents in a reaction mix, with physical barriers before the thermal cycling takes place. For example, in a wax-barrier method, a wax such as paraffin wax or a paraffin wax bead is used to sequester the polymerase from other reagents in the reaction mix.

In some embodiments, the polymerases disclosed herein may be chemically modified in order to facilitate Hot Start PCR methods, by any method known in the art. (see, e.g., U.S. Pat. No. 5,773,258, U.S. Pat. No. 6,183,998). In some cases, the polymerases are modified with an antibody or peptide in order to facilitate Hot Start PCR methods. In still other cases, a polymerase described herein is sequestered in paraffin wax (e.g., paraffin wax bead).

The reagents necessary for performing Hot Start PCR are packaged in kits that are commercially available. This activation of the polymerase at higher temperatures, such as high temperatures useful for the denaturation step of PCR Polypeptide Variants In some embodiments, polypeptides described in the present disclosure (e.g., polymerases) also include a vast number of sequence variations, mutants, and fragments thereof, that can be generated (e.g., in vitro) and screened for activity and stability. They also include any modified polypeptides that are commercially available (e.g., titanium polymerase (Invitrogen); Taq Gold (Applied Biosystems), etc.). Taq polymerases that are truncated often retain activity. Thus, the polypeptides described herein include N'- and C'-terminal truncations of Taq polymerases. Indeed, they include any Taq polymerase that retains activity.

In order to isolate sequence variants, random mutagenesis of the entire sequence or specific subsequences corresponding to particular domains may be performed. Alternatively, site directed mutagenesis can be performed reiteratively while avoiding mutations to residues critical for protease function. Mutation tolerance prediction programs can be used to greatly reduce the number of non-functional sequence variants that would be generated strictly by random mutagenesis. Various programs for predicting the effects of amino acid substitutions in a protein sequence on protein function (e.g., SIFT, PolyPhen, PANTHER PSEC, PMUT, and TopoSNP) are described in, e.g., Henikoff et al., (2006), Annu. Rev. Genomics Hum. Genet., 7:61-80.

In addition, the present disclosure provides different percentages of sequence identity for the polypeptides described. Percent sequence identity is determined by conventional methods. See, for example, Altschul et al., (1986), Bull. Math. Bio., 48:603, and Henikoff and Henikoff, (1992), Proc. Natl. Acad. Sci. USA, 89:10915. Briefly, two amino acid sequences are aligned to optimize the alignment scores using a gap opening penalty of 10, a gap extension penalty of 1, and the "BLOSUM62" scoring matrix of Henikoff and Henikoff (supra). The percent identity is then calculated as: ([Total number of identical matches]/[length of the longer sequence plus the number of gaps introduced into the longer sequence in order to align the two sequences]) (100).

There are many established algorithms available to align two amino acid sequences. The "FASTA" similarity search algorithm of Pearson and Lipman is a suitable protein alignment method for examining the level of identity shared by an amino acid sequence disclosed herein and the amino acid sequence of another peptide. The FASTA algorithm is described by Pearson et al., (1988), Proc. Nat'l Acad. Sci. USA, 85:2444, and by Pearson (1990), Meth. Enzymol. 183:63. Briefly, FASTA first characterizes sequence similarity by identifying regions shared by the query sequence (e.g., SEQ ID NO:4 or SEQ ID NO: 6 or SEQ ID NO:9) and a test sequence that have either the highest density of identities (if the ktup variable is 1) or pairs of identities (if ktup=2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman et al., (1970), J. Mol. Biol. 48:444; Sellers (1974), SIAM J. Appl. Math., 26:787, which allows for amino acid insertions and deletions. Illustrative parameters for FASTA analysis are: ktup=1, gap opening penalty=10, gap extension penalty=1, and substitution matrix=BLOSUM62. These parameters can be introduced into a FASTA program by modifying the scoring matrix file ("SMATRIX"), as explained in Appendix 2 of Pearson, (1990), Meth. Enzymol., 183:63.

Also provided herein are proteins having a conservative amino acid change, compared with an amino acid sequence disclosed herein. Among the common amino acids, for example, a "conservative amino acid substitution" is illustrated by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine. The BLOSUM62 table is an amino acid substitution matrix derived from about 2,000 local multiple alignments of protein sequence segments, representing highly conserved regions of more than 500 groups of related proteins See Henikoff et al., (1992), Proc. Nat'l Acad. Sci., USA, 89:10915. Accordingly, the BLOSUM62 substitution frequencies can be used to define conservative amino acid substitutions that may be introduced into the amino acid sequences provided herein. Although it is possible to design amino acid substitutions based solely upon chemical properties (as discussed above), the language "conservative amino acid substitution" preferably refers to a substitution represented by a BLOSUM62 value of greater than −1. For example, an amino acid substitution is conservative if the substitution is characterized by a BLOSUM62 value of 0, 1, 2, or 3. According to this system, preferred conservative amino acid substitutions are characterized by a BLOSUM62 value of at least 1 (e.g., 1, 2 or 3), while more preferred conservative amino acid substitutions are characterized by a BLOSUM62 value of at least 2 (e.g., 2 or 3).

It also will be understood that amino acid sequences may include additional residues, such as additional N- or C-terminal amino acids, and yet still be essentially as set forth in one of the sequences disclosed herein, so long as the sequence retains sufficient biological protein activity to be functional in the compositions and methods provided herein.

In some cases, the composition comprises a polypeptide that is at least 10%, 20%, 50%, 70%, 75%, 80%, 85%, 90%, 95%, or 100% identical to a polypeptide encoded by SEQ ID NO: 3, SEQ ID NO:4, SEQ ID NO:5, SEQ ID NO:7, SEQ ID NO:10, SEQ ID NO:12, fragments, mutants or variants thereof.

Pharmaceutical Compositions

Compositions provided herein may be administered as pharmaceutical formulations including those suitable for oral (including buccal and sub-lingual), rectal, intranasal, topical, transdermal, transdermal patch, pulmonary, vaginal, suppository, or parenteral (including intramuscular, intraarterial, intrathecal, intradermal, intraperitoneal, subcutaneous and intravenous) administration or in a form suitable for administration by aerosolization, inhalation or insufflation. General information on drug delivery systems can be found in Ansel et al., Pharmaceutical Dosage Forms and Drug Delivery Systems (Lippencott Williams & Wilkins, Baltimore Md. (1999).

In various embodiments, the pharmaceutical composition includes carriers and excipients (including but not limited to buffers, carbohydrates, mannitol, proteins, polypeptides or amino acids such as glycine, antioxidants, bacteriostats, chelating agents, suspending agents, thickening agents and/or preservatives), water, oils including those of petroleum, animal, vegetable or synthetic origin, such as peanut oil, soybean oil, mineral oil, sesame oil and the like, saline solutions, aqueous dextrose and glycerol solutions, flavoring agents, coloring agents, detackifiers and other acceptable additives, adjuvants, or binders, other pharmaceutically acceptable auxiliary substances as required to approximate physiological conditions, such as pH buffering agents, tonicity adjusting agents, emulsifying agents, wetting agents and the like. Examples of excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. In some embodiments, the pharmaceutical preparation is substantially free of preservatives. In other embodiments, the pharmaceutical preparation may contain at least one preservative. General methodology on pharmaceutical dosage forms is found in Ansel et al., Pharmaceutical Dosage Forms and Drug Delivery Systems (Lippencott Williams & Wilkins, Baltimore Md. (1999). It will be recognized that, while any suitable carrier known to those of ordinary skill in the art may be employed to administer the compositions provided herein, the type of carrier will vary depending on the mode of administration. A thorough discussion of pharmaceutically acceptable carriers/excipients can be found in Remington's Pharmaceutical Sciences, Gennaro, AR, ed., 20th edition, 2000: Williams and Wilkins PA, USA.

Compounds may also be encapsulated within liposomes using well-known technology. Biodegradable microspheres may also be employed as carriers for the pharmaceutical compositions provided herein. Suitable biodegradable microspheres are disclosed, for example, in U.S. Pat. Nos. 4,897,268; 5,075,109; 5,928,647; 5,811,128; 5,820,883; 5,853,763; 5,814,344 and 5,942,252.

The compound may be administered in liposomes or microspheres (or microparticles). Methods for preparing liposomes and microspheres for administration to a patient are well known to those of skill in the art. U.S. Pat. No. 4,789,734, the contents of which are hereby incorporated by reference, describes methods for encapsulating biological materials in liposomes. Essentially, the material is dissolved in an aqueous solution, the appropriate phospholipids and lipids added, along with surfactants if required, and the material dialyzed or sonicated, as necessary. A review of known methods is provided by G. Gregoriadis, Chapter 14, "Liposomes," Drug Carriers in Biology and Medicine, pp. 2.sup.87-341 (Academic Press, 1979).

Microspheres formed of polymers or proteins are well known to those skilled in the art, and can be tailored for passage through the gastrointestinal tract directly into the blood stream. Alternatively, the compound can be incorporated and the microspheres, or composite of microspheres, implanted for slow release over a period of time ranging from days to months. See, for example, U.S. Pat. Nos. 4,906,474, 4,925,673 and 3,625,214, and Jein, TIPS 19:155-157 (1998), the contents of which are hereby incorporated by reference.

The concentration of drug may be adjusted, the pH of the solution buffered and the isotonicity adjusted to be compatible with intravenous injection, as is well known in the art.

The compounds provided herein may be formulated as a sterile solution or suspension, in suitable vehicles, well known in the art. The pharmaceutical compositions may be sterilized by conventional, well-known sterilization techniques, or may be sterile filtered. The resulting aqueous solutions may be packaged for use as is, or lyophilized, the lyophilized preparation being combined with a sterile solution prior to administration. Suitable formulations and additional carriers are described in Remington "The Science and Practice of Pharmacy" (20th Ed., Lippincott Williams & Wilkins, Baltimore Md.), the teachings of which are incorporated by reference in their entirety herein.

The agents or their pharmaceutically acceptable salts may be provided alone or in combination with one or more other agents or with one or more other forms. For example a formulation may comprise one or more agents in particular proportions, depending on the relative potencies of each agent and the intended indication. For example, in compositions for targeting two different host targets and where potencies are similar, about a 1:1 ratio of agents may be used. The two forms may be formulated together, in the same dosage unit e.g., in one cream, suppository, tablet, capsule, aerosol spray, or packet of powder to be dissolved in a beverage; or each form may be formulated in a separate unit, e.g., two creams, two suppositories, two tablets, two capsules, a tablet and a liquid for dissolving the tablet, two aerosol sprays, or a packet of powder and a liquid for dissolving the powder, etc.

The term "pharmaceutically acceptable salt" means those salts which retain the biological effectiveness and properties of the agents provided herein, and which are not biologically or otherwise undesirable. For example, a pharmaceutically acceptable salt does not interfere with the effect of an agent provided herein in preventing, reducing, or destabilizing the formation of a multi-subunit complex, or promoting the disruption of a multi-subunit complex.

Typical salts are those of the inorganic ions, such as, for example, sodium, potassium, calcium, magnesium ions, and the like. Such salts include salts with inorganic or organic acids, such as hydrochloric acid, hydrobromic acid, phosphoric acid, nitric acid, sulfuric acid, methanesulfonic acid, p toluenesulfonic acid, acetic acid, fumaric acid, succinic acid, lactic acid, mandelic acid, malic acid, citric acid, tartaric acid or maleic acid. In addition, if the agent(s) contain a carboxy group or other acidic group, it may be converted into a pharmaceutically acceptable addition salt with inorganic or organic bases. Examples of suitable bases include sodium hydroxide, potassium hydroxide, ammonia, cyclohexylamine, dicyclohexyl-amine, ethanolamine, diethanolamine, triethanolamine, and the like.

A pharmaceutically acceptable ester or amide refers to those which retain biological effectiveness and properties of the agents provided herein, and which are not biologically or otherwise undesirable. For example, the ester or amide does not interfere with the beneficial effect of an agent provided herein in preventing, reducing or destabilizing assembly of the multi-subunit complex, or promoting disruption or elimination of the multi-subunit complex in the cells, or preventing or alleviating one or more signs or pathological symptoms associated with exposure to one or more multi-subunit complexes or insoluble components in a subject. Typical esters include ethyl, methyl, isobutyl, ethylene glycol, and the like. Typical amides include unsubstituted amides, alkyl amides, dialkyl amides, and the like.

Aqueous compositions provided herein comprise an effective amount of a composition of the present invention, which may be dissolved or dispersed in a pharmaceutically acceptable carrier or aqueous medium. A pharmaceutically acceptable carrier used herein may include any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

Exemplary pharmaceutically acceptable carriers for injectable compositions can include calcium salts, for example, such as calcium chlorides, calcium bromides, calcium sulfates, and the like; and the salts of organic acids such as acetates, propionates, malonates, benzoates, and the like. For example, compositions of the invention may be provided in liquid form, and formulated in saline based aqueous solution of varying pH (5-8), with or without detergents such polysorbate-80 at 0.01-1%, or carbohydrate additives, such mannitol, sorbitol, or trehalose. Commonly used buffers include histidine, acetate, phosphate, or citrate. Under ordinary conditions of storage and use, these preparations can contain a preservative to prevent the growth of microorganisms. The prevention of the action of microorganisms can be brought about by various antibacterial and antifungal agents, for example, parabens, chlorobutanol; phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate, and gelatin.

For human administration, preparations meet sterility, pyrogenicity, general safety, and purity standards as required by FDA and other regulatory agency standards. The active compounds will generally be formulated for parenteral administration, e.g., formulated for injection via the intravenous, intramuscular, subcutaneous, intralesional, or intraperitoneal routes. The preparation of an aqueous composition that contains an active component or ingredient will be known to those of skill in the art in light of the present disclosure. Typically, such compositions can be prepared as injectables, either as liquid solutions or suspensions; solid forms suitable for use in preparing solutions or suspensions upon the addition of a liquid prior to injection can also be prepared; and the preparations can also be emulsified.

Sterile injectable solutions are prepared by incorporating the active compounds in the required amount in the appropriate solvent with various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, methods of preparation include vacuum-drying and freeze-drying techniques which yield a powder of the active ingredient plus any additional desired ingredient from a previously sterile-filtered solution thereof.

Upon formulation, solutions will be systemically administered in a manner compatible with the dosage formulation and in such amount as is therapeutically effective based on the criteria described herein. The formulations are easily administered in a variety of dosage forms, such as the type of injectable solutions described above, but drug release capsules and the like can also be employed The appropriate quantity of a pharmaceutical composition to be administered, the number of treatments, and unit dose will vary according to the subject to be treated, and the disease state of the subject. The person responsible for administration will, in any event, determine the appropriate dose for the individual subject.

In addition to the compounds formulated for parenteral administration, such as intravenous or intramuscular injection, other alternative methods of administration of the present invention may also be used, including but not limited to intradermal administration (See U.S. Pat. Nos. 5,997,501; 5,848,991; and 5,527,288), pulmonary administration (See U.S. Pat. Nos. 6,361,760; 6,060,069; and 6,041,775), buccal administration (See U.S. Pat. Nos. 6,375,975; and 6,284, 262), transdermal administration (See U.S. Pat. Nos. 6,348, 210; and 6,322,808) and transmucosal administration (See U.S. Pat. No. 5,656,284). Such methods of administration are well known in the art. One may also use intranasal administration of the present invention, such as with nasal solutions or sprays, aerosols or inhalants. Nasal solutions are usually aqueous solutions designed to be administered to the nasal passages in drops or sprays. Nasal solutions are prepared so that they are similar in many respects to nasal secretions. Thus, the aqueous nasal solutions usually are isotonic and slightly buffered to maintain a pH of 5.5 to 6.5. In addition, antimicrobial preservatives, similar to those used in ophthalmic preparations and appropriate drug stabilizers, if required, may be included in the formulation. Various commercial nasal preparations are known and include, for example, antibiotics and antihistamines and are used for asthma prophylaxis.

Additional formulations, which are suitable for other modes of administration, include suppositories and pessaries. A rectal pessary or suppository may also be used. Suppositories are solid dosage forms of various weights and shapes, usually medicated, for insertion into the rectum or the urethra. After insertion, suppositories soften, melt or dissolve in the cavity fluids. For suppositories, traditional binders and carriers generally include, for example, polyalkylene glycols or triglycerides; such suppositories may be formed from mixtures containing the active ingredient in any suitable range, e.g., in the range of 0.5% to 10%, preferably 1%-2%.

Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations, or powders. In certain defined embodiments, oral pharmaceutical compositions will comprise an inert diluent or assimilable edible carrier, or they may be enclosed in a hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations can contain at least 0.1% of active compound. The percentage of the compositions and preparations may, of course, be varied, and may conveniently be between about 2 to about 75% of the weight of the unit, or between about 25-60%. The amount of active compounds in such therapeutically useful compositions is such that a suitable dosage will be obtained.

The tablets, troches, pills, capsules and the like may also contain the following: a binder, such as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent, methylene and propyl parabens as preservatives, a dye and flavoring, such as cherry or orange flavor. In some embodiments, an oral pharmaceutical composition may be enterically coated to protect the active ingredients from the environment of the stomach; enteric coating methods and formulations are well-known in the art.

Kits/Mixtures/Further Compositions

In some embodiments, the compositions disclosed herein may be directly formulated into compositions (e.g., 5× solution concentration) to be used in techniques requiring the use of a thermostable enzyme, such as compositions for quantitative polymerase chain reactions (qPCR) (e.g., real-time PCR, RT PCT, RT qPCR, probe qPCR, EvaGreen qPCR, HRM).

The kits disclosed herein may comprise a DNA-binding dye, particularly dyes that bind double-stranded DNA and emit a signal such as a fluorescent signal. Nonlimiting examples of DNA binding dyes include EvaGreen™, described in U.S. Pat. No. 7,601,498; LC Green; SYTO9; Chromofy; BEBO; and SYBR Green. Such dyes are particularly useful for quantitative PCR (qPCR) applications.

The kits may comprise a reference dye (e.g., ROX dye), or a quencher dye (e.g., TAMRA). In other cases, FRET may be used. FRET may also be used for the reference dye. In some cases, the FRET dye used for the reference dyes is composed of a fluorophore dye (e.g., FAM) followed by a nucleic acid sequence followed by a dye (e.g., Rox dye). Examples of nucleic acid sequences include deoxynucleotides, such as repetitive dT elements. Examples include, 6, 7, 8, 9, 10, 11, 12, or more dT nucleotides. Other nucleotides (either repeated or mixes of different nucleotides can be used). For example, repeated dA, dC, dG, or dU nucleotides can be used. Non-limiting examples of FRET dyes include the following: 5' FAM-TTTTTTTT-3'ROX (8 dT); 5'FAM-TTTTTTTTT-3'ROX (9 dT); or 5'FAM-TTTTTTTTTT-3'ROX (10 dT) (SEQ ID NO: 99). The FRET phenomen can work at distances from 1-5 nm, up to 10 nM. The T-T distance may be approximately 0.24 to 0.36 nm. The distance between the reference and quencher dye can be between about 0.24 to 0.36 nm. The reference dye can have a nucleotide sequence that positions the FRET pairs at an appropriate distance from each other that allows for FRET to occur. In some embodiments, the expected distance between FRET pairs can be less than about or about 2 to 6 nanometers. In some embodiments, the distance between the FRET pairs can be about or up to about 2.72, 3.06, or 3.4 nm. The distance between the reference and quencher dye can be adjusted by selecting different numbers of repeated nucleotides, e.g., 1, 2, 3, 4; 5, 6, 7, 8, 9, 10, 11, 12, 13, 14, 15, 16, 17, 18, 19, 20, 21, or 22 repeated A, C, T, or G nucleotides. Other reference and quencher dyes may be used, e.g., those described herein.

In some embodiments, the above mentioned reference dyes can be used in a variety of reactions, including reactions for real-time quantitative PCR. It can allow for real-time calculation of curves that account for a passive reference dye. The reference dye can be used in a variety of mixes, including probe mixes, evagreen mixes, and HRM and evagreen mixes. The reference dye can be used at a single concentration across different QPCR machines, e.g., an ABI 7900HT, an ABI7500, and a OneStepPlus. The concentration of reference dye may not need to be adjusted based on the machine in use. Without being limited to theory, the reference dye can be used at a single concentration across multiple machines because the reference dye utilizes the FRET phenomenom.

In some embodiments, the reference dye can have any sequence with a melting temperature of about up to about 10, 11, 12, 13, 14, 15, 16, 17, 18, 19, 20, 21, 22, or 23° C. The reference dye with repeated nucleotides, e.g., repeated thymine nucleotides, can be useful as a reference dye because the nucleotide sequence has a low melting temperature. Low melting temperature may reduce the probability of the reference dye annealing to an undesired moiety. This can reduce the interaction between double labeled oligo nucleotides and a DNA template. This can also reduce the formation of dimers.

The reference dyes can exhibit temperature and pH stability. The reference dyes can retain about or greater than about 60, 70, 80, 90, or 100% effectiveness after incubation at about, up to about, or greater than about −80, −60, −40, −30, −20, −10, 0, 10 20, 30, 40, 50, 60, 70, 80, 90, or 100° C. for 1, 5, 10, 15, 20, 25, 30, 40, 50, 60, 70, 80, 90, or 100 hours. The reference dyes can retain 60, 70, 80, 90, or 100% effectiveness after incubation at about, up to about, or greater than about pH 1, 2, 3, 4, 5, 6, 7, 8, 9, 10, 11, 12, 13, or 14 for 1, 5, 10, 15, 20, 25, 30, 40, 50, 60, 70, 80, 90, or 100 hours.

In some embodiments, the reference dyes can be resistant to bleaching. The reference dyes can retain about or greater than about 50, 60, 70, 80, 90, 100% of its fluorescence emission capability after exposure to ambient light for about or greater than about 1, 2, 5, 10, 30, 60, 90, 120, 180, 240, or 360 minutes.

The kits may also comprise reaction media or buffers. Appropriate reaction media or buffers for kits comprising polymerases permit nucleic acid amplification according to the methods of the invention. Such media and conditions are known to persons of skill in the art, and are described in various publications, such as U.S. Pat. Nos. 5,554,516; 5,716,785; 5,130,238; 5,194,370; 6,090,591; 5,409,818; 5,554,517; 5,169,766; 5,480,784; 5,399,491; 5,679,512; and PCT Pub. No. WO 99/42618. For example, a buffer may be Tris buffer, although other buffers can also be used as long as the buffer components are non-inhibitory to enzyme components of the methods of the invention. The pH is from about 5 to about 11, but may also be from about 6 to about 10, from about 7 to about 9, or from about 7.5 to about 8.5. More acidic and alkaline buffers may also be used.

In some embodiments, the reaction medium can also include bivalent metal ions such as Mg2+ or Mn2+, at a final concentration of free ions that is within the range of from about 0.01 to about 15 mM, or from about 1 to 10 mM. In some embodiments, the reaction medium comprises $MgCl_2$ (e.g. greater than 1, 1.5, 2, 5, 7.5, 10, 15, 20, 25, 30, 40, or 50 mM of MgCl2).

In some embodiments, the reaction medium can also include other salts, such as KCl or NaCl, that contribute to the total ionic strength of the medium. For example, the range of a salt such as KCl is preferably from about 0 to about 125 mM, more preferably from about 0 to about 100 mM, and most preferably from about 0 to about 75 mM. The reaction medium can further include additives that could affect performance of the amplification reactions, but that are not integral to the activity of the enzyme components of the methods. Such additives include proteins such as BSA, single strand binding proteins (for e.g., T4 gene 32 protein), and non-ionic detergents such as NP40 or Triton. Reagents, such as DTT, that are capable of maintaining enzyme activities can also be included. Such reagents are known in the art.

In some embodiments, a buffer of the invention can include 50-80 mM TRIS, pH 8.3-9.0 and 10-20 mM (NH4)2SO4 or 30-50 mM KCl. The pH of the buffer can be adjusted depending on the polymerase. In some embodiments, a higher pH, e.g., a pH about, less than about, or greater than about 8.3, 8.4, 8.5, 8.6, 8.7, 8.8, or 8.9, can be used for a standard polymerase and a lower pH, e.g., a pH about, less than about, or greater than about 8.3, 8.4, 8.5, 8.6, 8.7, 8.8, or 8.9, can be used for a hot start polymerase.

In some embodiments, an Evagreen based real time PCR mix can contain 3 polymerases. The mix can contain a main polymerase. The main polymerase can have a concentration of about, greater than about, or less than about 5, 10, 15, 20, 25, 30, 35, 40, 45, 50, 55, 60, 65, 70, 75, 80, 85, 90, 95, 96, 97, 98, 99, or 100%, which may be wt %, vol %, or mol %, or a percentage of the total polymerase in the mix on a molar, mass, or volume basis. The mix can contain a polymerase with a double strand binding domain integrated between a peptide tag of the invention and a main Taq amino acid sequence, e.g., a main polymerase with a double stranding binding domain. The concentration of such a polymerase can have a concentration of about, greater than about, or less than about 5, 10, 15, 20, 25, 30, 35, 40, 45, 50, 55, 60, 65, 70, 75, 80, 85, 90, 95, or 100%, which may be wt %, vol %, or mol %, or a percentage of the total polymerase in the mix on a molar, mass, or volume basis. The mix can also contain a proofreading polymerase (which may be Tgo based), where the peptide tag is at the N-terminus and the double strand binding domain is at the C-terminus. The concentration of such a polymerase can have a concentration of about, greater than about, or less than about 1, 2, 3, 4, 5, 10, 15, 20, 25, 30, 35, 40, 45, 50, 55, 60, 65, 70, 75, 80, 85, 90, 95, 96, 97, 98, 99, or 100%, which may be wt %, vol %, or mol %, or a percentage of the total polymerase in the mix on a molar, mass, or volume basis. Such polymerases can have a peptide tag without influence on the 3' to 5' exonuclease or proofreading activity of the polymerase.

In some embodiments, a probe mix of the invention can have two polymerases. The main polymerase can be a polymerase with 5' to 3' exonuclease activity. The polymerase can have a peptide tag that doesn't influence the 5' to 3' exonuclease activity. The tag can be located at the n-terminus. The probe mix can also include a polymerase with a double strand binding domain. The double strand binding domain can decrease the 5' to 3' exonuclease activity. The reduction in activity can be about, less than about, or greater than about 1, 5, 10, 15, 20, 25, 30, 35, 40, 45, 50, 55, 60, 65, 70, 75, 80, 85, 90, 95, 96, 97, 98, 99, or 100%.

In some embodiments, a typical master mix for end point PCR can contain 3 polymerases, an additive (for example, BSA—bovine serum albumin), a DNA tracking dye (for example, Bromophenol blue), a DNA sample loading component (for example, glycerol). The 3 polymerases may have the amino acid sequences set out in SEQ ID NO:2, SEQ ID NO:6 and SEQ ID NO:11, respectively. The mix can contain a main polymerase. The main polymerase can have a concentration of about, greater than about, or less than about 5, 10, 15, 20, 25, 30, 35, 40, 45, 50, 55, 60, 65, 70, 75, 80, 85, 90, 95, 96, 97, 98, 99, or 100%, which may be wt %, vol %, or mol %, or a percentage of the total polymerase in the mix on a molar, mass, or volume basis. The mix can contain a polymerase with a double strand binding domain integrated between a peptide tag of the invention and a main Taq amino acid sequence, e.g., a main polymerase with a double stranding binding domain. The concentration of such a polymerase can have a concentration of about, greater than about, or less than about 5, 10, 15, 20, 25, 30, 35, 40, 45, 50, 55, 60, 65, 70, 75, 80, 85, 90, 95, or 100%, which may be wt %, vol %, or mol %, or a percentage of the total polymerase in the mix on a molar, mass, or volume basis. The mix can also contain a proofreading polymerase (which may be Tgo based), where the peptide tag is at the N-terminus and the double strand binding domain is at the C-terminus. The concentration of such a polymerase can have a concentration of about, greater than about, or less than about 1, 2, 3, 4, 5, 10, 15, 20, 25, 30, 35, 40, 45, 50, 55, 60, 65, 70, 75, 80, 85, 90, 95, 96, 97, 98, 99, or 100%, which may be wt %, vol %, or mol %, or a percentage of the total polymerase in the mix on a molar, mass, or volume basis. Such polymerases can have a peptide tag without influence on the 3' to 5' exonuclease or proofreading activity of the polymerase.

In some embodiments, the buffers described herein can include a linear polyacrylamide (LPA). The LPA may increase specificity and sensitivity of an enzyme. The LPA can be added to real-time mixes, including real-time mixes including either Evagreen or any probe, e.g., any probe described herein.

In some embodiments, a buffer can have a $MgCl_2$ concentration of 12.5 mM in a storage buffer and the reaction concentration can be 2.5 mM $MgCl_2$. In other embodiments, the reaction concentration of $MgCl_2$ can be between 1.5 and 2.5 mM. The concentration of a DNA template can be 1 to 50 ng/microliter.

In a reaction using an Evagreen dye, the final reaction concentration of a primer (forward or reverse) can be between 80 and 250 nM. In a reaction not using an Evagreen dye and including a probe, the final concentration of a primer can be 200-400 nM and the final concentration of the probe can be 100 to 250 nM.

In a reaction using a proofreading enzyme, the MgCl2 concentration can be 1.5 mM, the concentration of a primer (forward or reverse) can be 100 to 300 nM, and the concentration of a template DNA can be 5-50 ng/microliter.

Where appropriate, an RNase inhibitor (such as Rnasin) that does not inhibit the activity of the RNase employed in the method can also be included. Any aspect of the methods of the invention can occur at the same or varying temperatures. Preferably, the amplification reactions (particularly, primer extension other than the first and second strand cDNA synthesis steps, and strand displacement) are performed isothermally, which avoids the cumbersome thermocycling process. The amplification reaction is carried out at a temperature that permits hybridization of the primers to the template polynucleotide and primer extension products, and that does not substantially inhibit the activity of the enzymes employed. The temperature can be in the range of about 25° C. to about 85° C., about 30° C. to about 80° C., or about 37° C. to about 75° C.

The oligonucleotide components of the amplification reactions provided herein are generally in excess of the number of target nucleic acid sequence to be amplified. They can be provided at about or at least about any of the following: 10, 102, 104, 106, 108, 1010, 1012 times the amount of target nucleic acid.

In one embodiment, the foregoing components are added simultaneously at the initiation of the amplification process. In another embodiment, components are added in any order prior to or after appropriate timepoints during the amplification process, as required and/or permitted by the amplification reaction. Such timepoints can be readily identified by a person of skill in the art. The enzymes used for nucleic acid amplification according to the methods of the invention can be added to the reaction mixture either prior to the target nucleic acid denaturation step, following the denaturation step, or following hybridization of the primer to the target RNA or DNA, as determined by their thermal stability and/or other considerations known to the person of skill in the art.

The amplification process can be stopped at various timepoints, and resumed at a later time. Said timepoints can be readily identified by a person of skill in the art.

In some embodiments, the compositions may also comprise dNTPs (e.g., greater than 1, 1.5, 2, 5, 7.5, 10, 15, 20, 25, 30, 40, or 50 mM dNTPs). The dNTPs may be ultrapure dNTPs. The dNTPs may comprise dATP, dGTP, dCTP, dTTP, dUTP, or any combination thereof). In come cases, the composition comprises a dye (e.g., blue or yellow dye). In some cases, a buffer comprises a detergent described herein. In some cases, the buffer does not comprise a detergent. In some cases, the buffer contains a high pH. In other embodiments, the buffer has a low or neutral pH. In some cases, the buffer contains $(NH_4)2SO_4$.

In some embodiments, the compositions provided herein may be provided in a solution. The solutions may be formulated at different concentrations. For example, the solution may be 1×, 2×, 3×, 4×, 5×, 10×, or greater than 15× concentration. Further descriptions of formulations of the compositions are provided herein.

Some kits comprise two polymerases. For example, a kit may comprise a polymerase with 5' to 3' exonuclease activity (e.g., SEQ ID NO: 2) at a concentration of about 10%, 20%, 50%, 75%, 80%, 85%, 90%, 95%, 96%, 97%, 98%, 99%, 99.1%, 99.2%, 99.3%, 99.5%, 99.7%, 99.8%, 99.9%, or 100% of the total polymerase concentration. Such kit may comprise a second polymerase (e.g., a polymerase tagged with the peptide of SEQ ID NO: 10) at a concentration of 0.1%, 0.2%, 0.3%, 0.5%, 0.7%, 0.8%, 0.9%, 1%, 2%, 3%, 4%, 5%, 10%, 15%, 20%, 50%, 75%, 80%, 85%, 90%, 95%, or 100% of the total polymerase concentration. In a preferred embodiment, a polymerase with 5' to 3' exonuclease activity (e.g., SEQ ID NO: 2) (or any polypeptide comprising the peptide tag of SEQ ID NO: 1) is present at a concentration of greater than 85%, 90%, 95%, 96%, 97%, 98%, 99%, 99.1%, 99.2%, 99.3%, 99.5%, 99.7%, 99.8%, 99.9% of the total concentration of polymerase, while the second polymerase is present at a concentration less than of 0.1%, 0.2%, 0.3%, 0.5%, 0.7%, 0.8%, 0.9%, 1%, 2%, 3%, 4%, 5%, 10%, 15%. In another preferred embodiment, a fusion polypeptide comprising the peptide tag of SEQ ID NO: 1 is present at a concentration of greater than 85%, 90%, 95%, 96%, 97%, 98%, 99%, 99.1%, 99.2%, 99.3%, 99.5%, 99.7%, 99.8%, 99.9% of the total concentration of polymerase, while the second polypeptide is a polypeptide comprising either the DSP peptide (SEQ ID NO: 10) or two peptide tags (e.g., SEQ ID NO: 8 or SEQ ID NO: 11 (showing two tags in one polymerase)) and is present at a concentration less than of 0.1%, 0.2%, 0.3%, 0.5%, 0.7%, 0.8%, 0.9%, 1%, 2%, 3%, 4%, 5%, 10%, 15%. In still other cases, a wild-type Taq (or any polymerase) is present at 85%, 90%, 95%, 96%, 97%, 98%, 99%, 99.1%, 99.2%, 99.3%, 99.5%, 99.7%, 99.8%, 99.9% of the total concentration of polymerase, while the second polypeptide is a polypeptide comprising either the DSP peptide (SEQ ID NO: 10) or two peptide tags (e.g., SEQ ID NO: 8) or is a polymerase with two peptide tags separated by the polymerase (e.g., SEQ ID NO: 11) and is present at a concentration less than 0.1%, 0.2%, 0.3%, 0.5%, 0.7%, 0.8%, 0.9%, 1%, 2%, 3%, 4%, 5%, 10%, 15%.

In certain embodiments, some kits may comprise three or more polymerases. For example, a kit may comprise a polymerase (e.g., SEQ ID NO: 2 or any polypeptide comprising the peptide tag of SEQ ID NO: 1) at a concentration of about 10%, 20%, 50%, 75%, 80%, 85%, 90%, 95%, 96%, 97%, 98%, 99%, 99.1%, 99.2%, 99.3%, 99.5%, 99.7%, 99.8%, 99.9%, or 100% of the total polymerase concentration. In addition, such kit may comprise a second polymerase such as a polymerase comprising the peptide tag of SEQ ID NO: 8, 10 or 13. And furthermore, such kit may comprise a third polypeptide such as a proof-reading polymerase (e.g., tgo polymerase). Such proof-reading polymerase may comprise the peptide tag of SEQ ID NO: 1, 8, 10, or 13. For example, such proof-reading polymerase may be SEQ ID NO: 11 (FIG. 12). The second and third polypeptides may each be present at a concentration of less than 0.1%, 0.2%, 0.3%, 0.5%, 0.7%, 0.8%, 0.9%, 1%, 2%, 3%, 4%, 5%, 10%, 15%.

In some embodiments, the compositions may also be used in amplifications involving the use of thermostable DNA polymerases such as Taq or Tgo DNA polymerases, or mutants, derivatives or fragments thereof. For example, in some cases, a polypeptide encoded by SEQ ID NO: 5 or SEQ ID NO: 4 or SEQ ID NO: 12 is used in combination with a polymerase (e.g., Taq polymerase) or proof-reading polymerase (e.g., Tgo DNA polymerase) in an amplification. In some cases, the quantity of a polypeptide encoded by SEQ ID NO: 5, or variants, fragments, or mutants thereof, or SEQ ID NO: 4 (or SEQ ID NO: 12), or variants, fragments or mutants thereof, is at least 1-, 2-, 3-, 4-, 5-, 10-, 20-, 25-, 30-, 40-, 50-, 60-, 70-, 80-, 100-, 250-, 500-, 1000-, 5000-, 10,000-, 15,000-, 20,000-, 50,000-, 100,000-, 500,000-, $10^6$, $10^7$, $10^8$, or $10^9$ less than the quantity of a polymerase (e.g., Taq or Tgo DNA polymerase) used in the amplification. Therefore, in some cases, a composition disclosed herein is a mixture of a polypeptide encoded by SEQ ID NO: 5, or variants, fragments, or mutants thereof, or a polypeptide encoded by SEQ ID NO: 4, or variants, fragments, or mutants thereof, and a polymerase (e.g., Taq or Tgo DNA polymerase), wherein the quantity of a polypeptide encoded by SEQ ID NO: 5, or variants, mutants or fragments thereof, or SEQ ID NO: 4, or variants, mutants or fragments thereof, is at least 1-, 2-, 3-, 4-, 5-, 10-, 20-, 25-, 30-, 40-, 50-, 60-, 70-, 80-, 100-, 250-, 500-, 1000-, 5000-, 10,000-, 15,000-, 20,000-, 50,000-, 100,000-, 500,000-, $10^6$, $10^7$, $10^8$, or $10^9$ fold less than the quantity of the polymerase (e.g., Taq or Tgo DNA polymerase). In certain preferred examples, the composition is a mixture of a polypeptide encoded by SEQ ID NO: 4, or variants, mutants or fragments thereof, and a polypeptide encoded by SEQ ID NO: 5, or variants, mutants, or fragments thereof wherein the quantity of polypeptide encoded by SEQ ID NO: 5, or variants thereof, in the mixture is at least 1-, 2-, 3-, 4-, 5-, 10-, 20-, 25-, 30-, 40-, 50-, 60-, 70-, 80-, 100-, 250-, 500-, 1000-, 5000-, 10,000-, 15,000-, 20,000-, 50,000-, 100,000-, 500,000-, $10^6$, $10^7$, $10^8$, or $10^9$ fold less than the quantity of polypeptide encoded by SEQ ID NO: 4, or variants thereof.

In some cases, the concentration of a polypeptide encoded by SEQ ID NO: 5, or variants thereof, or SEQ ID NO: 4, or variants thereof, is at least 1-, 2-, 3-, 4-, 5-, 10-, 20-, 25-, 30-, 40-, 50-, 60-, 70-, 80-, 100-, 250-, 500-, 1000-, 5000-, 10,000-, 15,000-, 20,000-, 50,000-, 100,000-, 500,000-, $10^6$, $10^7$, $10^8$, or $10^9$ fold less than the concentration of a polymerase (e.g., Taq or Tgo DNA polymerase) used in the amplification. Therefore, in some cases, a composition disclosed herein comprises a mixture of a polypeptide encoded by SEQ ID NO: 5, or variants thereof, or a polypeptide encoded by SEQ ID NO: 4, or variants thereof, and a polymerase (e.g., Taq or Tgo DNA polymerase), wherein the concentration of a polypeptide encoded by SEQ ID NO: 5, or variants thereof, or SEQ ID NO: 4, or variants thereof, is at least 1-, 2-, 3-, 4-, 5-, 10-, 20-, 25-, 30-, 40-, 50-, 60-, 70-, 80-, 100-, 250-, 500-, 1000-, 5000-, 10,000-, 15,000-, 20,000-, 50,000-, 100,000-, 500,000-, $10^6$, $10^7$, $10^8$, or $10^9$ fold less than the concentration of the polymerase (e.g., Taq or Tgo DNA polymerase). All of the embodiments disclosed herein may also comprise polypeptides comprising a polypeptide encoded by SEQ ID NO: 7, or mutants, s variants or fragment thereof such as DSP fragment depicted in the figures and/or a polypeptide or polypeptides comprising a polypeptide encoded by SEQ ID NO: 3, or fragments, mutants, or variants thereof.

In some cases, the composition is a mixture of a polypeptide encoded by SEQ ID NO: 5, or fragments, mutants, or variants thereof, and a polypeptide encoded by SEQ ID NO: 4, or variants, mutants or fragments thereof. In some cases, such mixture also further includes a proofreading enzyme (e.g., Tgo DNA polymerase). Therefore, in some cases the composition comprises a polymerase with 5'→3' exonuclease activity as well as an enzyme with 3'→5' proofreading activity.

In some cases the quantity of a polypeptide encoded by SEQ ID NO: 5, or mutants, fragments, or variants thereof, (or of a polypeptide comprising a polypeptide encoded by SEQ ID NO: 7, or fragment thereof such as DSP) in such composition is at least 1-, 2-, 3-, 4-, 5-, 10-, 20-, 25-, 30-, 40-, 50-, 60-, 70-, 80-, 100-, 250-, 500-, 1000-, 5000-, 10,000-, 15,000-, 20,000-, 50,000-, 100,000-, 500,000-, $10^6$, $10^7$, $10^8$, or $10^9$-fold less than the quantity of a polypeptide encoded by SEQ ID NO: 4, or variants thereof, and/or of the proofreading enzyme.

In some cases, a polypeptide is translated as both a short form and a long form. In some cases, a eukaryotic translation initiation factor is used to facilitate translation of a polypeptide. In some cases, the translation occurs in a bacterium.

A kit may comprise one or more compositions described herein as well as instructions instructing the use of said composition. The instructions may include directions for formulating the reaction sample (including the relevant concentration of polymerase, template, primers (reverse and forward), dNTPs, BSA, and H20). The instructions may also include recommendations running the PCR cycle, particularly the denaturation, annealing, and elongation phases. Such instructions may include the temperature conditions and amount of time, or number of cycles, for each step. For example a recommendation for qPCR may be to have an initial denaturation step at 95° C. 15 min (for example, to activate HOT start enzyme); followed by 40 cycles of the following steps: Denaturation 95° C. for 15 sec; Annealing 60°-65° C. for 20 sec; and Elongation 72° C. for 20 sec.

Nucleic Acid Vectors/Cells

The compositions disclosed herein also include nucleic acids and vectors encoding any of the polypeptides described herein. Non-limiting examples of such constructs include constructs comprising the nucleic acid sequence of SEQ ID NO: 3, 4, 5, 7, 9, and/or 12. Still other examples include constructs comprising nucleic acids encoding polypeptides with the amino acid sequences of SEQ ID NO: 1, 2, 6, 8, 10, 11, and/or 13. The compositions also include fragments, variants, and/or mutants of the foregoing.

The nucleic acid constructs may be composed of single-stranded DNA, double-stranded DNA, cDNA, RNA, cRNA. The nucleic acid vectors may be used in any known expression system, e.g., eukaryotic, prokaryotic, in vitro, etc. In preferred embodiments, the nucleic acid vectors are used in a prokaryotic system (e.g, *E. Coli* bacteria) and the nucleic acid vectors carry a strong eukaryotic translation signal. For example, the nucleic acid vectors may carry a strong eukaryotic translation signal such as a Kozak sequence GCCGCC (A/G)CCAUGG (SEQ ID NO: 100), as described in Nakagawa et al. (2007) Nuc. Acids Res. 1-11. (doi:10.1093/nar/gkm1102). For example, the vectors may include the sequence GCCGCCACCATGGTC (SEQ ID NO: 25). The vectors may also include a ribosome binding site (e.g., a sequence such as AGGA). The strong eukaryotic translation signal may enable translation of multiple peptides, starting at different met residues. For example a vector containing a eukaryotic translation signal described herein and a nucleic acid sequence encoding SEQ ID NO: 1, may express both the long form of the peptide (as shown in FIG. 2), as well as the short form of the peptide (FIG. 14, SEQ ID NO: 13). In this example, the short form of the peptide begins at residues MVDDL (SEQ ID NO: 101) of the original sequence shown in SEQ ID NO: 1.

The inclusion of a strong eukaryotic signal in a nucleic acid vector may result in more yield of protein. Surprisingly, this may occur when such a vector is used in a bacterial system, such as when it is expressed in *E. Coli* bacteria. As a result, the yield of protein isolated from the bacteria may be increased by more than 1.5-, 2-, 3-, 4-, 5-, 7-, 10-, 15-, 20-, 30-, or 40-fold. The nucleic vectors may also contain transcriptional control regions known in the art (e.g., promoters, enhancers, operators, etc.).

In some embodiments, provided herein are cells that incorporate one or more of the vectors of the invention. The cell may be a prokaryotic cell or a eukaryotic cell. The cell may be a bacterial cell (e.g. *E. Coli*). In some embodiments, the cell is a eukaryotic cell. In some embodiments, the cell is a mouse myeloma hybridoma cell. In some embodiments, the cell is a Chinese hamster ovary (CHO) cell. Any suitable techniques, as known in the art, may be used to incorporate the vector(s) into the cell. The introduction of a nucleic vector may be by, e.g., permanent integration into the chromosomal nucleic acid, or by, e.g., introduction of an episomal genetic element.

Methods

The compositions disclosed herein can be used in a number of methods. Given the many of the peptides, polypeptide, fusion polypeptide, and compositions described herein have enhanced stability at warmer temperatures, they may be particularly useful for applications where it is not possible to refrigerate or freeze reagents or therapeutics. The peptide tags can thus be used in therapeutics, reagents, or diagnostics, designed for use in remote regions without reliable access to electricity.

In preferred embodiments, the compositions are polymerases and are used in nucleic acid amplifications, such as polymerase chain reaction (PCR). General procedures for PCR are taught in U.S. Pat. No. 4,683,195 (Mullis) and U.S. Pat. No. 4,683,202 (Mullis et al.) and have been described elsewhere herein. Briefly, amplification of nucleic acids by PCR involves repeated cycles of heat-denaturing the DNA, annealing two primers to sequences that flank the target nucleic acid segment to be amplified, and extending the annealed primers with a polymerase. The primers hybridize to opposite strands of the target nucleic acid and are oriented so that the synthesis by the polymerase proceeds across the segment between the primers, effectively doubling the amount of the target segment. Moreover, because the extension products are also complementary to and capable of binding primers, each successive cycle essentially doubles the amount of target nucleic acids synthesized in the previous cycle. This results in exponential accumulation of the specific target nucleic acids at approximately a rate of $2^n$, where n is the number of cycles.

A typical conventional PCR thermal cycling protocol comprises 30 cycles of (a) denaturation at a range of 90° C. to 95° C. for 0.5 to 1 minute, (b) annealing at a temperature ranging from 50° C. to 65° C. for 1 to 2 minutes, and (c) extension at 68° C. to 75° C. for at least 1 minute. Other protocols including but not limited to universal protocol as well as fast cycling protocol can be performed the subject probes as well.

Another variation of the conventional PCR that can be performed with the compositions provided herein is "nested PCR" using nested primers. The method is preferred when the amount of target nucleic acid in a sample is extremely limited for example, where archival, forensic samples are used. In performing nested PCR, the nucleic acid is first amplified with an outer set of primers capable of hybridizing to the sequences flanking a larger segment of the target nucleic acid. This amplification reaction is followed by a second round of amplification cycles using an inner set of primers that hybridizes to target sequences within the large segment.

In some embodiments, compositions disclosed herein can be used in a reverse-transcriptase PCR reaction (RT-PCR), in which a reverse transcriptase first coverts RNA molecules to double stranded cDNA molecules, which are then employed as the template for subsequent amplification in the polymerase chain reaction. In carrying out RT-PCR, the reverse transcriptase is generally added to the reaction sample after the target nucleic acids are heat denatured. The reaction is then maintained at a suitable temperature (e.g., 30° C.-45° C.) for a sufficient amount of time (e.g., 5-60 minutes) to generate the cDNA template before the scheduled cycles of amplification take place. Such reaction is particularly useful for detecting the biological entity whose genetic information is stored in RNA molecules.

In some embodiments, compositions provided herein can also be used in ligase chain polymerase chain reaction (LCR-PCR). The method involves ligating the target nucleic acids to a set of primer pairs, each having a target-specific portion and a short anchor sequence unrelated to the target sequences. A second set of primers containing the anchor sequence is then used to amplify the target sequences linked with the first set of primers. Procedures for conducting LCR-PCR are well known to artisans in the field, and hence are not detailed herein (see, e.g., U.S. Pat. No. 5,494,810).

In addition, the products of a polymerase reaction can be analyzed by any other method known in the art, e.g., HRM, gel electrophoresis, capillary electrophoresis.

qPCR

In some embodiments, polymerases described herein can also be used in quantitative polymerase chain reactions (qPCR). qPCR, also called real-time PCR, may be used to amplify and simultaneously quantify a targeted DNA molecule. qPCR resembles conventional PCR, except that the amplified DNA is detected as the reaction progresses in real time, as opposed to the end of the reaction. Two common methods for detection of products in real-time PCR are: (1) non-specific fluorescent dyes that intercalate with any double-stranded DNA (e.g., EvaGreen and other dyes described herein), and (2) sequence-specific DNA probes consisting of oligonucleotides that are labeled with a fluorescent reporter which permits detection only after hybridization of the probe with its complementary DNA target. TaqMan probes consist of a fluorophore covalently attached to the 5'-end of the oligonucleotide probe and a quencher at the 3'-end. Several different fluorophores (e.g. 6-carboxyfluorescein, acronym: FAM, or tetrachlorofluorescein, acronym: TET) and quenchers (e.g. tetramethylrhodamine, acronym: TAMRA, or dihydrocyclopyrroloindole tripeptide minor groove binder, acronym: MGB) are available. The quencher molecule quenches the fluorescence emitted by the fluorophore when excited by the cycler's light source via FRET (Fluorescence Resonance Energy Transfer). As long as the fluorophore and the quencher are in proximity, quenching inhibits any fluorescence signals.

In some embodiments, real-time PCR is combined with reverse transcription to quantify messenger RNA and Non-coding RNA in cells or tissues. In further embodiments, the present invention provides quantitative evaluation of the amplification process in real-time by methods described herein. Evaluation of an amplification process in "real-time" involves determining the amount of amplicon in the reaction mixture either continuously or periodically during the amplification reaction, and the determined values are used to calculate the amount of target sequence initially present in the sample. There are a variety of methods for determining the amount of initial target sequence present in a sample based on real-time amplification. These include those disclosed by Wittwer et al., "Method for Quantification of an Analyte," U.S. Pat. No. 6,303,305, and Yokoyama et al., "Method for Assaying Nucleic Acid," U.S. Pat. No. 6,541,205. Another method for determining the quantity of target sequence initially present in a sample, but which is not based on a real-time amplification, is disclosed by Ryder et al., "Method for Determining Pre-Amplification Levels of a Nucleic Acid Target Sequence from Post-Amplification Levels of Product," U.S. Pat. No. 5,710,029. The present invention is particularly suited to real-time evaluation, because the production of side-products is decreased, diminished, or substantially eliminated.

Amplification products may be detected in real-time through the use of various self-hybridizing probes, most of which have a stem-loop structure. Such self-hybridizing probes are labeled so that they emit differently detectable signals, depending on whether the probes are in a self-hybridized state or an altered state through hybridization to a target sequence.

Another example of a detection probe having self-complementarity is a "molecular beacon." Molecular beacons include nucleic acid molecules having a target complement sequence, an affinity pair (or nucleic acid arms) holding the probe in a closed conformation in the absence of a target sequence present in an amplification product, and a label pair that interacts when the probe is in a closed conformation. Hybridization of the target sequence and the target complement sequence separates the members of the affinity pair, thereby shifting the probe to an open conformation. The shift to the open conformation is detectable due to reduced interaction of the label pair, which may be, for example, a fluorophore and a quencher (e.g., DABCYL and EDANS). Molecular beacons are disclosed by Tyagi et al., "Detectably Labeled Dual Confirmation Oligonucleotide Probes, Assays and Kits," U.S. Pat. No. 5,925,517, and Tyagi et al., "Nucleic Acid Detection Probes Having Non-FRET Fluorescence Quenching and Kits and Assays Including Such Probes," U.S. Pat. No. 6,150,097, each of which is hereby incorporated by reference herein in its entirety.

Other self-hybridizing probes for use in the present invention are well known to those of ordinary skill in the art. By way of example, probe binding pairs having interacting labels, such as those disclosed by Morrison, "Competitive Homogenous Assay," U.S. Pat. No. 5,928,862 (the contents of which are hereby incorporated by reference herein), might be adapted for use in the present invention. Probe systems used to detect single nucleotide polymorphisms (snps) might also be utilized in the present invention. Additional detection systems include "molecular switches," as disclosed by Arnold et al., "Oligonucleotides Comprising a Molecular Switch," U.S. Provisional Application No. 60/467,517, which enjoys common ownership with the present application and is hereby incorporated by reference herein in its entirety. And other probes, such as those comprising intercalating dyes and/or fluorochromes, might be useful for detection of amplification products in the present invention. See, e.g., Ishiguro et al., "Method of Detecting Specific Nucleic Acid Sequences," U.S. Pat. No. 5,814,447, the contents of which are hereby incorporated by reference herein.

In some embodiments, the signals produced in the qPCR reactions described herein may be detected in a variety of ways. Generally, a change of signal intensity can be detected by any methods known in the art and is generally dependent on the choice of fluorescent group used. It can be performed with the aid of an optical system. Such system typically comprises at least two elements, namely an excitation source and a photon detector. Numerous examples of these elements are available in the art. An exemplary excitation source is a laser, such as a polarized laser. The choice of laser light will depend on the fluorescent group attached to the probe. For most of the fluorescent groups, the required excitation light is within the range of about 300 nm to about 1200 nm, or more commonly from about 350 nm to about 900 nm. Alternatively, compounds of the invention may be excited using an excitation wavelength of about 300 to about 350 nm, 350 to 400 nm, 400 to 450 nm, 450 to 500 nm, 500 to 550 nm, 550 to 600 nm, 600 to 650 nm, 650 to 700 nm, 750 nm to 800 nm, or from 800 nm to 850 nm, merely by way of example. Those skilled in the art can readily ascertain the appropriate excitation wavelength to excite a given fluorophore by routine experimentation (see e.g., The Handbook—'A Guide to Fluorescent Probes and Labeling Technologies, Tenth Edition' (2005) (available from Invitrogen, Inc./Molecular Probes) previously incorporated herein by reference). Where desired, one can employ other optical systems. These optical systems may comprise elements such as optical reader, high-efficiency photon detection system, photo multiplier tube, gate sensitive FET's, nano-tube FET's, photodiode (e.g. avalanche photo diodes (APD)), camera, charge couple device (CCD), electron-multiplying charge-coupled device (EMCCD), intensified charge coupled device (ICCD), and confocal microscope. These optical systems may also comprise optical transmission elements such as optic fibers, optical switches, mirrors, lenses (including microlens and nanolens), collimators. Other examples include optical attenuators, polarization filters (e.g., dichroic filter), wavelength filters (low-pass, band-pass, or high-pass), wave-plates, and delay lines. In some embodiments, the optical transmission element can be planar waveguides in optical communication with the arrayed optical confinements. See, e.g., U.S. Pat. Nos. 7,292,742, 7,181, 122, 7,013,054, 6,917,726, 7,267,673, and 7,170,050. These and other optical components known in the art can be combined and assembled in a variety of ways to effect detection of distinguishable signals.

High Resolution Melt (HRM) analysis can also be used to detect and quantify amplified DNA following a PCR reaction using any of the polymerases described herein. Nonlimiting examples of uses for HRM include: SNP typing/point mutation detection; zygosity testing at a particular locus, and analyzing DNA methylation status.

The polymerases and other compositions described herein may be used in a wide variety of molecular biology applications. Nonlimiting examples include: sequencing reactions; cloning; mutagenesis; gene detection; point mutation detection; subtractive hybridization, and microarrays.

Methods of Manufacturing or Synthesis of Peptides, Polypeptides, or Fusion Polypeptides Peptides, polypeptides, or fusion polypeptides provided herein may be made using recombinant or synthetic techniques well known in the art. In particular, solid phase protein synthesis is well suited to the relatively short length of the peptides, polypeptides, or fusion polypeptides and may provide greater yields with more consistent results. Additionally, the solid phase protein synthesis may provide additional flexibility regarding the manufacture of the peptides, polypeptides, or fusion polypeptides. For example, desired chemical modifications may be incorporated into the peptides, polypeptides, or fusion polypeptides at the synthesis stage: homocitrulline could be used in the synthesis of the peptide as opposed to lysine, thereby obviating the need to carbamylate the peptide following synthesis.

Synthesis

In solid-phase synthesis of a peptide an amino acid with both alpha-amino group and side chain protection is immobilized on a resin. See e.g., Nilsson, B., Soellner, M., and Raines, R. Chemical Synthesis of Proteins, *Annu. Rev. Biomol. Struct.* 2005. 34:91-118; Meldal M. 1997, Properties of solid supports. *Methods Enzymol.* 289:83-104; and Songster M F, Barany G. 1997, Handles for solid-phase peptide synthesis, *Methods Enzymol.* 289:126-74. Typically, two types of alpha-amino-protecting groups are used: an acid-sensitive tert-butoxycarbonyl (Boc) group or a base-sensitive 9-fluorenylmethyloxycarbonyl (Fmoc) group. Wellings D A, Atherton E. 1997. Standard Fmoc protocols. Methods Enzymol. 289:44-67. After the quick and complete removal of these alpha-amino-protecting groups another protected amino acid with an activated carboxyl group can then be coupled to the unprotected resin-bound amine. By using an excess of activated soluble amino acid, the coupling reactions are forced to completion. The cycle of deprotection and coupling is repeated to complete the sequence. With side chain deprotection and cleavage, the resin yields the desired peptide. Guy C A, Fields G B. 1997, Trifluoroacetic acid cleavage and deprotection of resin-bound peptides following synthesis by Fmoc chemistry, *Methods Enzymol.* 289:67-83, and Stewart J M. 1997, Cleavage methods following Boc-based solid-phase peptide synthesis, *Methods Enzymol.* 289:29-44. Additional methods for performing solid phase protein synthesis are disclosed in Bang, D. & Kent, S., 2004, A One-Pot Total Synthesis of Crambin, *Angew. Chem. Int. Ed.* 43:2534-2538; Bang, D., Chopra, N., & Kent, S. 2004, Total Chemical Synthesis of Crambin., *J. Am. Chem. Soc.* 126:1377-1383; Dawson, P. et al., 1994, Synthesis of Proteins by Native Chemical Ligation, *Science,* 266:776-779; Kochendoerfer et al., 2003, Design and Chemical Synthesis of a Homogenous Polymer-Modified Erythropoiesis Protein, *Science,* 299: 884-887.

If necessary, smaller peptides derived from solid phase peptide synthesis may be combined through peptide ligations such as native chemical ligation. In this process, the thiolate of an N-terminal cysteine residue of one peptide attacks the C-terminal thioester of a second peptide to affect transthioesterification. An amide linkage forms after rapid S.fwdarw.N acyl transfer. See Dawson, P. et al. 1994, Synthesis of Proteins by Native Chemical Ligation, *Science,* 266:776-779.

Further, peptides, polypeptides, or fusion polypeptides provided herein may encompass peptidomimetics, peptides including both naturally occurring and non-naturally occurring amino acids, such as peptoids. Peptoids are oligomers of N-substituted glycines, glycoholic acid, thiopronine, sarcosine, and thiorphan. These structures tend to have a general structure of $(-(C=O)-CH_2-NR-)_n$ with the R group acting as the side chain. Such peptoids can be synthesized using solid phase synthesis in accordance with the protocols of Simon et al., Peptoids: A molecular approach to drug discovery, *Proc. Natl. Acad. Sci USA,* 89:9367-9371 (1992); and Li et al., Photolithographic Synthesis of Peptoids, *J. AM. CHEM. SOC.* 2004, 126, 4088-4089. Additionally, provided herein are uses of peptidomimetics or peptide mimetics, non-peptide drugs with properties analogous to those of the template peptide. (Fauchere, J. (1986) *Adv. Drug Res.* 15:29; Veber and Friedinger (1985) TINS p. 32; and Evans et al. (1987) *J. Med. Chem* 30:1229). Synthesis of various types of peptidomimetics has been reviewed for example in: Methods of Organic Chemistry (Houben-Weyl), Synthesis of Peptides and Peptidomimetics—Workbench Edition Volume E22c (Editor-in-Chief Goodman M.) 2004.

Recombinant Techniques

A variety of host-expression vector systems may be utilized to produce the peptides, polypeptides, or fusion polypeptides provided herein. Such host-expression systems represent vehicles by which the peptides, polypeptides, or fusion polypeptides of interest may be produced and subsequently purified, but also represent cells that may, when transformed or transfected with the appropriate nucleotide coding sequences, exhibit the modified gene product in situ. These include but are not limited to, bacteria, insect, plant, mammalian, including human host systems, such as, but not limited to, insect cell systems infected with recombinant virus expression vectors (e.g., baculovirus) containing the peptide, polypeptide, or fusion polypeptide coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing coding sequences; or mammalian cell systems, including human cell systems, e.g., HT1080, COS, CHO, BHK, 293, 3T3, harboring recombinant expression constructs containing promoters derived from the genome of mammalian cells, e.g., metallothionein promoter, or from mammalian viruses, e.g., the adenovirus late promoter; the vaccinia virus 7.5K promoter.

In addition, a host cell strain may be chosen that modulates the expression of the inserted sequences, or modifies and processes the gene product in the specific fashion desired. Such modifications and processing of protein products may be important for the function of the protein. Different host cells have specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product may be used. Such mammalian host cells, including human host cells, include but are not limited to HT1080, CHO, VERO, BHK, HeLa, COS, MDCK, 293, 3T3, and WI38.

For long-term, high-yield production of recombinant peptides, stable expression is preferred. For example, cell lines that stably express the recombinant tissue protective cytokine-related molecule gene product may be engineered. Rather than using expression vectors that contain viral origins of replication, host cells can be transformed with DNA controlled by appropriate expression control elements, e.g., promoter, enhancer, sequences, transcription terminators, polyadenylation sites, and the like, and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci that in turn can be cloned and expanded into cell lines. This method may advantageously be used to engineer cell lines that express the tissue-protective product. Such engineered cell lines may be particularly useful in screening and evaluation of compounds that affect the endogenous activity of the gene product.

Synthesis of Polynucleotides

Any known methods for synthesizing polynucleotides may be used. Solid phase synthesis disclosed by Caruthers et al. in U.S. Pat. No. 4,458,066 may be used. In this technique, the growing DNA chain is attached to an insoluble support via a long organic linker which allows the growing DNA chain to be solubilized in the solvent in which the support is placed. The solubilized, yet immobilized, DNA chain is thereby allowed to react with reagents in the surrounding solvent and allows for the easy washing away of the reagents from the solid support to which the oligonucleotide is attached.

There are several sites on the nucleosides of similar chemical nature, e.g. —OH or hydroxyl groups. However, during oligonucleotide synthesis, the monomer subunits must be attached to the growing oligonucleotide molecule in a site-specific manner. This requires functionalizing a site either on the growing chain or on the incoming base for attachment of the incoming monomer building block to the growing chain. To prevent the incoming monomer from attaching at the wrong site, the wrong sites must be blocked while the correct site is left open to react. This requires the use of protecting groups, which are compounds attached temporarily to a potentially reactive site so as to prevent it from reacting. The protecting group must be stable during said reactions and yet must eventually be removed to yield the original site. The synthesis of oligonucleotides requires several sites to be protected and particular sites must be deprotected while others remain protected. These protecting groups grouped together as a set are termed orthogonal protecting groups.

Solid phase oligonucleotide synthesis protocols typically use a dimethoxytrityl protecting group for the 5' hydroxyl of nucleosides. A phosphoramidite functionality is utilized at the 3' hydroxyl position. The synthesis generally proceeds from the 3' to the 5' of the ribose or deoxyribose sugar component of the phosphoramidite nucleoside in a synthesis cycle which adds one nucleotide at a time to the growing oligonucleotide chain. Beaucage et al. (1981) *Tetrahedron Lett.* 22:1859. In the first step of the synthesis cycle, the "coupling" step, the 5' end of the growing chain is coupled with the 3' phosphoramidite of the incoming monomer to form a phosphite triester intermediate (the 5' hydroxyl of the added monomer has a protecting group so only one new monomer is added to the growing chain per cycle). Matteucci et al. (1981) *J. Am. Chem. Soc.* 103:3185. Next, an optional "capping reaction" is used to stop the synthesis on any chains having an unreacted 5' hydroxyl, which would be one nucleotide short at the end of synthesis. The phosphite triester intermediate is subjected to oxidation (the "oxidation" step) after each coupling reaction to yield a more stable phosphotriester intermediate. Without oxidation, the unstable phosphite triester linkage would cleave under the acidic conditions of subsequent synthesis steps. Letsinger et al. (1976) *J. Am. Chem. Soc.* 98:3655. Removal of the 5' protecting group of the newly added monomer (the "deprotection" step) is typically accomplished by reaction with acidic solution to yield a free 5' hydroxyl group, which can be coupled to the next protected nucleoside phosphoramidite. This process is repeated for each monomer added until the desired sequence is synthesized.

According to some protocols, the synthesis cycle of couple, cap, oxidize, and deprotect is shortened by omitting the capping step or by taking the oxidation step 'outside' of the cycle and performing a single oxidation reaction on the completed chain. For example, oligonucleotide synthesis according to H-phosphonate protocols will permit a single oxidation step at the conclusion of the synthesis cycles. However, coupling yields are less efficient than those for phosphoramidite chemistry and oxidation requires longer times and harsher reagents than amidite chemistry.

The chemical group conventionally used for the protection of nucleoside 5'-hydroxyls is dimethoxytrityl ("DMT"), which is removable with acid. Khorana (1968) *Pure Appl. Chem.* 17:349; Smith et al. (1962) *J. Am. Chem. Soc.* 84:430. This acid-labile protecting group provides a number of advantages for working with both nucleosides and oligonucleotides. For example, the DMT group can be introduced onto a nucleoside regioselectively and in high yield. Brown et al. (1979) *Methods in Enzymol.* 68:109. Also, the lipophilicity of the DMT group greatly increases the solubility of nucleosides in organic solvents, and the carbocation resulting from acidic deprotection gives a strong chromophore, which can be used to indirectly monitor coupling efficiency. Matteucci et al. (1980) *Tetrahedron Lett.* 21:719. In addition, the hydrophobicity of the group can be used to aid separation on reverse-phase HPLC. Becker et al. (1985) *J. Chromatogr.* 326:219.

Methods Related to Treating, Preventing or Diagnosing Disease

In some embodiments, polymerases disclosed herein can be used in numerous applications, including profiling gene expression, identifying sequence variations, detecting microbes, and determining viral load. Given that they are stable at warmer temperatures, they may be particularly useful in kits designed to diagnose disease in warmer climates. In preferred embodiments, the polymerases are used to evaluate infectious disease status (e.g., HIV-1, HIV-2, hepatitis viruses (e.g., hep a, hep b, hep c), malaria) of a subject. The polymerases disclosed herein may be used in kits for detecting such pathogens as well as kits designed to identify viral load. In other cases, the polymerases may be used to diagnose, treat, or provide a prognosis for genetic diseases (e.g., cancers, neurological diseases such as Alzheimer's Disease).

The polymerases may be used to evaluate, treat, diagnose infections caused by numerous viruses including: Abelson leukemia virus, Abelson murine leukemia virus, Abelson's virus, Acute laryngotracheobronchitis virus, Adelaide River virus, Adeno associated virus group, Adenovirus, African horse sickness virus, African swine fever virus, AIDS virus, Aleutian mink disease parvovirus, Alpharetrovirus, Alphavirus, ALV related virus, Amapari virus, Aphthovirus, Aquareovirus, Arbovirus, Arbovirus C, arbovirus group A, arbovirus group B, Arenavirus group, Argentine hemorrhagic fever virus, Argentine hemorrhagic fever virus, Arterivirus, Astrovirus, Ateline herpesvirus group, Aujezky's disease virus, Aura virus, Ausduk disease virus, Australian bat lyssavirus, Aviadenovirus, avian erythroblastosis virus, avian infectious bronchitis virus, avian leukemia virus, avian leukosis virus, avian lymphomatosis virus, avian myeloblastosis virus, avian paramyxovirus, avian pneumoencephalitis virus, avian reticuloendotheliosis virus, avian sarcoma virus, avian type C retrovirus group, Avihepadnavirus, Avipoxvirus, B virus, B19 virus, Babanki virus, baboon herpesvirus, baculovirus, Barmah Forest virus, Bebaru virus, Berrimah virus, Betaretrovirus, Birnavirus, Bittner virus, BK virus, Black Creek Canal virus, bluetongue virus, Bolivian hemorrhagic fever virus, Borna disease virus, border disease of sheep virus, borna virus, bovine alphaherpesvirus 1, bovine alphaherpesvirus 2, bovine coronavirus, bovine ephemeral fever virus, bovine immunodeficiency virus, bovine leukemia virus, bovine leukosis virus, bovine mammillitis virus, bovine papillomavirus, bovine papular stomatitis virus, bovine parvovirus, bovine syncytial virus, bovine type C oncovirus, bovine viral diarrhea virus, Buggy Creek virus, bullet shaped virus group, Bunyamwera virus supergroup, Bunyavirus, Burkitt's lymphoma virus, Bwamba Fever, CA virus, Calicivirus, California encephalitis virus, camelpox virus, canarypox virus, canid herpesvirus, canine coronavirus, canine distemper virus, canine herpesvirus, canine minute virus, canine parvovirus, Cano Delgadito virus, caprine arthritis virus, caprine encephalitis virus, Caprine Herpes Virus, Capripox virus, Cardiovirus, caviid herpesvirus 1, Cercopithecid herpesvirus 1, cercopithecine herpesvirus 1, Cercopithecine herpesvirus 2, Chandipura virus, Changuinola virus, channel catfish virus, Charleville virus, chickenpox virus, Chikungunya virus, chimpanzee herpesvirus, chub reovirus, chum salmon virus, Cocal virus, Coho salmon reovirus, coital exanthema virus, Colorado tick fever virus, Coltivirus, Columbia SK virus, common cold virus, contagious eethyma virus, contagious pustular dermatitis virus, Coronavirus, Corriparta virus, coryza virus, cowpox virus, coxsackie virus, CPV (cytoplasmic polyhedrosis virus), cricket paralysis virus, Crimean-Congo hemorrhagic fever virus, croup associated virus, Cryptovirus, Cypovirus, Cytomegalovirus, cytomegalovirus group, cytoplasmic polyhedrosis virus, deer papillomavirus, deltaretrovirus, dengue virus, Densovirus, Dependovirus, Dhori virus, diploma virus, *Drosophila* C virus, duck hepatitis B virus, duck hepatitis virus 1, duck hepatitis virus 2, duovirus, Duvenhage virus, Deformed wing virus DWV, eastern equine encephalitis virus, eastern equine encephalomyelitis virus, EB virus, Ebola virus, Ebola-like virus, echo virus, echovirus, echovirus 10, echovirus 28, echovirus 9, ectromelia virus, EEE virus, EIA virus, EIA virus, encephalitis virus, encephalomyocarditis group virus, encephalomyocarditis virus, Enterovirus, enzyme elevating virus, enzyme elevating virus (LDH), epidemic hemorrhagic fever virus, epizootic hemorrhagic disease virus, Epstein-Barr virus, equid alphaherpesvirus 1, equid alphaherpesvirus 4, equid herpesvirus 2, equine abortion virus, equine arteritis virus, equine encephalosis virus, equine infectious anemia virus, equine morbillivirus, equine rhinopneumonitis virus, equine rhinovirus, Eubenangu virus, European elk papillomavirus, European swine fever virus, Everglades virus, Eyach virus, felid herpesvirus 1, feline calicivirus, feline fibrosarcoma virus, feline herpesvirus, feline immunodeficiency virus, feline infectious peritonitis virus, feline leukemia/sarcoma virus, feline leukemia virus, feline panleukopenia virus, feline parvovirus, feline sarcoma virus, feline syncytial virus, Filovirus, Flanders virus, Flavivirus, foot and mouth disease virus, Fort Morgan virus, Four Corners hantavirus, fowl adenovirus 1, fowlpox virus, Friend virus, Gammaretrovirus, GB hepatitis virus, GB virus, German measles virus, Getah virus, gibbon ape leukemia virus, glandular fever virus, goatpox virus, golden shinner virus, Gonometa virus, goose parvovirus, granulosis virus, Gross' virus, ground squirrel hepatitis B virus, group A arbovirus, Guanarito virus, guinea pig cytomegalovirus, guinea pig type C virus, Hantaan virus, Hantavirus, hard clam reovirus, hare fibroma virus, HCMV (human cytomegalovirus), hemadsorption virus 2, hemagglutinating virus of Japan, hemorrhagic fever virus, hendra virus, Henipaviruses, Hepadnavirus, hepatitis A virus, hepatitis B virus group, hepatitis C virus, hepatitis D virus, hepatitis delta virus, hepatitis E virus, hepatitis F virus, hepatitis G virus, hepatitis nonA nonB virus, hepatitis virus, hepatitis virus (nonhuman), hepatoencephalomyelitis reovirus 3, Hepatovirus, heron hepatitis B virus, herpes B virus, herpes simplex virus, herpes simplex virus 1, herpes simplex virus 2, herpesvirus, herpesvirus 7, Herpesvirus ateles, Herpesvirus hominis, Herpesvirus infection, Herpesvirus saimiri, Herpesvirus suis, Herpesvirus varicellae, Highlands J virus, Hirame rhabdovirus, hog cholera virus, human adenovirus 2, human alphaherpesvirus 1, human alphaherpesvirus 2, human alphaherpesvirus 3, human B lymphotropic virus, human betaherpesvirus 5, human coronavirus, human cytomegalovirus group, human foamy virus, human gammaherpesvirus 4, human gammaherpesvirus 6, human hepatitis A virus, human herpesvirus 1 group, human herpesvirus 2 group, human herpesvirus 3 group, human herpesvirus 4 group, human herpesvirus 6, human herpesvirus 8, human immunodeficiency virus, human immunodeficiency virus 1, human immunodeficiency virus 2, human papillomavirus, human T cell leukemia virus, human T cell leukemia virus I, human T cell leukemia virus II, human T cell leukemia virus III, human T cell lymphoma virus I, human T cell lymphoma virus II, human T cell lymphotropic virus type 1, human T cell lymphotropic virus type 2, human T lymphotropic virus I, human T lymphotropic virus II, human T lymphotropic virus III, Ichnovirus, infantile gastroenteritis virus, infectious bovine rhinotracheitis virus, infectious haematopoietic necrosis virus, infectious pancreatic necrosis virus, influenza virus A, influenza virus B, influenza virus C, influenza virus D, influenza virus pr8, insect iridescent virus, insect virus, iridovirus, Japanese B virus, Japanese encephalitis virus, JC virus, Junin virus, Kaposi's sarcoma-associated herpesvirus, Kemerovo virus, Kilham's rat virus, Klamath virus, Kolongo virus, Korean hemorrhagic fever virus, kumba virus, Kysanur forest disease virus, Kyzylagach virus, La Crosse virus, lactic dehydrogenase elevating virus, lactic dehydrogenase virus, Lagos bat virus, Langur virus, lapine parvovirus, Lassa fever virus, Lassa virus, latent rat virus, LCM virus, Leaky virus, Lentivirus, Leporipoxvirus, leukemia virus, leukovirus, lumpy skin disease virus, lymphadenopathy associated virus, Lymphocryptovirus, lymphocytic choriomeningitis virus, lymphoproliferative virus group, Machupo virus, mad itch virus, mammalian type B oncovirus group, mammalian type B retroviruses, mammalian type C retrovirus group, mammalian type D retroviruses, mammary tumor virus, Mapuera virus, Marburg virus, Marburg-like virus, Mason Pfizer monkey virus, Mastadenovirus, Mayaro virus, ME virus, measles virus, Menangle virus, Mengo virus, Mengovirus, Middelburg virus, milkers nodule virus, mink enteritis virus, minute virus of mice, MLV related virus, MM virus, Mokola virus, Molluscipoxvirus, Molluscum contagiosum virus, monkey B virus, monkeypox virus, Mononegavirales, Morbillivirus, Mount Elgon bat virus, mouse cytomegalovirus, mouse encephalomyelitis virus, mouse hepatitis virus, mouse K virus, mouse leukemia virus, mouse mammary tumor virus, mouse minute virus, mouse pneumonia virus, mouse poliomyelitis virus, mouse polyomavirus, mouse sarcoma virus, mousepox virus, Mozambique virus, Mucambo virus, mucosal disease virus, mumps virus, murid betaherpesvirus 1, murid cytomegalovirus 2, murine cytomegalovirus group, murine encephalomyelitis virus, murine hepatitis virus, murine leukemia virus, murine nodule inducing virus, murine polyomavirus, murine sarcoma virus, Muromegalovirus, Murray Valley encephalitis virus, myxoma virus, Myxovirus, Myxovirus multiforme, Myxovirus parotitidis, Nairobi sheep disease virus, Nairovirus, Nanirnavirus, Nariva virus, Ndumo virus, Neethling virus, Nelson Bay virus, neurotropic virus, New World Arenavirus, newborn pneumonitis virus, Newcastle disease virus, Nipah virus, noncytopathogenic virus, Norwalk virus, nuclear polyhedrosis virus (NPV), nipple neck virus, O'nyong'nyong virus, Ockelbo virus, oncogenic virus, oncogenic viruslike particle, oncornavirus, Orbivirus, Orf virus, Oropouche virus, Orthohepadnavirus, Orthomyxovirus, Orthopoxvirus, Orthoreovirus, Orungo, ovine papillomavirus, ovine catarrhal fever virus, owl monkey herpesvirus, Palyam virus, Papillomavirus, Papillomavirus sylvilagi, Papovavirus, parainfluenza virus, parainfluenza virus type 1, parainfluenza virus type 2, parainfluenza virus type 3, parainfluenza virus type 4, Paramyxovirus, Parapoxvirus, paravaccinia virus, Parvovirus, Parvovirus B19, parvovirus group, Pestivirus, Phlebovirus, phocine distemper virus, Picodnavirus, Picornavirus, pig cytomegalovirus—pigeonpox virus, Piry virus, Pixuna virus, pneumonia virus of mice, Pneumovirus, poliomyelitis virus, poliovirus, Polydnavirus, polyhedral virus, polyoma virus, Polyomavirus, Polyomavirus bovis, Polyomavirus cercopitheci, Polyomavirus hominis 2, Polyomavirus maccacae 1, Polyomavirus muris 1, Polyomavirus muris 2, Polyomavirus papionis 1, Polyomavirus papionis 2, Polyomavirus sylvilagi, Pongine herpesvirus 1, porcine epidemic diarrhea virus, porcine hemagglutinating encephalomyelitis virus, porcine parvovirus, porcine transmissible gastroenteritis virus, porcine type C virus, pox virus, poxvirus, poxvirus variolae, Prospect Hill virus, Provirus, pseudocowpox virus, pseudorabies virus, psittacinepox virus, quailpox virus, rabbit fibroma virus, rabbit kidney vaculolating virus, rabbit papillomavirus, rabies virus, raccoon parvovirus, raccoonpox virus, Ranikhet virus, rat cytomegalovirus, rat parvovirus, rat virus, Rauscher's virus, recombinant vaccinia virus, recombinant virus, reovirus, reovirus 1, reovirus 2, reovirus 3, reptilian type C virus, respiratory infection virus, respiratory syncytial virus, respiratory virus, reticuloendotheliosis virus, Rhabdovirus, Rhabdovirus carpia, Rhadinovirus, Rhinovirus, Rhizidiovirus, Rift Valley fever virus, Riley's virus, rinderpest virus, RNA tumor virus, Ross River virus, Rotavirus, rougeole virus, Rous sarcoma virus, rubella virus, rubeola virus, Rubivirus, Russian autumn encephalitis virus, SA 11 simian virus, SA2 virus, Sabia virus, Sagiyama virus, Saimirine herpesvirus 1, salivary gland virus, sandfly fever virus group, Sandjimba virus, SARS virus, SDAV (sialodacryoadenitis virus), sealpox virus, Semliki Forest Virus, Seoul virus, sheeppox virus, Shope fibroma virus, Shope papilloma virus, simian foamy virus, simian hepatitis A virus, simian human immunodeficiency virus, simian immunodeficiency virus, simian parainfluenza virus, simian T cell lymphotrophic virus, simian virus, simian virus 40, Simplexvirus, Sin Nombre virus, Sindbis virus, smallpox virus, South American hemorrhagic fever viruses, sparrowpox virus, Spumavirus, squirrel fibroma virus, squirrel monkey retrovirus, SSV 1 virus group, STLV (simian T lymphotropic virus) type I, STLV (simian T lymphotropic virus) type II, STLV (simian T lymphotropic virus) type III, stomatitis papulosa virus, submaxillary virus, suid alphaherpesvirus 1, suid herpesvirus 2, Suipoxvirus, swamp fever virus, swinepox virus, Swiss mouse leukemia virus, TAC virus, Tacaribe complex virus, Tacaribe virus, Tanapox virus, Taterapox virus, Tench reovirus, Theiler's encephalomyelitis virus, Theiler's virus, Thogoto virus, Thottapalayam virus, Tick borne encephalitis virus, Tioman virus, Togavirus, Torovirus, tumor virus, Tupaia virus, turkey rhinotracheitis virus, turkeypox virus, type C retroviruses, type D oncovirus, type D retrovirus group, ulcerative disease rhabdovirus, Una virus, Uukuniemi virus group, vaccinia virus, vacuolating virus, varicella zoster virus, Varicellovirus, Varicola virus, variola major virus, variola virus, Vasin Gishu disease virus, VEE virus, Venezuelan equine encephalitis virus, Venezuelan equine encephalomyelitis virus, Venezuelan hemorrhagic fever virus, vesicular stomatitis virus, Vesiculovirus, Vilyuisk virus, viper retrovirus, viral haemorrhagic septicemia virus, Visna Maedi virus, Visna virus, volepox virus, VSV (vesicular stomatitis virus), Wallal virus, Warrego virus, wart virus, WEE virus, West Nile virus, western equine encephalitis virus, western equine encephalomyelitis virus, Whataroa virus, Winter Vomiting Virus, woodchuck hepatitis B virus, woolly monkey sarcoma virus, wound tumor virus, WRSV virus, Yaba monkey tumor virus, Yaba virus, Yatapoxvirus, yellow fever virus, and the Yug Bogdanovac virus.

EXAMPLES

Example 1

Amplification of Barley Genomic DNA

Figure 15:
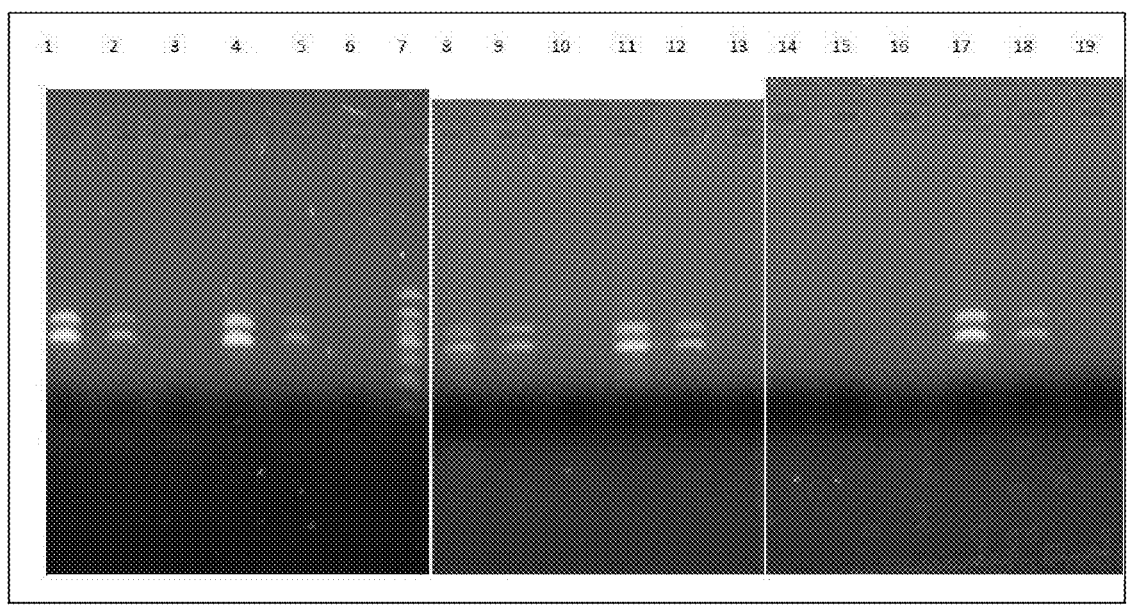
FIG. 15 depicts an electrophoresis gel showing DNA amplification from Barley genomic DNA using a variety of polymerases.

FIG. 15 shows results from amplification of barley genomic DNA using Peptide Tag-Polymerase (an aldehyde-modified form of SEQ ID NO:2) polymerase in comparison with two commercially available polymerases (ABI Gold™ and Roche FastStart™).

Barley genomic DNA was obtained from 5 different genomes. Lane 7 shows a 100 bp ladder.

A description of the lanes is given below:

Lanes 1-3—Peptide Tag-Polymerase at 2.5 U/100 µl PCR reaction Peptide Tag-Polymerase 10× fold dilution starting from 1 ng/µl Lanes 4-6—Peptide Tag-Polymerase at 4 U/100 µl Lanes 8-10 ABI Gold™ at 2.5 U/100 µl PCR reaction ABI Gold™ 10× fold dilution starting from 1 ng/µl;

Lanes 11-13—ABI Gold™ at 4 U/100 µl

Lanes 14-16 Roche FastStart™ at 2.5 U/100 µl PCR reaction ABI Gold™ 10× fold dilution starting from 1 ng/µl Lanes 17-19 Roche FastStart™ at 4 U/100 µl Lane 1-3 (Peptide Tag-Polymerase) 2.5 U only—shows amplification of DNA Lane 8 (ABI) shows small nonspecific product (smear)

Lanes 14-16—(Roche) shows no product at 2.5 U

Example 2

Amplification of Mouse Genomic DNA Using Peptide Tag-Polymerase Mixtures

Figure 26:
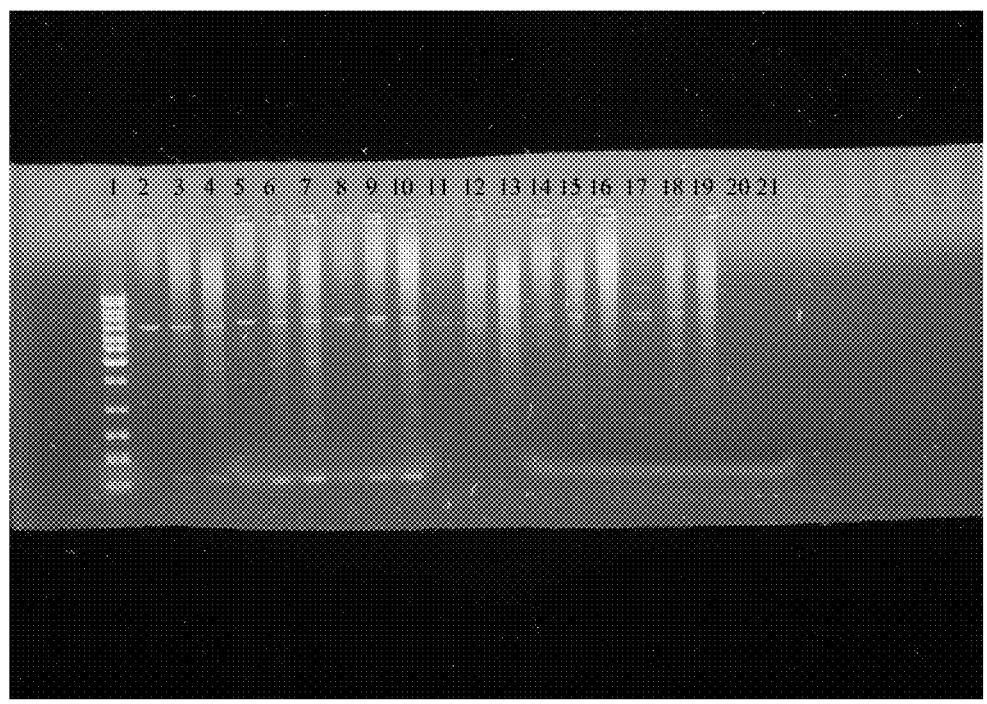
FIG. 26 depicts an electrophoresis gel showing DNA amplification from mouse genomic DNA using Peptide tag-polymerase mixtures.

FIG. 26 shows results from amplification of mouse genomic DNA using a variety of polymerase mixes. Lane 1 shows a 1 kb DNA ladder. Lanes 2-10 show amplification of mouse genomic DNA, 1 ng/µl in 1×PCR. All mixes produced correct PCR product length of 3838 bp. Lanes 11-19 correspond to the same mixes as in Lanes 2-10 but using plasmid template DNA. The expected PCR product was ~8.6 kb and only one Peptide Tag-Polymerase Mixture 1.5 mM $MgCl_2$ (Lane 17) produced the correct product. The Peptide Tag-Polymerase Mixture contains aldehyde-modified forms of SEQ ID NO:2, SEQ ID NO:6 and SEQ ID NO:11. Lanes 20 and 21 show PCR of Peptide Tag-Polymerase only, which produced no product. A description of the lanes is given below:

Lane 1—1 kb DNA ladder.

Lane 2—Peptide Tag-Polymerase Mixture with bovine serum albumin (BSA) Ready to Load (1.5 mM $MgCl_2$)

Lane 3—Peptide Tag-Polymerase Mixture with BSA Ready to Load (2.0 mM $MgCl_2$)

Lane 4—Peptide Tag-Polymerase Mixture with BSA Ready to Load (2.5 mM $MgCl_2$)

Lane 5—Peptide Tag-Polymerase Mixture with BSA (1.5 mM $MgCl_2$)

Lane 6—Peptide Tag-Polymerase Mixture with BSA (2.0 mM $MgCl_2$)

Lane 7—Peptide Tag-Polymerase Mixture with BSA (2.5 mM $MgCl_2$)

Lane 8—Peptide Tag-Polymerase Mixture 1.5 mM $MgCl_2$

Lane 9—Peptide Tag-Polymerase Mixture 2.0 mM $MgCl_2$

Lane 10—Peptide Tag-Polymerase Mixture 2.5 mM $MgCl_2$

Lane 20—Peptide Tag-Polymerase (1.5 mM $MgCl_2$) mouse genomic DNA, 1 ng/μl in 1×PCR.

Lane 21—Peptide Tag-Polymerase (1.5 mM $MgCl_2$) plasmid DNA.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of increasing the thermal stability of a polypeptide comprising covalently linking the polypeptide at the amino-terminus to a peptide tag to form a fusion polypeptide, wherein:
   (a) the peptide tag is at least 95% identical to SEQ ID NO: 1; and
   (b) the fusion polypeptide does not have the amino acid sequence of SEQ ID NO: 2.

2. The method of claim 1, wherein the peptide tag has an amino acid sequence of SEQ ID NO: 1 or SEQ ID NO: 16.

3. The method of claim 1, wherein the peptide tag is encoded by a nucleic acid sequence of SEQ ID NO: 3 or SEQ ID NO: 17.

4. The method of claim 1, wherein the peptide tag comprises at least three histidine residues.

5. The method of claim 1, wherein the polypeptide is erythropoietin, human Leukemia Inhibitory Factor (hLIF), granulocyte macrophage colony-stimulating factor (GM-CSF), insulin, vascular endothelial growth factor (VEGF), leptin, or bevacizumab.

6. The method of claim 1, wherein the fusion polypeptide comprises the amino acid sequence of SEQ ID NO: 20 or SEQ ID NO: 22.

7. The method of claim 1, wherein the polypeptide is a thermostable protein or enzyme.

8. The method of claim 7, wherein the enzyme is a polymerase, reverse transcriptase, nuclease, pyrophosphatase, deaminase, or protease.

9. The method of claim 8, wherein the polymerase is a DNA polymerase I, *Thermus aquaticus* DNA polymerase I (Taq), *Thermococcus gorgonarius* DNA polymerase (Tgo), *Thermus thermophilics* (Tth) DNA polymerase, or ZO5 DNA polymerase.

10. The method of claim 8, wherein the pyrophosphatase is a *Thermoplasma acidophilum* pyrophosphatase (TAPP).

11. The method of claim 8, wherein the deaminase is a *Pyrococcus horikoshii* dCTP deaminase.

12. The method of claim 7, wherein the thermostable protein is a cosmetic peptide or polypeptide.

13. The method of claim 1, wherein the polypeptide comprises at least two polypeptides.

14. The method of claim 13, wherein the polypeptide comprises an enzyme and a double strand binding protein.

15. The method of claim 14, wherein the double strand binding protein comprises an amino acid sequence of SEQ ID NO: 10.

16. The method of claim 1, wherein the peptide tag is at least 98% identical to SEQ ID NO:1.

17. The method of claim 1, wherein covalently linking the polypeptide causes the polypeptide to have thermal stability at 35° C.

18. The method of claim 1, wherein covalently linking the polypeptide causes the polypeptide to have thermal stability at −20° C.

* * * * *

SEQUENCE LISTING

<160> NUMBER OF SEQ ID NOS: 101

<210> SEQ ID NO 1
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Ile Asp Leu Gln Arg Pro Ser Ala Ala Thr Met Val Asp Asp Leu
1               5                   10                  15

Gln Arg Pro His His His His His Pro Trp Asp Tyr Lys Asp Asp
            20                  25                  30

Asp Asp Lys Pro Arg Trp Asn Ser Gly Trp
            35                  40

<210> SEQ ID NO 2
<211> LENGTH: 870
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Ile Asp Leu Gln Arg Pro Ser Ala Ala Thr Met Val Asp Asp Leu
1               5                   10                  15

Gln Arg Pro His His His His His Pro Trp Asp Tyr Lys Asp Asp
            20                  25                  30

Asp Asp Lys Pro Arg Trp Asn Ser Gly Trp Leu Pro Leu Phe Glu Pro
            35                  40                  45

Lys Gly Arg Val Leu Leu Val Asp Gly His His Leu Ala Tyr Arg Thr
50                  55                  60

Phe His Ala Leu Lys Gly Leu Thr Thr Ser Arg Gly Glu Pro Val Gln
65                  70                  75                  80

Ala Val Tyr Gly Phe Ala Lys Ser Leu Leu Lys Ala Leu Lys Glu Asp
                85                  90                  95

Gly Asp Ala Val Ile Val Val Phe Asp Ala Lys Ala Pro Ser Phe Arg
            100                 105                 110

His Glu Ala Tyr Gly Gly Tyr Lys Ala Gly Arg Ala Pro Thr Pro Glu
        115                 120                 125

Asp Phe Pro Arg Gln Leu Ala Leu Ile Lys Glu Leu Val Asp Leu Leu
    130                 135                 140

Gly Leu Ala Arg Leu Glu Val Pro Gly Tyr Glu Ala Asp Asp Val Leu
145                 150                 155                 160

Ala Ser Leu Ala Lys Lys Ala Glu Lys Glu Gly Tyr Glu Val Arg Ile
                165                 170                 175

Leu Thr Ala Asp Lys Asp Leu Tyr Gln Leu Leu Ser Asp Arg Ile His
            180                 185                 190

Val Leu His Pro Glu Gly Tyr Leu Ile Thr Pro Ala Trp Leu Trp Glu
        195                 200                 205

Lys Tyr Gly Leu Arg Pro Asp Gln Trp Ala Asp Tyr Arg Ala Leu Thr
    210                 215                 220

Gly Asp Glu Ser Asp Asn Leu Pro Gly Val Lys Gly Ile Gly Glu Lys
225                 230                 235                 240

Thr Ala Arg Lys Leu Leu Glu Glu Trp Gly Ser Leu Glu Ala Leu Leu

```
                    245                 250                 255
Lys Asn Leu Asp Arg Leu Lys Pro Ala Ile Arg Glu Lys Ile Leu Ala
                260                 265                 270

His Met Asp Asp Leu Lys Leu Ser Trp Asp Leu Ala Lys Val Arg Thr
                275                 280                 285

Asp Leu Pro Leu Glu Val Asp Phe Ala Lys Arg Arg Glu Pro Asp Arg
            290                 295                 300

Glu Arg Leu Arg Ala Phe Leu Glu Arg Leu Glu Phe Gly Ser Leu Leu
305                 310                 315                 320

His Glu Phe Gly Leu Leu Glu Ser Pro Lys Ala Leu Glu Glu Ala Pro
                325                 330                 335

Trp Pro Pro Pro Glu Gly Ala Phe Val Gly Phe Val Leu Ser Arg Lys
                340                 345                 350

Glu Pro Met Trp Ala Asp Leu Leu Ala Leu Ala Ala Ala Arg Gly Gly
                355                 360                 365

Arg Val His Arg Ala Pro Glu Pro Tyr Lys Ala Leu Arg Asp Leu Lys
            370                 375                 380

Glu Ala Arg Gly Leu Leu Ala Lys Asp Leu Ser Val Leu Ala Leu Arg
385                 390                 395                 400

Glu Gly Leu Gly Leu Pro Pro Gly Asp Asp Pro Met Leu Leu Ala Tyr
                405                 410                 415

Leu Leu Asp Pro Ser Asn Thr Thr Pro Glu Gly Val Ala Arg Arg Tyr
                420                 425                 430

Gly Gly Glu Trp Thr Glu Glu Ala Gly Glu Arg Ala Ala Leu Ser Glu
                435                 440                 445

Arg Leu Phe Ala Asn Leu Trp Gly Arg Leu Glu Gly Glu Glu Arg Leu
            450                 455                 460

Leu Trp Leu Tyr Arg Glu Val Glu Arg Pro Leu Ser Ala Val Leu Ala
465                 470                 475                 480

His Met Glu Ala Thr Gly Val Arg Leu Asp Val Ala Tyr Leu Arg Ala
                485                 490                 495

Leu Ser Leu Glu Val Ala Glu Glu Ile Ala Arg Leu Glu Ala Glu Val
                500                 505                 510

Phe Arg Leu Ala Gly His Pro Phe Asn Leu Asn Ser Arg Asp Gln Leu
            515                 520                 525

Glu Arg Val Leu Phe Asp Glu Leu Gly Leu Pro Ala Ile Gly Lys Thr
            530                 535                 540

Glu Lys Thr Gly Lys Arg Ser Thr Ser Ala Ala Val Leu Glu Ala Leu
545                 550                 555                 560

Arg Glu Ala His Pro Ile Val Glu Lys Ile Leu Gln Tyr Arg Glu Leu
                565                 570                 575

Thr Lys Leu Lys Ser Thr Tyr Ile Asp Pro Leu Pro Asp Leu Ile His
                580                 585                 590

Pro Arg Thr Gly Arg Leu His Thr Arg Phe Asn Gln Thr Ala Thr Ala
            595                 600                 605

Thr Gly Arg Leu Ser Ser Ser Asp Pro Asn Leu Gln Asn Ile Pro Val
            610                 615                 620

Arg Thr Pro Leu Gly Gln Arg Ile Arg Arg Ala Phe Ile Ala Glu Glu
625                 630                 635                 640

Gly Trp Leu Leu Val Ala Leu Asp Tyr Ser Gln Ile Glu Leu Arg Val
                645                 650                 655

Leu Ala His Leu Ser Gly Asp Glu Asn Leu Ile Arg Val Phe Gln Glu
                660                 665                 670
```

```
Gly Arg Asp Ile His Thr Glu Thr Ala Ser Trp Met Phe Gly Val Pro
            675                 680                 685

Arg Glu Ala Val Asp Pro Leu Met Arg Arg Ala Ala Lys Thr Ile Asn
        690                 695                 700

Phe Gly Val Leu Tyr Gly Met Ser Ala His Arg Leu Ser Gln Glu Leu
705                 710                 715                 720

Ala Ile Pro Tyr Glu Glu Ala Gln Ala Phe Ile Glu Arg Tyr Phe Gln
                725                 730                 735

Ser Phe Pro Lys Val Arg Ala Trp Ile Glu Lys Thr Leu Glu Glu Gly
            740                 745                 750

Arg Arg Arg Gly Tyr Val Glu Thr Leu Phe Gly Arg Arg Arg Tyr Val
        755                 760                 765

Pro Asp Leu Glu Ala Arg Val Lys Ser Val Arg Glu Ala Ala Glu Arg
770                 775                 780

Met Ala Phe Asn Met Pro Val Gln Gly Thr Ala Ala Asp Leu Met Lys
785                 790                 795                 800

Leu Ala Met Val Lys Leu Phe Pro Arg Leu Glu Met Gly Ala Arg
                805                 810                 815

Met Leu Leu Gln Val His Asp Glu Leu Val Leu Glu Ala Pro Lys Glu
            820                 825                 830

Arg Ala Glu Ala Val Ala Arg Leu Ala Lys Glu Val Met Glu Gly Val
        835                 840                 845

Tyr Pro Leu Ala Val Pro Leu Glu Val Glu Val Gly Ile Gly Glu Asp
    850                 855                 860

Trp Leu Ser Ala Lys Glu
865                 870

<210> SEQ ID NO 3
<211> LENGTH: 141
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
acacaggaaa cagcgatgat cgacctgcag cggccatccg ccgccaccat ggtcgacgac     60
ctgcagcggc cgcaccatca ccatcaccat ccatgggatt acaaggacga cgatgacaag    120
ccgcggtgga attcggggtg g                                              141

<210> SEQ ID NO 4
<211> LENGTH: 2637
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
acacaggaaa cagcgatgat cgacctgcag cggccatccg ccgccaccat ggtcgacgac     60
ctgcagcggc cgcaccatca ccatcaccat ccatgggatt acaaggacga cgatgacaag    120
ccgcggtgga attcggggtg gctgcccctc tttgagccca agggccgggt cctcctggtg    180
gacggccacc acctggccta ccgcaccttc cacgccctga gggcctcac caccagccgg    240 ggggagccgt gcaggcggt ctacggcttc gccaagagcc tcctcaaggc cctcaaggag    300
gacggggacg cggtgatcgt ggtctttgac gccaaggccc cctccttccg ccacgaggcc    360
```

```
tacgggggt  acaaggcggg  ccgggccccc  acgccggagg  actttcccccg  gcaactcgcc      420 ctcatcaagg  agctggtgga  cctcctgggg  ctggcgcgcc  tcgaggtccc  gggctacgag      480
gcggacgacg  tcctggccag  cctggccaag  aaggcgaaa   aggagggcta  cgaggtccgc      540
atcctcaccg  ccgacaaaga  cctttaccag  ctccttccg   accgcatcca  cgtcctccac      600 cccgagggggt  acctcatcac  cccggcctgg  ctttgggaaa  agtacggcct  gaggcccgac    660
cagtgggcca  actaccgggc  cctgaccggg  gacgagtccg  acaaccttcc  cggggtcaag      720
ggcatcgggg  agaagacggc  gaggaagctt  ctggaggagt  gggggagcct  ggaagccctc      780
ctcaagaacc  tggaccggct  gaagcccgcc  atccgggaga  gatcctggcc  cacatggac       840 gatctgaagc  tctcctggga  cctggccaag  gtgcgcaccg  acctgcccct  ggaggtggac      900
ttcgccaaaa  ggcgggagcc  cgaccgggag  aggcttaggg  cctttctgga  gaggcttgag      960
tttggcagcc  tcctccacga  gttcggcctt  ctggaaagcc  caaggccct   ggaggaggcc     1020 ccctggcccc  cgccggaagg  ggccttcgtg  ggctttgtgc  tttcccgcaa  ggagcccatg     1080
tgggccgatc  ttctggcct   ggccgccgcc  aggggggccc  gggtccaccg  gccccccgag     1140
ccttataaag  ccctcaggga  cctgaaggag  gcgcgggggc  ttctcgccaa  agacctgagc     1200
gttctggccc  tgagggaagg  ccttggcctc  ccgcccggcg  acgacccat   gctcctcgcc     1260 tacctcctgg  acccttccaa  caccacccccc  gaggggggtgg  cccggcgcta  cggcggggag   1320
tggacggagg  aggcggggga  gcgggccgcc  cttttccgaga  ggctcttcgc  caacctgtgg    1380
gggaggcttg  aggggggagga  gaggctcctt  tggctttacc  gggaggtgga  gaggcccctt    1440
tccgctgtcc  tggcccacat  ggaggccacg  ggggtgcgcc  tggacgtggc  ctatctcagg    1500
gccttgtccc  tggaggtggc  cgaggagatc  gcccgcctcg  aggccgaggt  cttccgcctg    1560
gccggccacc  ccttcaacct  caactcccgg  gaccagctgg  aaagggtcct  ctttgacgag    1620
ctagggcttc  ccgccatcgg  caagacggag  aagaccggca  agcgctccac  cagcgccgcc   1680
gtcctggagg  ccctccgcga  ggcccacccc  atcgtggaga  gatcctgca   gtaccgggag    1740 ctcaccaagc  tgaagagcac  ctacattgac  cccttgccgg  acctcatcca  ccccaggacg    1800
ggccgcctcc  acacccgctt  caaccagacg  gccacggcca  cgggcaggct  aagtagctcc    1860
gatcccaacc  tccagaacat  cccccgtccgc  acccccgcttg  ggcagaggat  ccgccgggcc   1920
ttcatcgccg  aggaggggtg  gctattggtg  gccctggact  atagccagat  agagctcagg    1980
gtgctggccc  acctctccgg  cgacgagaac  ctgatccggg  tcttccagga  ggggcgggac   2040
atccacacgg  agaccgccag  ctggatgttc  ggcgtccccc  gggaggccgt  ggacccctg    2100 atgcgccggg  cggccaagac  catcaacttc  ggggtcctct  acggcatgtc  ggcccaccgc   2160
ctctcccagg  agctagccat  cccttacgag  gaggcccagg  ccttcattga  gcgctacttt   2220
cagagcttcc  ccaaggtgcg  ggcctggatt  gagaagaccc  tggaggaggg  caggaggcgg    2280
gggtacgtgg  agaccctctt  cggccgccgc  cgctacgtgc  cagacctaga  ggcccgggtg    2340
aagagcgtgc  gggaggcggc  cgagcgcatg  gccttcaaca  tgcccgtcca  gggcaccgcc    2400
gccgacctca  tgaagctggc  tatggtgaag  ctcttcccca  ggctggagga  aatgggggcc    2460
aggatgctcc  ttcaggtcca  cgacgagctg  gtcctcgagg  ccccaaaaga  gagggcggag    2520
gccgtggccc  ggctggccaa  ggaggtcatg  gagggggtgt  atccctggc   cgtgccctg     2580 gaggtggagg  tggggatagg  ggaggactgg  ctctccgcca  aggagtgata  gatctga       2637
```

<210> SEQ ID NO 5

<211> LENGTH: 2829
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 5

| | | | | | |
|---|---|---|---|---|---|
| acacaggaaa | cagcgatgat | cgacctgcag | cggccgcagg | ccgccaccat | ggactctaga | 60 |
| caccatcacc | atcaccaccc | atggattac | aaggacgacg | atgacaagcc | gcggtggaat | 120 |
| tcgagcgcaa | ccgtaaagtt | caagtacaaa | ggcgaagaaa | agaggtaga | catctccaag | 180 |
| atcaagaaag | tatggcgtgt | gggcaagatg | atctccttca | cctacgacga | gggcggtggc | 240 |
| aagaccggcc | gcggtgcggt | aagcgaaaag | gacgcgccga | aggagctgct | gcagatgctg | 300 |
| gagaagcaga | aaaagattaa | gaattcgggt | aacctgcccc | tctttgagcc | caagggccgg | 360 |
| gtcctcctgg | tggacggcca | ccacctggcc | taccgcacct | tccacgccct | gaagggcctc | 420 |
| accaccagcc | ggggggagcc | ggtgcaggcg | gtctacggct | cgccaagag | cctcctcaag | 480 |
| gccctcaagg | aggacgggga | cgcggtgatc | gtggtctttg | acgccaaggc | cccctccttc | 540 |
| cgccacgagg | cctacggggg | gtacaaggcg | ggccgggccc | ccacaccgga | ggactttccc | 600 |
| cggcaactcg | ccctcatcaa | ggagctggtg | gacctcctgg | ggctggcgcg | cctcgaggtc | 660 |
| ccgggctacg | aggcggacga | cgtcctggcc | agcctggcca | agaaggcgga | aaaggagggc | 720 |
| tacgaggtcc | gcatcctcac | cgccgacaaa | gacctttacc | agctcctttc | cgaccgcatc | 780 |
| cacgtcctcc | accccgaggg | gtacctcatc | accccggcct | ggctttggga | aaagtacggc | 840 |
| ctgaggcccg | accagtgggc | cgactaccgg | gccctgaccg | gggacgagtc | cgacaacctt | 900 |
| cccgggtca | agggcatcgg | ggagaagacg | gcgaggaagc | ttctggagga | gtgggggagc | 960 |
| ctggaagccc | tcctcaagaa | cctggaccgg | ctgaagcccg | ccatcgggga | aagatcctg | 1020 |
| gcccacatgg | acgatctgaa | gctctcctgg | gacctggcca | aggtgcgcac | cgacctgccc | 1080 |
| ctggaggtgg | acttcgccaa | aaggcgggag | cccgaccggg | agaggcttag | ggccttttctg | 1140 |
| gagaggcttg | agtttggcag | cctcctccac | gagttcggcc | ttctggaaag | ccccaaggcc | 1200 |
| ctggaggagg | ccccctggcc | cccgccgaaa | ggggccttcg | tgggctttgt | gctttcccgc | 1260 |
| aaggagccca | tgtgggccga | tcttctggcc | ctggccgccg | cagggggg | ccgggtccac | 1320 |
| cgggcccccg | agcctattaaa | agccctcagg | gacctgaagg | aggcgcgggg | gcttctcgcc | 1380 |
| aaagacctga | gcgttctggc | cctgagggaa | ggccttggcc | tcccgcccgg | cgacgacccc | 1440 |
| atgctcctcg | cctacctcct | ggaccctcc | aacaccaccc | ccgaggggt | ggcccggcgc | 1500 |
| tacggcgggg | agtggacgga | ggaggcgggg | gagcgggccg | ccctttccga | gaggctcttc | 1560 |
| gccaacctgt | gggggaggct | tgaggggag | gagaggctcc | tttggcttta | ccgggaggtg | 1620 |
| gagaggcccc | tttccgctgt | cctggcccac | atggaggcca | cgggggtgcg | cctggacgtg | 1680 |
| gcctatctca | gggccttgtc | cctggaggtg | gccgaggaga | tcgcccgcct | cgaggccgag | 1740 |
| gtcttccgcc | tggccggcca | ccccttcaac | ctcaactccc | gggaccagct | ggaaagggtc | 1800 |
| ctctttgacg | agctagggct | tcccgccatc | ggcaagacgg | agaagaccgg | caagcgctcc | 1860 |
| accagcgccg | ccgtcctgga | ggccctccgc | gaggcccacc | ccatcgtgga | agatcctg | 1920 |
| cagtaccggg | agctcaccaa | gctgaagagc | acctacattg | accccttgcc | ggacctcatc | 1980 |
| caccccagga | cgggccgcct | ccacacccgc | ttcaaccaga | cggccacggc | cacgggcagg | 2040 |
| ctaagtagct | ccgatcccaa | cctccagaac | atccccgtcc | gcaccccgct | tgggcagagg | 2100 |

```
atccgccggg ccttcatcgc cgaggagggg tggctattgg tggccctgga ctatagccag    2160
atagagctca gggtgctggc ccacctctcc ggcgacgaga acctgatccg ggtcttccag    2220
gaggggcggg acatccacac ggagaccgcc agctggatgt tcggcgtccc ccgggaggcc    2280
gtggaccccc tgatgcgccg ggcggccaag accatcaact tcggggtcct ctacggcatg    2340
tcggcccacc gcctctccca ggagctagcc atcccttacg aggaggccca ggccttcatt    2400
gagcgctact ttcagagctt ccccaaggtg cgggcctgga ttgagaagac cctggaggag    2460
ggcaggaggc gggggtacgt ggagaccctc ttcggccgcc gccgctacgt gccagaccta    2520
gaggcccggg tgaagagcgt gcgggaggcg gccgagcgca tggccttcaa catgcccgtc    2580
cagggcaccg ccgccgacct catgaagctg gctatggtga agctcttccc caggctggag    2640
gaaatggggg ccaggatgct ccttcaggtc cacgacgagc tggtcctcga ggccccaaaa    2700
gagagggcgg aggccgtggc ccggctggcc aaggaggtca tggaggggt gtatcccctg     2760 gccgtgcccc tggaggtgga ggtggggata ggggaggact ggctctccgc caaggagtga    2820
tagatctga                                                            2829
```

<210> SEQ ID NO 6
<211> LENGTH: 934
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 6

```
Met Ile Asp Leu Gln Arg Pro Gln Ala Ala Thr Met Asp Ser Arg His
1               5                   10                  15

His His His His His Pro Trp Asp Tyr Lys Asp Asp Asp Lys Pro
            20                  25                  30

Arg Trp Asn Ser Ser Ala Thr Val Lys Phe Lys Tyr Lys Gly Glu Glu
        35                  40                  45

Lys Glu Val Asp Ile Ser Lys Ile Lys Lys Val Trp Arg Val Gly Lys
    50                  55                  60

Met Ile Ser Phe Thr Tyr Asp Glu Gly Gly Lys Thr Gly Arg Gly
65                  70                  75                  80

Ala Val Ser Glu Lys Asp Ala Pro Lys Glu Leu Leu Gln Met Leu Glu
                85                  90                  95

Lys Gln Lys Lys Ile Lys Asn Ser Gly Asn Leu Pro Leu Phe Glu Pro
            100                 105                 110

Lys Gly Arg Val Leu Leu Val Asp Gly His His Leu Ala Tyr Arg Thr
        115                 120                 125

Phe His Ala Leu Lys Gly Leu Thr Thr Ser Arg Gly Glu Pro Val Gln
    130                 135                 140

Ala Val Tyr Gly Phe Ala Lys Ser Leu Leu Lys Ala Leu Lys Glu Asp
145                 150                 155                 160

Gly Asp Ala Val Ile Val Val Phe Asp Ala Lys Ala Pro Ser Phe Arg
                165                 170                 175

His Glu Ala Tyr Gly Gly Tyr Lys Ala Gly Arg Ala Pro Thr Pro Glu
            180                 185                 190

Asp Phe Pro Arg Gln Leu Ala Leu Ile Lys Glu Leu Val Asp Leu Leu
        195                 200                 205

Gly Leu Ala Arg Leu Glu Val Pro Gly Tyr Glu Ala Asp Asp Val Leu
    210                 215                 220
```

```
Ala Ser Leu Ala Lys Lys Ala Glu Lys Glu Gly Tyr Glu Val Arg Ile
225                 230                 235                 240

Leu Thr Ala Asp Lys Asp Leu Tyr Gln Leu Leu Ser Asp Arg Ile His
            245                 250                 255

Val Leu His Pro Glu Gly Tyr Leu Ile Thr Pro Ala Trp Leu Trp Glu
        260                 265                 270

Lys Tyr Gly Leu Arg Pro Asp Gln Trp Ala Asp Tyr Arg Ala Leu Thr
    275                 280                 285

Gly Asp Glu Ser Asp Asn Leu Pro Gly Val Lys Gly Ile Gly Glu Lys
290                 295                 300

Thr Ala Arg Lys Leu Leu Glu Glu Trp Gly Ser Leu Glu Ala Leu Leu
305                 310                 315                 320

Lys Asn Leu Asp Arg Leu Lys Pro Ala Ile Arg Glu Lys Ile Leu Ala
                325                 330                 335

His Met Asp Asp Leu Lys Leu Ser Trp Asp Leu Ala Lys Val Arg Thr
            340                 345                 350

Asp Leu Pro Leu Glu Val Asp Phe Ala Lys Arg Arg Glu Pro Asp Arg
        355                 360                 365

Glu Arg Leu Arg Ala Phe Leu Glu Arg Leu Glu Phe Gly Ser Leu Leu
    370                 375                 380

His Glu Phe Gly Leu Leu Glu Ser Pro Lys Ala Leu Glu Glu Ala Pro
385                 390                 395                 400

Trp Pro Pro Pro Glu Gly Ala Phe Val Gly Phe Val Leu Ser Arg Lys
                405                 410                 415

Glu Pro Met Trp Ala Asp Leu Leu Ala Leu Ala Ala Ala Arg Gly Gly
            420                 425                 430

Arg Val His Arg Ala Pro Glu Pro Tyr Lys Ala Leu Arg Asp Leu Lys
        435                 440                 445

Glu Ala Arg Gly Leu Leu Ala Lys Asp Leu Ser Val Leu Ala Leu Arg
    450                 455                 460

Glu Gly Leu Gly Leu Pro Pro Gly Asp Asp Pro Met Leu Leu Ala Tyr
465                 470                 475                 480

Leu Leu Asp Pro Ser Asn Thr Thr Pro Glu Gly Val Ala Arg Arg Tyr
                485                 490                 495

Gly Gly Glu Trp Thr Glu Glu Ala Gly Glu Arg Ala Ala Leu Ser Glu
            500                 505                 510

Arg Leu Phe Ala Asn Leu Trp Gly Arg Leu Glu Gly Glu Glu Arg Leu
        515                 520                 525

Leu Trp Leu Tyr Arg Glu Val Glu Arg Pro Leu Ser Ala Val Leu Ala
    530                 535                 540

His Met Glu Ala Thr Gly Val Arg Leu Asp Val Ala Tyr Leu Arg Ala
545                 550                 555                 560

Leu Ser Leu Glu Val Ala Glu Glu Ile Ala Arg Leu Glu Ala Glu Val
                565                 570                 575

Phe Arg Leu Ala Gly His Pro Phe Asn Leu Asn Ser Arg Asp Gln Leu
            580                 585                 590

Glu Arg Val Leu Phe Asp Glu Leu Gly Leu Pro Ala Ile Gly Lys Thr
        595                 600                 605

Glu Lys Thr Gly Lys Arg Ser Thr Ser Ala Ala Val Leu Glu Ala Leu
    610                 615                 620

Arg Glu Ala His Pro Ile Val Glu Lys Ile Leu Gln Tyr Arg Glu Leu
625                 630                 635                 640

Thr Lys Leu Lys Ser Thr Tyr Ile Asp Pro Leu Pro Asp Leu Ile His
```

Pro Arg Thr Gly Arg Leu His Thr Arg Phe Asn Gln Thr Ala Thr Ala
    645                 650                 655

Thr Gly Arg Leu Ser Ser Asp Pro Asn Leu Gln Asn Ile Pro Val
660                 665                 670

Arg Thr Pro Leu Gly Gln Arg Ile Arg Arg Ala Phe Ile Ala Glu Glu
    675                 680                 685

Gly Trp Leu Leu Val Ala Leu Asp Tyr Ser Gln Ile Glu Leu Arg Val
690                 695                 700

Leu Ala His Leu Ser Gly Asp Glu Asn Leu Ile Arg Val Phe Gln Glu
705                 710                 715                 720

Gly Arg Asp Ile His Thr Glu Thr Ala Ser Trp Met Phe Gly Val Pro
            725                 730                 735

Arg Glu Ala Val Asp Pro Leu Met Arg Ala Ala Lys Thr Ile Asn
        740                 745                 750

Phe Gly Val Leu Tyr Gly Met Ser Ala His Arg Leu Ser Gln Glu Leu
    755                 760                 765

Ala Ile Pro Tyr Glu Glu Ala Gln Ala Phe Ile Glu Arg Tyr Phe Gln
770                 775                 780

Ser Phe Pro Lys Val Arg Ala Trp Ile Glu Lys Thr Leu Glu Glu Gly
785                 790                 795                 800

Arg Arg Arg Gly Tyr Val Glu Thr Leu Phe Gly Arg Arg Arg Tyr Val
            805                 810                 815

Pro Asp Leu Glu Ala Arg Val Lys Ser Val Arg Glu Ala Ala Glu Arg
        820                 825                 830

Met Ala Phe Asn Met Pro Val Gln Gly Thr Ala Ala Asp Leu Met Lys
    835                 840                 845

Leu Ala Met Val Lys Leu Phe Pro Arg Leu Glu Glu Met Gly Ala Arg
850                 855                 860

Met Leu Leu Gln Val His Asp Glu Leu Val Leu Glu Ala Pro Lys Glu
865                 870                 875                 880

Arg Ala Glu Ala Val Ala Arg Leu Ala Lys Glu Val Met Glu Gly Val
            885                 890                 895

Tyr Pro Leu Ala Val Pro Leu Glu Val Glu Val Gly Ile Gly Glu Asp
        900                 905                 910

Trp Leu Ser Ala Lys Glu
    915                 920                 925

<210> SEQ ID NO 7
<211> LENGTH: 325
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
atgatcgacc tgcagcggcc gcaggccgcc accatggact ctagacacca tcaccatcac        60
cacccatggg attacaagga cgacgatgac aagccgcggt ggaattcgag cgcaaccgta       120
aagttcaagt acaaaggcga agaaaaagag gtagacatct ccaagatcaa gaaagtatgg       180
cgtgtgggca agatgatctc cttcacctac gacgagggcg gtggcaagac cggccgcggt       240
gcggtaagcg aaaaggacgc gccgaaggag ctgctgcaga tgctggagaa gcagaaaaag       300
attaagaatt cgggtaacct gcccc                                             325

<210> SEQ ID NO 8
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

```
Met Ile Asp Leu Gln Arg Pro Gln Ala Ala Thr Met Asp Ser Arg His
1               5                   10                  15

His His His His His Pro Trp Asp Tyr Lys Asp Asp Asp Lys Pro
            20                  25                  30

Arg Trp Asn Ser Ser Ala Thr Val Lys Phe Lys Tyr Lys Gly Glu Glu
        35                  40                  45

Lys Glu Val Asp Ile Ser Lys Ile Lys Lys Val Trp Arg Val Gly Lys
    50                  55                  60

Met Ile Ser Phe Thr Tyr Asp Glu Gly Gly Gly Lys Thr Gly Arg Gly
65                  70                  75                  80

Ala Val Ser Glu Lys Asp Ala Pro Lys Glu Leu Leu Gln Met Leu Glu
                85                  90                  95

Lys Gln Lys Lys Ile Lys Asn Ser Gly Asn
            100                 105
```

<210> SEQ ID NO 9
<211> LENGTH: 204
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9

```
agcgcaaccg taaagttcaa gtacaaaggc gaagaaaaag aggtagacat ctccaagatc    60
aagaaagtat ggcgtgtggg caagatgatc tccttcacct acgacgaggg cggtggcaag   120
accggccgcg gtgcggtaag cgaaaaggac gcgccgaagg agctgctgca gatgctggag   180
aagcagaaaa agattaagaa ttcg                                          204
```

<210> SEQ ID NO 10
<211> LENGTH: 68
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

```
Ser Ala Thr Val Lys Phe Lys Tyr Lys Gly Glu Glu Lys Glu Val Asp
1               5                   10                  15

Ile Ser Lys Ile Lys Lys Val Trp Arg Val Gly Lys Met Ile Ser Phe
            20                  25                  30

Thr Tyr Asp Glu Gly Gly Gly Lys Thr Gly Arg Gly Ala Val Ser Glu
        35                  40                  45

Lys Asp Ala Pro Lys Glu Leu Leu Gln Met Leu Glu Lys Gln Lys Lys
    50                  55                  60

Ile Lys Asn Ser
65
```

<210> SEQ ID NO 11

<211> LENGTH: 876
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 11

```
Met Ile Asp Leu Gln Arg Pro Gln Ala Ala Thr Met Asp Ser Arg His
1               5                   10                  15

His His His His His Pro Trp Asp Tyr Lys Asp Asp Asp Lys Pro
            20                  25                  30

Arg Trp Asn Ser Ile Leu Asp Thr Asp Tyr Ile Thr Glu Asp Gly Lys
        35                  40                  45

Pro Val Ile Arg Ile Phe Lys Lys Glu Asn Gly Glu Phe Lys Ile Asp
    50                  55                  60

Tyr Asp Arg Asn Phe Glu Pro Tyr Ile Tyr Ala Leu Leu Lys Asp Asp
65                  70                  75                  80

Ser Ala Ile Glu Asp Val Lys Lys Ile Thr Ala Glu Arg His Gly Thr
                85                  90                  95

Thr Val Arg Val Val Arg Ala Glu Lys Val Lys Lys Lys Phe Leu Gly
            100                 105                 110

Arg Pro Ile Glu Val Trp Lys Leu Tyr Phe Thr His Pro Gln Asp Val
        115                 120                 125

Pro Ala Ile Arg Asp Lys Ile Lys Glu His Pro Ala Val Val Asp Ile
    130                 135                 140

Tyr Glu Tyr Asp Ile Pro Phe Ala Lys Arg Tyr Leu Ile Asp Lys Gly
145                 150                 155                 160

Leu Ile Pro Met Glu Gly Asp Glu Glu Leu Lys Met Leu Ala Phe Asp
                165                 170                 175

Ile Glu Thr Leu Tyr His Glu Gly Glu Glu Phe Ala Glu Gly Pro Ile
            180                 185                 190

Leu Met Ile Ser Tyr Ala Asp Glu Glu Gly Ala Arg Val Ile Thr Trp
        195                 200                 205

Lys Asn Ile Asp Leu Pro Tyr Val Asp Val Val Ser Thr Glu Lys Glu
    210                 215                 220

Met Ile Lys Arg Phe Leu Lys Val Val Lys Glu Lys Asp Pro Asp Val
225                 230                 235                 240

Leu Ile Thr Tyr Asn Gly Asp Asn Phe Asp Phe Ala Tyr Leu Lys Lys
                245                 250                 255

Arg Ser Glu Lys Leu Gly Val Lys Phe Ile Leu Gly Arg Glu Gly Ser
            260                 265                 270

Glu Pro Lys Ile Gln Arg Met Gly Asp Arg Phe Ala Val Glu Val Lys
        275                 280                 285

Gly Arg Ile His Phe Asp Leu Tyr Pro Val Ile Arg Arg Thr Ile Asn
    290                 295                 300

Leu Pro Thr Tyr Thr Leu Glu Ala Val Tyr Glu Ala Ile Phe Gly Gln
305                 310                 315                 320

Pro Lys Glu Lys Val Tyr Ala Glu Glu Ile Ala Gln Ala Trp Glu Thr
                325                 330                 335

Gly Glu Gly Leu Glu Arg Val Ala Arg Tyr Ser Met Glu Asp Ala Lys
            340                 345                 350

Val Thr Tyr Glu Leu Gly Lys Glu Phe Phe Pro Met Glu Ala Gln Leu
        355                 360                 365

Ser Arg Leu Val Gly Gln Ser Leu Trp Asp Val Ser Arg Ser Ser Thr
```

-continued

```
            370                 375                 380
Gly Asn Leu Val Glu Trp Phe Leu Leu Arg Lys Ala Tyr Glu Arg Asn
385                 390                 395                 400

Glu Leu Ala Pro Asn Lys Pro Asp Glu Arg Glu Leu Ala Arg Arg Arg
                405                 410                 415

Glu Ser Tyr Ala Gly Gly Tyr Val Glu Pro Glu Arg Gly Leu Trp
                420                 425                 430

Glu Asn Ile Val Tyr Leu Asp Phe Arg Ser Leu Tyr Pro Ser Ile Ile
                435                 440                 445

Ile Thr His Asn Val Ser Pro Asp Thr Leu Asn Arg Glu Gly Cys Glu
            450                 455                 460

Glu Tyr Asp Val Ala Pro Gln Val Gly His Lys Phe Cys Lys Asp Phe
465                 470                 475                 480

Pro Gly Phe Ile Pro Ser Leu Leu Gly Asp Leu Leu Glu Glu Arg Gln
                485                 490                 495

Lys Val Lys Lys Lys Met Lys Ala Thr Ile Asp Pro Ile Glu Lys Lys
                500                 505                 510

Leu Leu Asp Tyr Arg Gln Arg Ala Ile Lys Ile Leu Ala Asn Ser Phe
            515                 520                 525

Tyr Gly Tyr Tyr Gly Tyr Ala Lys Ala Arg Trp Tyr Cys Lys Glu Cys
530                 535                 540

Ala Glu Ser Val Thr Ala Trp Gly Arg Gln Tyr Ile Glu Thr Thr Ile
545                 550                 555                 560

Arg Glu Ile Glu Glu Lys Phe Gly Phe Lys Val Leu Tyr Ala Asp Thr
                565                 570                 575

Asp Gly Phe Phe Ala Thr Ile Pro Gly Ala Asp Ala Glu Thr Val Lys
                580                 585                 590

Lys Lys Ala Lys Glu Phe Leu Asp Tyr Ile Asn Ala Lys Leu Pro Gly
            595                 600                 605

Leu Leu Glu Leu Glu Tyr Glu Gly Phe Tyr Lys Arg Gly Phe Phe Val
610                 615                 620

Thr Lys Lys Lys Tyr Ala Val Ile Asp Glu Glu Asp Lys Ile Thr Thr
625                 630                 635                 640

Arg Gly Leu Glu Ile Val Arg Arg Asp Trp Ser Glu Ile Ala Lys Glu
                645                 650                 655

Thr Gln Ala Arg Val Leu Glu Ala Ile Leu Lys His Gly Asp Val Glu
                660                 665                 670

Glu Ala Val Arg Ile Val Lys Glu Val Thr Glu Lys Leu Ser Lys Tyr
            675                 680                 685

Glu Val Pro Pro Glu Lys Leu Val Ile Tyr Glu Gln Ile Thr Arg Asp
690                 695                 700

Leu Lys Asp Tyr Lys Ala Thr Gly Pro His Val Ala Val Ala Lys Arg
705                 710                 715                 720

Leu Ala Ala Arg Gly Ile Lys Ile Arg Pro Gly Thr Val Ile Ser Tyr
                725                 730                 735

Ile Val Leu Lys Gly Ser Gly Arg Ile Gly Asp Arg Ala Ile Pro Phe
                740                 745                 750

Asp Glu Phe Asp Pro Ala Lys His Lys Tyr Asn Ala Glu Tyr Tyr Ile
            755                 760                 765

Glu Asn Gln Val Leu Pro Ala Val Glu Arg Ile Leu Arg Ala Phe Gly
            770                 775                 780

Tyr Arg Lys Glu Asp Leu Arg Tyr Gln Lys Thr Arg Gln Val Gly Leu
785                 790                 795                 800
```

Gly Ala Trp Leu Lys Pro Lys Thr Ser Trp Ile Cys Ala Thr Val Lys
                805                 810                 815

Phe Lys Tyr Lys Gly Glu Glu Lys Glu Val Asp Ile Ser Lys Ile Lys
            820                 825                 830

Lys Val Trp Arg Val Gly Lys Met Ile Ser Phe Thr Tyr Asp Glu Gly
        835                 840                 845

Gly Gly Lys Thr Gly Arg Gly Ala Val Ser Glu Lys Asp Ala Pro Lys
    850                 855                 860

Glu Leu Leu Gln Met Leu Glu Lys Gln Lys Lys Ile
865                 870                 875

<210> SEQ ID NO 12
<211> LENGTH: 2634
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12

```
atgatcgacc tgcagcggcc gcaggccgcc accatggact ctagacacca tcaccatcac    60
cacccatggg attacaagga cgacgatgac aagccgcggt ggaattccat cctcgataca   120
gactacataa ctgaggatgg aaagcccgtc atcaggatct tcaagaagga aacggcgag    180
ttcaaaatag actacgacag aaactttgag ccatacatct acgcgctctt gaaggacgac   240
tctgcgattg aggacgtcaa gaagataact gccgagaggc acggcactac cgttagggtt   300
gtcagggccg agaaagtgaa gaagaagttc ctaggcaggc cgatagaggt ctggaagctc   360
tacttcactc accccagga cgttcccgca atcaggaca agataaagga gcatcctgcc    420
gttgtggaca tctacgagta cgacatcccc ttcgcgaagc gctacctcat agacaaaggc   480
ttaatcccga tggagggcga cgaggaactt aagatgctcg ccttcgacat cgagacgctc   540
tatcacgagg gcgaggagtt cgccgaaggg cctatcctga tgataagcta cgccgacgag   600
gaaggggcgc gcgttattac ctggaagaat atcgacttc cctatgtcga cgtcgtttcc    660
accgagaagg agatgataaa gcgcttcctc aaggtcgtca aggaaaagga tcccgacgtc   720
ctcataacct acaacggcga caacttcgac ttcgcctacc tcaagaagcg ctccgagaag   780
ctcggagtca agttcatcct cggaagggaa gggagcgagc gaaaatcca gcgcatgggc    840
gatcgctttg cggtggaggt caagggaagg attcacttcg acctctaccc cgtcattagg   900
agaacgatta acctccccac ttacacccctt gaggcagtat atgaagccat ctttggacag   960
ccgaaggaga aggtctacgc tgaggagata gcgcaggcct gggaaacggg cgagggatta  1020
gaaagggtgg cccgctactc gatggaggac gcaaaggtaa cctatgaact cggaaaagag  1080
ttcttcccta tggaagccca gctctcgcgc ctcgtaggcc agagcctctg ggatgtatct  1140
cgctcgagta ccggaaacct cgtcgagtgg ttttttgctga ggaaggccta cgagaggaat  1200
gaacttgcac aaacaagcc ggacgagagg gagctggcaa agaagggga gagctacgcg   1260
ggtggatacg tcaaggagcc gaaaggggga ctgtgggaga acatcgtgta tctggacttc  1320
cgctcccctgt atccttcgat aataatcacc ataacgtct cccctgatac actcaacagg   1380
gagggttgtg aggagtacga cgtggctcct caggtaggcc ataagttctg caaggacttc  1440
cccggcttca tcccaagcct cctcgggac tccttggagg agacagaa ggtaaagaag    1500
aagatgaagg ccactataga cccaatcgag aagaaactcc tcgattacag gcagcgagca  1560
```

-continued

```
atcaaaatcc ttgctaatag cttctacggt tactacggct atgcaaaggc ccgctggtac    1620
tgcaaggagt gcgccgagag cgttaccgct tggggcaggc agtacatcga gaccacgata    1680
agggaaatag aggagaaatt tggctttaaa gtcctctacg cggacacaga tggattttc     1740 gcaacaatac ctggagcgga cgccgaaacc gtcaaaaaga aggcaaagga gttcctggac    1800
tacatcaacg ccaaactgcc cggcctgctc gaactcgaat acgagggctt ctacaagcgc    1860
ggcttcttcg tgacgaagaa gaagtacgcg gttatagacg aggaggacaa gataacgacg    1920
cgcgggcttg aaatagttag gcgtgactgg agcgagatag cgaaggagac gcaggcgagg    1980
gttcttgagg cgatactaaa gcacggtgac gttgaagaag cggtaaggat tgtcaaagag    2040
gttacggaga agctgagcaa gtacgaggtt ccaccggaga agctggtcat ctacgagcag    2100 ataaccccgcg acctgaagga ctacaaggcc accgggccgc atgtggctgt tgcaaaacgc    2160
ctcgccgcaa gggggataaa aatccggccc ggaacggtca taagctacat cgtgctcaaa    2220
ggctcgggaa ggattgggga cagggctata ccctttgacg aatttgaccc ggcaaagcac    2280
aagtacaatg cagaatacta catcgagaac caggttcttc cagctgtgga gaggattctg    2340
agggcctttg gttaccgtaa agaagattta aggtatcaga aaacgcggca ggttggcttg    2400
ggggcgtggc taaaacctaa gacaagctgg atctgcgcaa ccgtaaagtt caagtacaaa    2460
ggcgaagaaa aagaggtaga catctccaag atcaagaaag tatggcgtgt gggcaagatg    2520
atctccttca cctacgacga gggcggtggc aagaccggcc gcggtgcggt aagcgaaaag    2580
gacgcgccga aggagctgct gcagatgctg gagaagcaga aaaagattta gtgg          2634
```

<210> SEQ ID NO 13
<211> LENGTH: 31
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 13

Met Val Asp Asp Leu Gln Arg Pro His His His His His Pro Trp
1               5                   10                  15

Asp Tyr Lys Asp Asp Asp Lys Pro Arg Trp Asn Ser Gly Trp
            20                  25                  30

<210> SEQ ID NO 14
<211> LENGTH: 36
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 14

Met Ile Asp Leu Gln Arg Pro Gln Ala Ala Thr Met Asp Ser Arg His
1               5                   10                  15

His His His His His Pro Trp Asp Tyr Lys Asp Asp Asp Lys Pro
            20                  25                  30

Arg Trp Asn Ser
        35

<210> SEQ ID NO 15
<211> LENGTH: 108
<212> TYPE: DNA
<213> ORGANISM: Artificial Sequence
<220> FEATURE:

```
<223> OTHER INFORMATION: Description of Artificial Sequence: Synthetic
      polynucleotide

<400> SEQUENCE: 15
atgatcgacc tgcagcggcc gcaggccgcc accatggact ctagacacca tcaccatcac      60
cacccatggg attacaagga cgacgatgac aagccgcggt ggaattcc                  108

<210> SEQ ID NO 16
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Met Ile Asp Leu Gln Arg Pro Ser Ala Ala Thr Met Val Asp Asp Leu
1               5                   10                  15

Gln Arg Pro His His His His His His Pro Trp Asp Tyr Lys Asp Asp
            20                  25                  30

Asp Asp Lys Pro Arg Trp Asn Ser
        35                  40

<210> SEQ ID NO 17
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
atgatcgacc tgcagcggcc atccgccgcc accatggtcg acgacctgca gcggccgcac      60
catcaccatc accatccatg ggattacaag gacgacgatg acaagccgcg gtggaattcg     120

<210> SEQ ID NO 18
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Met Val Asp Asp Leu Gln Arg Pro His His His His His His Pro Trp
1               5                   10                  15

Asp Tyr Lys Asp Asp Asp Asp Lys Pro Arg Trp Asn Ser
            20                  25

<210> SEQ ID NO 19
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
atggtcgacg acctgcagcg gccgcaccat caccatcacc atccatggga ttacaaggac      60
gacgatgaca agccgcggtg gaattcg                                          87

<210> SEQ ID NO 20
<211> LENGTH: 207
```

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

```
Met Ile Asp Leu Gln Arg Pro Ser Ala Ala Thr Met Val Asp Asp Leu
1               5                   10                  15

Gln Arg Pro His His His His His His Pro Trp Asp Tyr Lys Asp Asp
            20                  25                  30

Asp Asp Lys Pro Arg Trp Asn Ser Gly Ala Pro Pro Arg Leu Ile Cys
        35                  40                  45

Asp Ser Arg Val Leu Glu Arg Tyr Leu Leu Glu Ala Lys Glu Ala Glu
    50                  55                  60

Asn Ile Thr Thr Gly Cys Ala Glu His Cys Ser Leu Asn Glu Asn Ile
65                  70                  75                  80

Thr Val Pro Asp Thr Lys Val Asn Phe Tyr Ala Trp Lys Arg Met Glu
                85                  90                  95

Val Gly Gln Gln Ala Val Glu Val Trp Gln Gly Leu Ala Leu Leu Ser
            100                 105                 110

Glu Ala Val Leu Arg Gly Gln Ala Leu Leu Val Asn Ser Ser Gln Pro
        115                 120                 125

Trp Glu Pro Leu Gln Leu His Val Asp Lys Ala Val Ser Gly Leu Arg
    130                 135                 140

Ser Leu Thr Thr Leu Leu Arg Ala Leu Gly Ala Gln Lys Glu Ala Ile
145                 150                 155                 160

Ser Pro Pro Asp Ala Ala Ser Ala Ala Pro Leu Arg Thr Ile Thr Ala
                165                 170                 175

Asp Thr Phe Arg Lys Leu Phe Arg Val Tyr Ser Asn Phe Leu Arg Gly
            180                 185                 190

Lys Leu Lys Leu Tyr Thr Gly Glu Ala Cys Arg Thr Gly Asp Arg
        195                 200                 205
```

<210> SEQ ID NO 21
<211> LENGTH: 621
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21

```
atgatcgacc tgcagcggcc atccgccgcc accatggtcg acgacctgca gcggccgcac      60
catcaccatc accatccatg ggattacaag gacgacgatg acaagccgcg gtggaattcg     120
ggggccccac cacgcctcat ctgtgacagc cgagtcctgg agaggtacct cttggaggcc     180
aaggaggccg agaatatcac gacgggctgt gctgaacact gcagcttgaa tgagaatatc     240
actgtcccag acaccaaagt taatttctat gcctggaaga ggatggaggt cgggcagcag     300
gccgtagaag tctggcaggg cctggccctg ctgtcggaag ctgtcctgcg gggccaggcc     360
ctgttggtca actcttccca gccgtgggag cccctgcagc tgcatgtgga taaagccgtc     420
agtggccttc gcagcctcac cactctgctt cgggctctgg gagcccagaa ggaagccatc     480
tcccctccag atgcggcctc agctgctcca ctccgaacaa tcactgctga cactttccgc     540
aaactcttcc gagtctactc caatttcctc cggggaaagc tgaagctgta cacaggggag     600
gcctgcagga caggggacag a                                              621
```

<210> SEQ ID NO 22
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

```
Met Ile Asp Leu Gln Arg Pro Ser Ala Ala Thr Met Val Asp Asp Leu
1               5                   10                  15

Gln Arg Pro His His His His His His Pro Trp Asp Tyr Lys Asp Asp
            20                  25                  30

Asp Asp Lys Pro Arg Trp Asn Ser Lys Val Leu Ala Ala Gly Val Val
        35                  40                  45

Pro Leu Leu Leu Val Leu His Trp Lys His Gly Ala Gly Ser Pro Leu
    50                  55                  60

Pro Ile Thr Pro Val Asn Ala Thr Cys Ala Ile Arg His Pro Cys His
65                  70                  75                  80

Asn Asn Leu Met Asn Gln Ile Arg Ser Gln Leu Ala Gln Leu Asn Gly
                85                  90                  95

Ser Ala Asn Ala Leu Phe Ile Leu Tyr Tyr Thr Ala Gln Gly Glu Pro
            100                 105                 110

Phe Pro Asn Asn Leu Asp Lys Leu Cys Gly Pro Asn Val Thr Asp Phe
        115                 120                 125

Pro Pro Phe His Ala Asn Gly Thr Glu Lys Ala Lys Leu Val Glu Leu
    130                 135                 140

Tyr Arg Ile Val Val Tyr Leu Gly Thr Ser Leu Gly Asn Ile Thr Arg
145                 150                 155                 160

Asp Gln Lys Ile Leu Asn Pro Ser Ala Leu Ser Leu His Ser Lys Leu
                165                 170                 175

Asn Ala Thr Ala Asp Ile Leu Arg Gly Leu Leu Ser Asn Val Leu Cys
            180                 185                 190

Arg Leu Cys Ser Lys Tyr His Val Gly His Val Asp Val Thr Tyr Gly
        195                 200                 205

Pro Asp Thr Ser Gly Lys Asp Val Phe Gln Lys Lys Leu Gly Cys
    210                 215                 220

Gln Leu Leu Gly Lys Tyr Lys Gln Ile Ile Ala Val Leu Ala Gln Ala
225                 230                 235                 240

Phe
```

<210> SEQ ID NO 23
<211> LENGTH: 723
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23

```
atgatcgacc tgcagcggcc atccgccgcc accatggtcg acgacctgca gcggccgcac      60
catcaccatc accatccatg ggattacaag gacgacgatg acaagccgcg gtggaattcg     120
aaagtgctgg cggcgggcgt ggtgccgctg ctgctggtgc tgcattggaa acatggcgcg     180
ggcagcccgc tgccgattac cccggtgaac gcgacctgcg cgattcgcca tccgtgccat     240
aacaacctga tgaaccagat tcgcagccag ctggcgcagc tgaacggcag cgcgaacgcg     300
```

```
ctgtttattc tgtattatac cgcgcagggc gaaccgtttc cgaacaacct ggataaactg      360
tgcggcccga acgtgaccga ttttccgccg tttcatgcga acggcaccga aaaagcgaaa      420
ctggtggaac tgtatcgcat tgtggtgtat ctgggcacca gcctgggcaa cattacccgc      480
gatcagaaaa ttctgaaccc gagcgcgctg agcctgcata gcaaactgaa cgcgaccgcg      540
gatattctgc gcggcctgct gagcaacgtg ctgtgccgcc tgtgcagcaa atatcatgtg      600
ggccatgtgg atgtgaccta tggcccggat accagcggca agatgtgtt tcagaaaaaa      660 aaactgggct gccagctgct gggcaaatat aaacagatta ttgcggtgct ggcgcaggcg      720
ttt                                                                   723
```

<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Asp Asp Asp Asp Lys
1               5

<210> SEQ ID NO 25
<211> LENGTH: 15
<212> TYPE: DNA
<213> ORGANISM: Artificial Sequence
<220> FEATURE:
<223> OTHER INFORMATION: Description of Artificial Sequence: Synthetic
      consensus Kozak oligonucleotide

<400> SEQUENCE: 25
gccgccacca tggtc                                                       15

<210> SEQ ID NO 26
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 26

His His His His His His His His His His His His His His His His
1               5                   10                  15

His His His His
            20

<210> SEQ ID NO 27
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(20)
<223> OTHER INFORMATION: This region may encompass 1 to 20 "His"
      residues
<220> FEATURE:
<223> OTHER INFORMATION: see specification as filed for detailed description of substitutions and preferred embodiments

<400> SEQUENCE: 27

His His His His His His His His His His His His His His His  
1               5                   10                  15

His His His His  
            20

<210> SEQ ID NO 28
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(5)
<223> OTHER INFORMATION: This region may encompass 1 to 5 "His" residues

<400> SEQUENCE: 28

His His His His His  
1               5

<210> SEQ ID NO 29
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(6)
<223> OTHER INFORMATION: This region may encompass 2 to 6 "His" residues

<400> SEQUENCE: 29

His His His His His His  
1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(7)
<223> OTHER INFORMATION: This region may encompass 3 to 7 "His" residues

<400> SEQUENCE: 30

His His His His His His His  
1               5

<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(8)
<223> OTHER INFORMATION: This region may encompass 4 to 8 "His" residues

<400> SEQUENCE: 31

His His His His His His His His
1               5

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(9)
<223> OTHER INFORMATION: This region may encompass 5 to 9 "His" residues

<400> SEQUENCE: 32

His His His His His His His His His
1               5

<210> SEQ ID NO 33
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(10)
<223> OTHER INFORMATION: This region may encompass 6 to 10 "His"
      residues

<400> SEQUENCE: 33

His His His His His His His His His His
1               5                   10

<210> SEQ ID NO 34
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(11)
<223> OTHER INFORMATION: This region may encompass 7 to 11 "His"
      residues

<400> SEQUENCE: 34

His His His His His His His His His His His
1               5                   10

<210> SEQ ID NO 35
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(12)
<223> OTHER INFORMATION: This region may encompass 8 to 12 "His"
      residues

<400> SEQUENCE: 35

His His His His His His His His His His His His
1               5                   10

-continued

```
<210> SEQ ID NO 36
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(13)
<223> OTHER INFORMATION: This region may encompass 9 to 13 "His"
      residues

<400> SEQUENCE: 36

His His His His His His His His His His His His His
1               5                   10

<210> SEQ ID NO 37
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(14)
<223> OTHER INFORMATION: This region may encompass 10 to 14 "His"
      residues

<400> SEQUENCE: 37

His His His His His His His His His His His His His
1               5                   10

<210> SEQ ID NO 38
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(10)
<223> OTHER INFORMATION: This region may encompass 1 to 10 "His"
      residues

<400> SEQUENCE: 38

His His His His His His His His His His
1               5                   10

<210> SEQ ID NO 39
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(11)
<223> OTHER INFORMATION: This region may encompass 2 to 11 "His"
      residues

<400> SEQUENCE: 39

His His His His His His His His His His His
1               5                   10

<210> SEQ ID NO 40
<211> LENGTH: 12
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(12)
<223> OTHER INFORMATION: This region may encompass 3 to 12 "His"
      residues

<400> SEQUENCE: 40

His His His His His His His His His His His His
1               5                   10

<210> SEQ ID NO 41
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(13)
<223> OTHER INFORMATION: This region may encompass 4 to 13 "His"
      residues

<400> SEQUENCE: 41

His His His His His His His His His His His His His
1               5                   10

<210> SEQ ID NO 42
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(14)
<223> OTHER INFORMATION: This region may encompass 5 to 14 "His"
      residues

<400> SEQUENCE: 42

His His His His His His His His His His His His His His
1               5                   10

<210> SEQ ID NO 43
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(15)
<223> OTHER INFORMATION: This region may encompass 6 to 15 "His"
      residues

<400> SEQUENCE: 43

His His His His His His His His His His His His His His His
1               5                   10                  15

<210> SEQ ID NO 44
<211> LENGTH: 16
<212> TYPE: PRT
<213> ORGANISM: Artificial Sequence
<220> FEATURE:
<223> OTHER INFORMATION: Description of Artificial Sequence: Synthetic
```

```
      peptide
<220> FEATURE:
<221> NAME/KEY: misc_feature
<222> LOCATION: (1)..(16)
<223> OTHER INFORMATION: This region may encompass 7 to 16 "His"
      residues

<400> SEQUENCE: 44

His His His His His His His His His His His His His His His His
1               5                   10                  15

<210> SEQ ID NO 45
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(17)
<223> OTHER INFORMATION: This region may encompass 8 to 17 "His"
      residues

<400> SEQUENCE: 45

His His His His His His His His His His His His His His His His
1               5                   10                  15

His

<210> SEQ ID NO 46
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(19)
<223> OTHER INFORMATION: This region may encompass 9 to 19 "His"
      residues

<400> SEQUENCE: 46

His His His His His His His His His His His His His His His His
1               5                   10                  15

His His His

<210> SEQ ID NO 47
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(20)
<223> OTHER INFORMATION: This region may encompass 10 to 20 "His"
      residues

<400> SEQUENCE: 47

His His His His His His His His His His His His His His His His
1               5                   10                  15

His His His His
            20

<210> SEQ ID NO 48
<211> LENGTH: 20
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(20)
<223> OTHER INFORMATION: This region may encompass 1 to 20 "His"
      residues

<400> SEQUENCE: 48

His His His His His His His His His His His His His His His His
1               5                   10                  15

His His His His
            20

<210> SEQ ID NO 49
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(19)
<223> OTHER INFORMATION: This region may encompass 2 to 19 "His"
      residues

<400> SEQUENCE: 49

His His His His His His His His His His His His His His His His
1               5                   10                  15

His His His

<210> SEQ ID NO 50
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(18)
<223> OTHER INFORMATION: This region may encompass 3 to 18 "His"
      residues

<400> SEQUENCE: 50

His His His His His His His His His His His His His His His His
1               5                   10                  15

His His

<210> SEQ ID NO 51
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(17)
<223> OTHER INFORMATION: This region may encompass 4 to 17 "His"
      residues

<400> SEQUENCE: 51

His His His His His His His His His His His His His His His His
1               5                   10                  15
```

His

<210> SEQ ID NO 52
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(16)
<223> OTHER INFORMATION: This region may encompass 5 to 16 "His"
      residues

<400> SEQUENCE: 52

His His His His His His His His His His His His His His His His
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(15)
<223> OTHER INFORMATION: This region may encompass 6 to 15 "His"
      residues

<400> SEQUENCE: 53

His His His His His His His His His His His His His His His
1               5                   10                  15

<210> SEQ ID NO 54
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(14)
<223> OTHER INFORMATION: This region may encompass 7 to 14 "His"
      residues

<400> SEQUENCE: 54

His His His His His His His His His His His His His His
1               5                   10

<210> SEQ ID NO 55
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(13)
<223> OTHER INFORMATION: This region may encompass 8 to 13 "His"
      residues

<400> SEQUENCE: 55

His His His His His His His His His His His His His
1               5                   10

```
<210> SEQ ID NO 56
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(12)
<223> OTHER INFORMATION: This region may encompass 9 to 12 "His"
      residues

<400> SEQUENCE: 56

His His His His His His His His His His His His
1               5                   10

<210> SEQ ID NO 57
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(11)
<223> OTHER INFORMATION: This region may encompass 10 to 11 "His"
      residues

<400> SEQUENCE: 57

His His His His His His His His His His His
1               5                   10

<210> SEQ ID NO 58
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(6)
<223> OTHER INFORMATION: This region may encompass 1 to 6 "His" residues

<400> SEQUENCE: 58

His His His His His His
1               5

<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(7)
<223> OTHER INFORMATION: This region may encompass 1 to 7 "His" residues

<400> SEQUENCE: 59

His His His His His His His
1               5

<210> SEQ ID NO 60
<211> LENGTH: 8
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: misc_feature
<222> LOCATION: (1)..(8)
<223> OTHER INFORMATION: This region may encompass 1 to 8 "His" residues

<400> SEQUENCE: 60

His His His His His His His His
1               5

<210> SEQ ID NO 61
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(9)
<223> OTHER INFORMATION: This region may encompass 1 to 9 "His" residues

<400> SEQUENCE: 61

His His His His His His His His His
1               5

<210> SEQ ID NO 62
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 62

Asp Asp Asp Asp Asp Asp Asp Asp Asp Asp Asp Asp Asp Asp Asp Asp
1               5                   10                  15

Asp Asp Asp Asp
            20

<210> SEQ ID NO 63
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for detailed
      description of substitutions and preferred embodiments

<400> SEQUENCE: 63

Asp Asp Asp Asp
1

<210> SEQ ID NO 64
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(20)
```

```
<223> OTHER INFORMATION: This region may encompass 1 to 20 "Asp"
      residues
<220> FEATURE:
<223> OTHER INFORMATION: see specification as filed for detailed
      description of substitutions and preferred embodiments

<400> SEQUENCE: 64

Asp Asp Asp Asp Asp Asp Asp Asp Asp Asp Asp Asp Asp Asp Asp Asp
1               5                   10                  15

Asp Asp Asp Asp
            20

<210> SEQ ID NO 65
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(5)
<223> OTHER INFORMATION: This region may encompass 1 to 5 "Asp" residues

<400> SEQUENCE: 65

Asp Asp Asp Asp Asp
1               5

<210> SEQ ID NO 66
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(6)
<223> OTHER INFORMATION: This region may encompass 2 to 6 "Asp" residues

<400> SEQUENCE: 66

Asp Asp Asp Asp Asp Asp
1               5

<210> SEQ ID NO 67
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(7)
<223> OTHER INFORMATION: This region may encompass 3 to 7 "Asp" residues

<400> SEQUENCE: 67

Asp Asp Asp Asp Asp Asp Asp
1               5

<210> SEQ ID NO 68
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(8)
```

<223> OTHER INFORMATION: This region may encompass 4 to 8 "Asp" residues

<400> SEQUENCE: 68

Asp Asp Asp Asp Asp Asp Asp Asp
1               5

<210> SEQ ID NO 69
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(9)
<223> OTHER INFORMATION: This region may encompass 5 to 9 "Asp" residues

<400> SEQUENCE: 69

Asp Asp Asp Asp Asp Asp Asp Asp Asp
1               5

<210> SEQ ID NO 70
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(10)
<223> OTHER INFORMATION: This region may encompass 6 to 10 "Asp"
      residues

<400> SEQUENCE: 70

Asp Asp Asp Asp Asp Asp Asp Asp Asp Asp
1               5                   10

<210> SEQ ID NO 71
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(11)
<223> OTHER INFORMATION: This region may encompass 7 to 11 "Asp"
      residues

<400> SEQUENCE: 71

Asp Asp Asp Asp Asp Asp Asp Asp Asp Asp Asp
1               5                   10

<210> SEQ ID NO 72
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(12)
<223> OTHER INFORMATION: This region may encompass 8 to 12 "Asp"
      residues

<400> SEQUENCE: 72

Asp Asp Asp Asp Asp Asp Asp Asp Asp Asp Asp
1               5                   10

<210> SEQ ID NO 73
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(13)
<223> OTHER INFORMATION: This region may encompass 9 to 13 "Asp"
      residues

<400> SEQUENCE: 73

Asp Asp Asp Asp Asp Asp Asp Asp Asp Asp Asp Asp Asp
1               5                   10

<210> SEQ ID NO 74
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(14)
<223> OTHER INFORMATION: This region may encompass 10 to 14 "Asp"
      residues

<400> SEQUENCE: 74

Asp Asp Asp Asp Asp Asp Asp Asp Asp Asp Asp Asp Asp Asp
1               5                   10

<210> SEQ ID NO 75
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(10)
<223> OTHER INFORMATION: This region may encompass 1 to 10 "Asp"
      residues

<400> SEQUENCE: 75

Asp Asp Asp Asp Asp Asp Asp Asp Asp Asp
1               5                   10

<210> SEQ ID NO 76
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(11)
<223> OTHER INFORMATION: This region may encompass 2 to 11 "Asp"
      residues

<400> SEQUENCE: 76

Asp Asp Asp Asp Asp Asp Asp Asp Asp Asp Asp
1               5                   10

```
<210> SEQ ID NO 77
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(12)
<223> OTHER INFORMATION: This region may encompass 3 to 12 "Asp"
      residues

<400> SEQUENCE: 77

Asp Asp Asp Asp Asp Asp Asp Asp Asp Asp Asp Asp
1               5                   10

<210> SEQ ID NO 78
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(13)
<223> OTHER INFORMATION: This region may encompass 4 to 13 "Asp"
      residues

<400> SEQUENCE: 78

Asp Asp Asp Asp Asp Asp Asp Asp Asp Asp Asp Asp Asp
1               5                   10

<210> SEQ ID NO 79
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(14)
<223> OTHER INFORMATION: This region may encompass 5 to 14 "Asp"
      residues

<400> SEQUENCE: 79

Asp Asp Asp Asp Asp Asp Asp Asp Asp Asp Asp Asp Asp Asp
1               5                   10

<210> SEQ ID NO 80
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(15)
<223> OTHER INFORMATION: This region may encompass 6 to 15 "Asp"
      residues

<400> SEQUENCE: 80

Asp Asp Asp Asp Asp Asp Asp Asp Asp Asp Asp Asp Asp Asp Asp
1               5                   10                  15

<210> SEQ ID NO 81
<211> LENGTH: 16
```

-continued

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(16)
<223> OTHER INFORMATION: This region may encompass 7 to 16 "Asp"
      residues

<400> SEQUENCE: 81

Asp Asp Asp Asp Asp Asp Asp Asp Asp Asp Asp Asp Asp Asp Asp Asp
1               5                   10                  15

<210> SEQ ID NO 82
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(17)
<223> OTHER INFORMATION: This region may encompass 8 to 17 "Asp"
      residues

<400> SEQUENCE: 82

Asp Asp Asp Asp Asp Asp Asp Asp Asp Asp Asp Asp Asp Asp Asp Asp
1               5                   10                  15

Asp

<210> SEQ ID NO 83
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(19)
<223> OTHER INFORMATION: This region may encompass 9 to 19 "Asp"
      residues

<400> SEQUENCE: 83

Asp Asp Asp Asp Asp Asp Asp Asp Asp Asp Asp Asp Asp Asp Asp Asp
1               5                   10                  15

Asp Asp Asp

<210> SEQ ID NO 84
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(20)
<223> OTHER INFORMATION: This region may encompass 10 to 20 "Asp"
      residues

<400> SEQUENCE: 84

Asp Asp Asp Asp Asp Asp Asp Asp Asp Asp Asp Asp Asp Asp Asp Asp
1               5                   10                  15

Asp Asp Asp Asp
            20
```

```
<210> SEQ ID NO 85
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(20)
<223> OTHER INFORMATION: This region may encompass 1 to 20 "Asp"
      residues

<400> SEQUENCE: 85

Asp Asp Asp Asp Asp Asp Asp Asp Asp Asp Asp Asp Asp Asp Asp Asp
1               5                   10                  15

Asp Asp Asp Asp
            20

<210> SEQ ID NO 86
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(19)
<223> OTHER INFORMATION: This region may encompass 2 to 19 "Asp"
      residues

<400> SEQUENCE: 86

Asp Asp Asp Asp Asp Asp Asp Asp Asp Asp Asp Asp Asp Asp Asp Asp
1               5                   10                  15

Asp Asp Asp

<210> SEQ ID NO 87
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(18)
<223> OTHER INFORMATION: This region may encompass 3 to 18 "Asp"
      residues

<400> SEQUENCE: 87

Asp Asp Asp Asp Asp Asp Asp Asp Asp Asp Asp Asp Asp Asp Asp Asp
1               5                   10                  15

Asp Asp

<210> SEQ ID NO 88
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(17)
<223> OTHER INFORMATION: This region may encompass 4 to 17 "Asp"
      residues
```

```
<400> SEQUENCE: 88

Asp Asp Asp Asp Asp Asp Asp Asp Asp Asp Asp Asp Asp Asp Asp
1               5                   10                  15

Asp

<210> SEQ ID NO 89
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(16)
<223> OTHER INFORMATION: This region may encompass 5 to 16 "Asp"
      residues

<400> SEQUENCE: 89

Asp Asp Asp Asp Asp Asp Asp Asp Asp Asp Asp Asp Asp Asp Asp Asp
1               5                   10                  15

<210> SEQ ID NO 90
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(15)
<223> OTHER INFORMATION: This region may encompass 6 to 15 "Asp"
      residues

<400> SEQUENCE: 90

Asp Asp Asp Asp Asp Asp Asp Asp Asp Asp Asp Asp Asp Asp Asp
1               5                   10                  15

<210> SEQ ID NO 91
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(14)
<223> OTHER INFORMATION: This region may encompass 7 to 14 "Asp"
      residues

<400> SEQUENCE: 91

Asp Asp Asp Asp Asp Asp Asp Asp Asp Asp Asp Asp Asp Asp
1               5                   10

<210> SEQ ID NO 92
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(13)
<223> OTHER INFORMATION: This region may encompass 8 to 13 "Asp"
      residues

<400> SEQUENCE: 92
```

Asp Asp Asp Asp Asp Asp Asp Asp Asp Asp Asp Asp
1               5                   10

<210> SEQ ID NO 93
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(12)
<223> OTHER INFORMATION: This region may encompass 9 to 12 "Asp"
      residues

<400> SEQUENCE: 93

Asp Asp Asp Asp Asp Asp Asp Asp Asp Asp Asp Asp
1               5                   10

<210> SEQ ID NO 94
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(11)
<223> OTHER INFORMATION: This region may encompass 10 to 11 "Asp"
      residues

<400> SEQUENCE: 94

Asp Asp Asp Asp Asp Asp Asp Asp Asp Asp Asp
1               5                   10

<210> SEQ ID NO 95
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(6)
<223> OTHER INFORMATION: This region may encompass 1 to 6 "Asp"
      residues

<400> SEQUENCE: 95

Asp Asp Asp Asp Asp Asp
1               5

<210> SEQ ID NO 96
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(7)
<223> OTHER INFORMATION: This region may encompass 1 to 7 "Asp"
      residues

<400> SEQUENCE: 96

Asp Asp Asp Asp Asp Asp Asp
1               5

<210> SEQ ID NO 97
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(8)
<223> OTHER INFORMATION: This region may encompass 1 to 8 "Asp"
      residues

<400> SEQUENCE: 97

Asp Asp Asp Asp Asp Asp Asp Asp
1               5

<210> SEQ ID NO 98
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(9)
<223> OTHER INFORMATION: This region may encompass 1 to 9 "Asp"
      residues

<400> SEQUENCE: 98

Asp Asp Asp Asp Asp Asp Asp Asp Asp
1               5

<210> SEQ ID NO 99
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
tttttttttt                                                          10

<210> SEQ ID NO 100
<211> LENGTH: 13
<212> TYPE: RNA
<213> ORGANISM: Artificial Sequence
<220> FEATURE:
<223> OTHER INFORMATION: Description of Artificial Sequence: Synthetic
      consensus Kozak oligonucleotide

<400> SEQUENCE: 100
gccgccrcca ugg                                                      13

<210> SEQ ID NO 101
<211> LENGTH: 5
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Met Val Asp Asp Leu
1               5